(12) United States Patent
Perez et al.

(10) Patent No.: US 10,077,287 B2
(45) Date of Patent: Sep. 18, 2018

(54) TUBULYSIN ANALOGS AND METHODS OF MAKING AND USE

(71) Applicant: Bristol-Myers Squibb Company, Princeton, NJ (US)

(72) Inventors: Heidi L. Perez, Ewing, NJ (US); Donna Wei, Belle Mead, NJ (US); Robert M. Borzilleri, New Hope, PA (US); Sanjeev Gangwar, Foster City, CA (US); Gretchen M. Schroeder, Ewing, NJ (US); Heng Cheng, Foster City, CA (US); Robert J. Schmidt, Hainesport, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 181 days.

(21) Appl. No.: 14/833,422

(22) Filed: Aug. 24, 2015

(65) Prior Publication Data
US 2016/0130299 A1   May 12, 2016

Related U.S. Application Data

(60) Provisional application No. 62/077,399, filed on Nov. 10, 2014.

(51) Int. Cl.
| | |
|---|---|
| *A61K 47/65* | (2017.01) |
| *A61K 38/07* | (2006.01) |
| *C07K 5/10* | (2006.01) |
| *C07K 5/078* | (2006.01) |
| *C07K 5/062* | (2006.01) |
| *A61K 47/48* | (2006.01) |
| *C07K 16/30* | (2006.01) |

(52) U.S. Cl.
CPC .... *C07K 5/06139* (2013.01); *A61K 47/48438* (2013.01); *A61K 47/48569* (2013.01); *A61K 47/48715* (2013.01); *C07K 5/06026* (2013.01); *C07K 5/06034* (2013.01); *C07K 5/06052* (2013.01); *C07K 16/3038* (2013.01); *C07K 16/3046* (2013.01)

(58) Field of Classification Search
None
See application file for complete search history.

(56) References Cited

U.S. PATENT DOCUMENTS

| | | | |
|---|---|---|---|
| 7,691,962 B2 | 4/2010 | Boyd et al. | |
| 8,268,970 B2 | 9/2012 | Terrett et al. | |
| 8,394,922 B2 | 3/2013 | Cheng et al. | |
| 8,476,451 B2 | 7/2013 | Ellman et al. | |
| 8,580,820 B2 | 11/2013 | Zanda et al. | |
| 2002/0169125 A1 | 11/2002 | Leung et al. | |
| 2005/0239713 A1 | 10/2005 | Domling et al. | |
| 2005/0249740 A1 | 11/2005 | Domling et al. | |
| 2006/0128754 A1 | 6/2006 | Hoefle et al. | |
| 2006/0217360 A1 | 9/2006 | Hoefle et al. | |
| 2008/0176958 A1 | 7/2008 | Davis et al. | |
| 2008/0248052 A1 | 10/2008 | Vlahov et al. | |
| 2008/0279868 A1 | 11/2008 | Boyd et al. | |
| 2010/0047841 A1 | 2/2010 | Wipf et al. | |
| 2010/0048490 A1 | 2/2010 | Vlahov et al. | |
| 2010/0150950 A1 | 6/2010 | Coccia et al. | |
| 2010/0209432 A1 | 8/2010 | Terrett et al. | |
| 2010/0240701 A1 | 9/2010 | Vlahov et al. | |
| 2010/0323973 A1 | 12/2010 | Leamon et al. | |
| 2010/0324008 A1 | 12/2010 | Low et al. | |
| 2011/0245295 A1 | 10/2011 | Chai et al. | |
| 2012/0129779 A1 | 5/2012 | Richter | |
| 2012/0252738 A1 | 10/2012 | Richter | |
| 2012/0252739 A1 | 10/2012 | Richter | |
| 2013/0116195 A1 | 5/2013 | Leamon et al. | |
| 2013/0217638 A1 | 8/2013 | Wessjohann et al. | |
| 2013/0224228 A1 | 8/2013 | Jackson et al. | |
| 2013/0323271 A1 | 12/2013 | Mammen et al. | |

(Continued)

FOREIGN PATENT DOCUMENTS

| | | |
|---|---|---|
| DE | 10008089 | 10/2001 |
| DE | 102004030227 | 1/2006 |

(Continued)

OTHER PUBLICATIONS

Balasubramanian, R. et al., "Total Synthesis and Biological Evaluation of Tubulysin U, Tubulysin V, and Their Analogues", J. Med. Chemistry, vol. 52, pp. 238-240 (2009).

Balasubramanian, R. et al., "Tubulysin Analogs Incorporating Desmethyl and Dimethyl Tubuphenylalanine Derivatives", Bioorganic & Medicinal Chemistry Letters, vol. 18, pp. 2996-2999 (2008).

Chai, Y. et al., "Discovery of 23 Natural Tubulysins from Angiococcus Disciformis an d48 and Cystobacter SBCb004", Chemistry & Biology 17, vol. 17, pp. 296-309 (2010).

Domling A. et al., "Myxobacterial Epothilones and Tubulysins as Promising Anticancer Agents", Molecular Diversity, vol. 9, pp. 141-147 (2005).

(Continued)

*Primary Examiner* — Mark Halvorson
*Assistant Examiner* — Kauser M Akhoon
(74) *Attorney, Agent, or Firm* — Yuan Chao

(57) ABSTRACT

Tubulysin analogs of the formula (I)

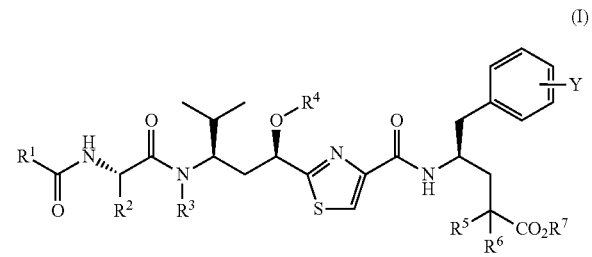

where $R^1$, $R^2$ $R^3$, $R^4$, $R^5$, $R^6$, $R^7$, and Y are as defined herein, are anti-mitotic agents that can be used in the treatment of cancer, especially when conjugated to a targeting moiety.

10 Claims, 11 Drawing Sheets

(56) References Cited

U.S. PATENT DOCUMENTS

2014/0107316 A1 4/2014 Vlahov et al.
2014/0227295 A1 8/2014 Cong et al.

FOREIGN PATENT DOCUMENTS

| WO | WO 97/21712    | 6/1997  |
|----|----------------|---------|
| WO | WO 98/13375    | 4/1998  |
| WO | WO 2013/173393 | 11/2013 |
| WO | WO 2014/009774 | 1/2014  |
| WO | WO 2014/040752 | 3/2014  |
| WO | WO 2014/078484 | 5/2014  |
| WO | WO 2014/080251 | 5/2014  |

OTHER PUBLICATIONS

Domling, A. et al., "Total Synthesis of Tubulysin U and V", Angew. Chem. Int. Ed., vol. 45, pp. 7235-7239 (2006).
Hamel, E. et al., "Antimitotic Peptides and Depsipeptides", Curr. Med. Chem—Anti-Cancer Agents, vol. 2, pp. 19-53 (2002).
Hoefle G. et al., "Semisynthesis and Degradation of the Tubulin Inhibitors Epothilone and Tubulysin", Pure and Applied Chemistry vol. 75 pp. 167-178 (2003).
Kaur, G. et al., "Biological Evaluation of Tubulysin A: A Potential Anti cancer and Antiangiogenic Natural Product", Biochem J.., vol. 396, pp. 235-242 (2006).
Khalil, M. et al., "Mechanism of Action of Tubulysin, An Antimitotic Peptide from Myxobacteria", ChemBioChem, vol. 7, pp. 678-683 (2006).
Leamon, C. et al., "Folate Targeting Enables Durable and Specific Antitumor Responses from a Therapeutically Null Tubulysin B Analogue", Cancer Research, vol. 68, pp. 9839-9844 (2008).
Lundquist J. T. et al., "Improved Solid-Phase Peptide Synthesis Method Utilizing r-Azide-Protected Amino Acids", Organic Letters vol. 3 pp. 781-783 (2001).
Neri, D. et al., "Efforts Toward the Total Synthesis of Tubulysins: New Hopes for a More Effective Targeted Drug Delivery to Tumors", Chem Med Chem., vol. 1, pp. 175-180 (2006).
Pando O. et al., "The Multiple Multicomponent Approach to Natural Product Mimics: Tubugis, N-Substituted Anticancer Peptides with Picomolar Activity", J. Am. Chem., vol. 133, pp. 7692-7695 (2011).
PatBase abstract of DE 10008089.
PatBase abstract of DE 102004030227.
PatBase abstract of WO 98/13375.
Patterson A. et al., "Expedient Synthesis of N-Methyl Tubulysin Analogues with High Cytotoxicity", J. Org. Chemistry, vol. 73, pp. 4362-4369 (2008).
Patterson, A. et al., "Design, Synthesis, and Biological Properties of Highly Potent Tubulysin D. Analogues", Chemistry Eur. J., vol. 13, pp. 9534-9541 (2007).
Peltier H. et al., "The Total Synthesis of Tubulysin D", J. Am. Chem., vol. 128, pp. 16018-16019 (2006).
Raghavan et al., "Cytotoxic Simplified Tubulysin Analogues", J. Med. Chem., 51: pp. 1530-1533: 2008.
Reddy J. et al., "In Vivo Structural Activity and Optimization Studies of Folate-Tubulysin Conjugates", Molecular Pharmaceutics, vol. 6 pp. 1518-1525 (2009).
Sani, M. et al, "Total Synthesis of Tubulysin U and V", Angew. Chem. Int. Ed., vol. 46, pp. 3526-3529 (2007).
Sasse F. et al., "Success in Tubulysin D Synthesis", Nature Chemical Biology, vol. 3 pp. 87-89 (2007).
Sasse, F. et al., "Tubulysins, New Cytostatic Peptides from Myxobacteria Acting on Microtubuli", J. Antibiotics, vol. 53, pp. 879-885 (2000).
Schluep, T. et al., "Polymeric Tubulysin-Peptide Nanoparticles With Potent Antitumor Activity", Clin Cancer Res, vol. 15, pp. 181-189 (2009).
Schrama D. et al., "Antibody Targeted Drugs as Cancer Therapeutics", Nature Reviews Drug Discovery, vol. 5 pp. 147-159 (2006).
Shankar S.P. et al., "Studies Towards a Novel Synthesis of Tubulysins: Highly Asymmetric Aza-Michael Reactions of 2-Enoylthiazoles with Metalated Chiral Oxazolidinones", SynLett vol. 8 pp. 1341-1345 (2009).
Shankar S.P. et al., "Synthesis and Structure-Activity Relationship Studies of Novel Tubulysin U Analogues—Effect on Cytotoxicity of Structural Variations in the Tubuvaline Fragment", Organic & Biomolecular Chemistry vol. 11 pp. 2273-2287 (2013).
Shankar S.P. et al., "Total Synthesis and Cytotoxicity Evaluation of an Oxazole Analogue of Tubulysin U", SynLett vol. 12 pp. 1673-1676 (2011).
Shibue T. et al., "Stereoselective Synthesis of Tubuvaline Methyl ester and Tubuphenylalanine, Components of Tubulysins, Tubulin Polymerization Inhibitors", Tetrahedron Letters vol. 50 pp. 3845-3848 (2009).
Shibue, T. et al., "Synthesis and Biological Evaluation of Tubulysin D. Analogs Related to Steroisomers of Tubuvaline", Bioorganic & Medicinal Chemistry Letters, vol. 21, pp. 431-434 (2011).
Shibue, T. et al., "Total Syntheses of Tubulysins", Chemistry Eur. J., vol. 16, pp. 11678-11688 (2010).
Steinmetz, H. et al., "Isolation, Crystal and Solution Structure Determination, and Biosynthesis of Tubulysins-Powerful Inhibitors of Tubulin Polymerization from Myxobacteria", Angew. Chem. Int. Ed., vol. 43, pp. 4888-4892 (2004).
Ullrich, A. et al, "Pretubulysin, a Potent and Chemically Acc3essible Tubulysin Precursor from Angiococcus Disciformis", Angew. Chem. Int. Ed., vol. 48, pp. 4422-4425 (2009).
Vlahov et al., "Design and Regioselective Synthesis of a New Generation of Targeted Chemotherapeutics. Part II: Folic Acid Conjugates of Tubulysins and Their Hydrazides", Bioorganic & Medicinal Chemistry Letters, vol. 18, pp. 4558-4561 (2008).
Vlahov, I. et al., "Acid Mediated Formation of an N-Acyliminium Ion from Tubulysins: A New Methodology for the Synthesis of Natural Tubulysins and Their Analogs", Bioorganic & Medicinal Chemistry Letters, vol. 21, pp. 6778-6781 (2011).
Wang, Z. et al., "Structure-Activity and High-Content Imaging Analyses of Novel Tubulysins", Chem Biol Drug Des, vol. 70, pp. 75-86 (2007).
Wipf P. et al., "Synthesis of the Tubuvaline—Total Synthesis of N14-Desacetoxytubulysin H", Organic Letters vol. 9 pp. 1605-1607 (2007).
Wipf P. et al., "Synthesis of the Tubuvaline-Tubuphenylalanine", Organic Letters vol. 6 pp. 4057-4060 (2004).
Notification of Transmittal of the PCT International Search Report & Written Opinion of the International Search Authority, pp. 01-15, dated Jan. 30, 2016.

(IIIa-4)

TUBULYSIN ANALOGS AND METHODS OF MAKING AND USE

CROSS-REFERENCE TO RELATED APPLICATIONS

This application claims the benefit under 35 U.S.C. § 119(e) of U.S. Provisional Application No. 62/077,399, filed Nov. 10, 2014; the disclosure of which is incorporated herein by reference.

BACKGROUND OF THE INVENTION

This invention relates to tubulysin analogs and conjugates thereof, methods for making and using them, and compositions comprising them.

The tubulysins are cytotoxins first isolated from cultures of the myxobacteria *Archangium gephyra* or *Angiococcus disciformis*, each producing a different tubulysin mixture (Sasse et al. 2000; Reichenbach et al. 1998). Their crystal structure and biosynthetic pathway have been elucidated (Steinmetz et al. 2004, Ullrich et al. 2009) and their biosynthesis genes have been sequenced (Hoefle et al. 2006b). (Full citations of the references cited herein by first author or inventor and year are listed at the end of this specification.)

The tubulysins belong to a group of antimitotic polypeptides and depsipeptides that includes the phomopsins, the dolastatins, and the cryptophycins (Hamel 2002). Other antimitotic agents are known, for example paclitaxel, the maytansines, and the epothilones. During mitosis, a cell's microtubules reorganize to form the mitotic spindle, a process requiring the rapid assembly and disassembly of the microtubule constituent proteins α- and β-tubulin. Antimitotic agents block this process and prevent a cell from undergoing mitosis. At the molecular level the exact blockage mechanism may differ from one antimitotic agent to another. The tubulysins prevent the assembly of the tubulins into microtubules, causing the affected cells to accumulate in the $G_2/M$ phase and undergo apoptosis (Khalil et al. 2006).

The tubulysins have a tetrapeptidyl scaffold consisting of one proteinogenic and three non-proteinogenic amino acid subunits as shown in formula (A): N-methylpipecolinic acid (Mep), isoleucine (Ile), tubuvaline (Tuv), and either tubuphenylalanine (Tup, R' equals H) or tubutyrosine (Tut, R' equals OH). Structural variations among the tubulysins (designated A, B, etc.) center around residues R', R" and R'" of formula (A), as shown in Table I. Recently, more naturally occurring tubulysins have been isolated (Chai et al. 2010).

TABLE I

Naturally Occurring Tubulysins (A)

| Tubulysin | R' | R" | R'" |
|---|---|---|---|
| A | OH | OC(=O)Me | $CH_2OC(=O)$i-Bu |
| B | OH | OC(=O)Me | $CH_2OC(=O)$n-Pr |
| C | OH | OC(=O)Me | $CH_2OC(=O)$Et |
| D | H | OC(=O)Me | $CH_2OC(=O)$i-Bu |
| E | H | OC(=O)Me | $CH_2OC(=O)$n-Pr |
| F | H | OC(=O)Me | $CH_2OC(=O)$Et |
| G | OH | OC(=O)Me | $CH_2OC(=O)CH=CH_2$ |
| H | H | OC(=O)Me | $CH_2OC(=O)$Me |
| I | OH | OC(=O)Me | $CH_2OC(=O)$Me |
| U | H | OC(=O)Me | H |
| V | H | OH | H |
| Y | OH | OC(=O)Me | H |
| Z | OH | OH | H |
| Pretubulysin | H | H | Me |

Kaur et al. 2006 studied the antiproliferative properties of tubulysin A and found that it was more potent than paclitaxel and vinblastine and active in xenograft assays against various cancer cell lines. Further, tubulysin A induced apoptosis in cancer cells but not in normal cells and showed significant potential antiangiogenic properties in in vitro assays. The antimitotic properties of other tubulysins have been evaluated and generally compare favorably against those of non-tubulysin antimitotic agents (see, e.g., Balasubramanian et al. 2009, Steinmetz et al. 2004, and Wipf et al. 2004). For these reasons, there is interest in the tubulysins as anti-cancer agents (see, e.g., Domling et al. 2005c and Hamel 2002).

Numerous publications describe efforts directed at the synthesis of tubulysins, including: Balasubramanian et al. 2009, Domling et al. 2006, Hoefle et al. 2003, Neri et al. 2006, Peltier et al. 2006, Sani et al. 2007, Sasse et al. 2007, Shankar et al. 2009, Shibue et al. 2009 and 2010, and Wipf et al. 2004.

Disclosures of tubulysin analogs in which the natural Mep subunit was replaced by an alternative group include Patterson et al. 2007, Wang et al. 2007, Wipf et al. 2010, Balasubramanian et al. 2009, Chai et al. 2011, and Miao et al. 2013.

Several tubulysin analogs where the Ile subunit was replaced by another amino acid have been disclosed: Wipf et al. 2010, Vlahov et al. 2014a, and Zhao et al. 2014b.

Cong et al. 2014 disclose replacement of the R″ acetate group in the Tub subunit with a carbamate group.

Cong et al. 2014 and Cheng et al. 2013 disclose tubulysin analogs in which the R′″ group of the Tuv subunit was replaced with alternative groups. They also disclose replacing the R′ group of the Tup/Tut subunit with an amino group, as a conjugation site.

Balasubramanian et al. 2008 and 2009 disclose tubulysin analogs in which the natural (17S)-Me group in the Tup subunit was replaced by a geminal dimethyl group in conjunction with replacement of the acetate group in the Tuv subunit with a carbonyl group.

Additional disclosures on the preparation of tubulysin analogs or derivatives include: Balasubramanian et al. 2008, Domling 2006, Domling et al. 2005a, Ellman et al. 2013, Hoefle et al. 2001 and 2006a, Pando et al. 2011, Patterson et al. 2008, Raghavan et al. 2008, Richter 2012a, 2012b, and 2012c, Shankar et al. 2013, Shibue et al. 2011, Sreejith et al. 2011, Vlahov et al. 2010a and 2011, Wessjohann et al. 2013, Wipf et al. 2007, Zanda et al. 2013, and Zhao et al. 2014a.

Domling et al. 2005 disclose conjugates of tubulysins with a partner molecule exemplified by polyethylene glycol (PEG). Other disclosures of conjugates of tubulysins are Boyd et al. 2008 and 2010, Jackson et al. 2013, Leamon et al. 2013, Vlahov et al. 2008a, 2008b, 2010b and 2014b, Leamon et al. 2008 and 2010, Reddy et al. 2009, Low et al. 2010, and Zhao et al. 2014a and 2014b. Leung et al. 2002 disclose polyanionic polypeptides that can be conjugated to drugs such as the tubulysins to improve their bioactivity and water solubility. Davis et al. 2008 and Schluep et al. 2009 disclose cyclodextrin based formulations in which tubulysins are covalently attached to a cyclodextrin.

BRIEF SUMMARY OF THE INVENTION

The present invention discloses tubulysin analogs having cytotoxic activity, which can be used as anti-cancer agents by administration as such, as a prodrug, or as a conjugate. The analogs are characterized by, inter alia, a geminal dimethyl group or a cyclopropyl group positioned alpha to the carboxyl group of the Tup/Tut subunit.

Accordingly, in one aspect, this invention provides a compound having a structure represented by formula (I)

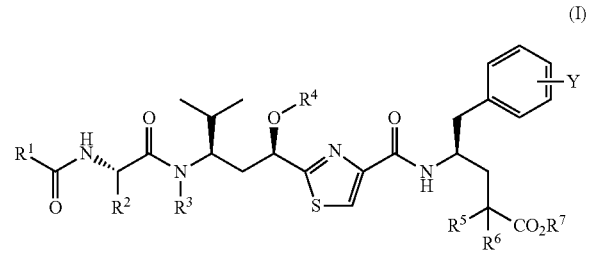

(I)

wherein
$R^1$ is

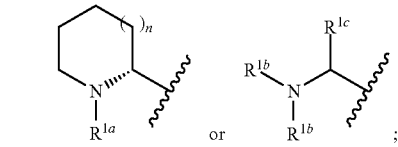

wherein
$R^{1a}$ is H, $C_1$-$C_5$ alkyl, $C_2$-$C_5$ alkenyl, $C_2$-$C_5$ alkynyl, $CO(C_1$-$C_5$ alkyl), $CO(C_2$-$C_5$ alkenyl), or $CO(C_2$-$C_5$ alkynyl);
each $R^{1b}$ is independently H or $C_{1-3}$ alkyl;
$R^{1c}$ is H, Me, or $CH(Me)_2$; and
n is 0, 1, or 2;
$R^2$ is H, unsubstituted or substituted $C_1$-$C_{10}$ alkyl, unsubstituted or substituted $C_2$-$C_{10}$ alkenyl, unsubstituted or substituted $C_2$-$C_{10}$ alkynyl, unsubstituted or substituted aryl, unsubstituted or substituted heteroaryl, unsubstituted or substituted $(CH_2)_{1-2}O(C_1$-$C_{10}$ alkyl), unsubstituted or substituted $(CH_2)_{1-2}O(C_2$-$C_{10}$ alkenyl), unsubstituted or substituted $(CH_2)_{1-2}O(C_2$-$C_{10}$ alkynyl), $(CH_2)_{1-2}OC(=O)(C_1$-$C_{10}$ alkyl), unsubstituted or substituted $(CH_2)_{1-2}OC(=O)(C_2$-$C_{10}$ alkenyl), unsubstituted or substituted $(CH_2)_{1-2}OC(=O)(C_2$-$C_{10}$ alkynyl), unsubstituted or substituted $C(=O)(C_1$-$C_{10}$ alkyl), unsubstituted or substituted $C(=O)(C_2$-$C_{10}$ alkenyl), unsubstituted or substituted $C(=O)(C_2$-$C_{10}$ alkynyl), unsubstituted or substituted cycloaliphatic, unsubstituted or substituted heterocycloaliphatic, unsubstituted or substituted arylalkyl, or unsubstituted or substituted alkylaryl;
$R^3$ is H, unsubstituted or substituted $C_1$-$C_{10}$ alkyl, unsubstituted or substituted $C_2$-$C_{10}$ alkenyl, unsubstituted or substituted $C_2$-$C_{10}$ alkynyl, unsubstituted or substituted aryl, unsubstituted or substituted heteroaryl, unsubstituted or substituted $(CH_2)_{1-2}O(C_1$-$C_{10}$ alkyl), unsubstituted or substituted $(CH_2)_{1-2}O(C_2$-$C_{10}$ alkenyl), unsubstituted or substituted $(CH_2)_{1-2}O(C_2$-$C_{10}$ alkynyl), $(CH_2)_{1-2}OC(=O)(C_1$-$C_{10}$ alkyl), unsubstituted or substituted $(CH_2)_{1-2}OC(=O)(C_2$-$C_{10}$ alkenyl), unsubstituted or substituted $(CH_2)_{1-2}OC(=O)(C_2$-$C_{10}$ alkynyl), unsubstituted or substituted $C(=O)(C_1$-$C_{10}$ alkyl), unsubstituted or substituted $C(=O)(C_2$-$C_{10}$ alkenyl), unsubstituted or substituted $C(=O)(C_2$-$C_{10}$ alkynyl), unsubstituted or substituted cycloaliphatic, unsubstituted or substituted heterocycloaliphatic, unsubstituted or substituted arylalkyl, unsubstituted or substituted alkylaryl, or

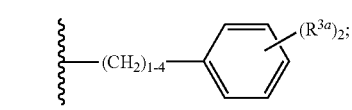

wherein each $R^{3a}$ is independently H, $NH_2$, NHMe, Cl, F, Me, Et, or CN;
$R^4$ is

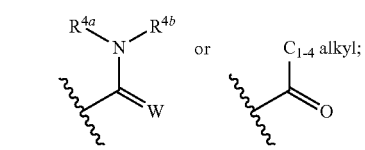

wherein

R$^{4a}$ and R$^{4b}$ are independently H, C$_1$-C$_5$ alkyl, CH$_2$(C$_5$-C$_6$ cycloalkyl), CH$_2$C$_6$H$_5$, C$_6$H$_5$, or CH$_2$CH$_2$OH; and W is O or S;

R$^5$ and R$^6$ are each Me or combine with the carbon to which they are bonded to form a cyclopropyl ring;

R$^7$ is H or C$_1$-C$_3$ alkyl; and

Y is H, OH, Cl, F, CN, Me, Et, NO$_2$, or NH$_2$;

or a pharmaceutically acceptable salt thereof.

In another embodiment, this invention provides a conjugate comprising a compound of formula (I) covalently linked to a targeting moiety that specifically or preferentially binds to a chemical entity on a target cell, which target cell preferably is a cancer cell. Preferably, the targeting moiety is an antibody—more preferably a monoclonal antibody; even more preferably a human monoclonal antibody—and the chemical entity is a tumor associated antigen. The tumor associated antigen can be one that is displayed on the surface of a cancer cell or one that is secreted by a cancer cell into the surrounding extracellular space.

In another embodiment, there is provided a compound according to formula (I) covalently bonded to a linker moiety having a reactive functional group, suitable for conjugation to a targeting moiety.

In another embodiment, there is provided a method for treating a cancer in a subject suffering from such cancer, comprising administering to the subject a therapeutically effective amount of a compound of this invention or a conjugate thereof with a targeting moiety. In another embodiment, there is provided the use of a compound of this invention or a conjugate thereof with a targeting moiety for the preparation of a medicament for the treatment of cancer in a subject suffering from such cancer. A compound of this invention or a conjugate thereof with a targeting moiety can also be used to inhibit the proliferation, in vitro or in vivo, of cancer cells. Especially, the cancer can be lung cancer, gastric cancer, ovarian cancer, colon cancer, breast cancer, or renal cancer.

BRIEF DESCRIPTION OF THE DRAWING(S)

DETAILED DESCRIPTION OF THE INVENTION

Definitions

Figure 1:
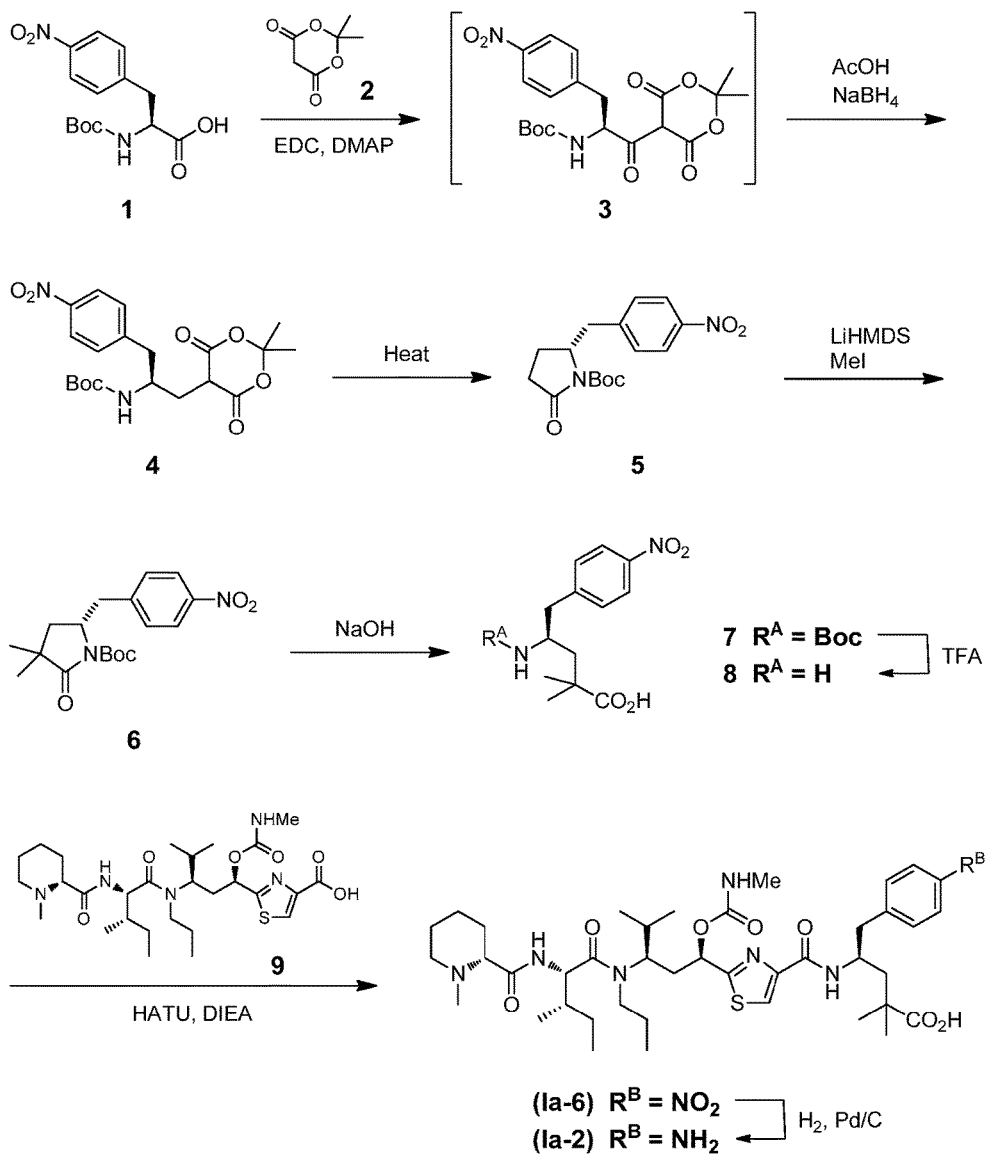
FIG. 1 shows a scheme for the synthesis of compounds (Ia-2) and (Ia-6).

"Antibody" means whole antibodies and any antigen binding fragment (i.e., "antigen-binding portion") or single chain variants thereof. A whole antibody is a protein comprising at least two heavy (H) chains and two light (L) chains inter-connected by disulfide bonds. Each heavy chain comprises a heavy chain variable region (V$_H$) and a heavy chain constant region comprising three domains, C$_{H1}$, C$_{H2}$ and C$_{H3}$. Each light chain comprises a light chain variable region (V$_L$ or V$_k$) and a light chain constant region comprising one single domain, C$_L$. The V$_H$ and V$_L$ regions can be further subdivided into regions of hypervariability, termed complementarity determining regions (CDRs), interspersed with more conserved framework regions (FRs). Each V$_H$ and V$_L$ comprises three CDRs and four FRs, arranged from amino- to carboxy-terminus in the following order: FR1, CDR1, FR2, CDR2, FR3, CDR3, and FR4. The variable regions contain a binding domain that interacts with an antigen. The constant regions may mediate the binding of the antibody to host tissues or factors, including various cells of the immune system (e.g., effector cells) and the first component (Clq) of the classical complement system. An antibody is said to "specifically bind" to an antigen X if the antibody binds to antigen X with a K$_D$ of $5 \times 10^{-8}$ M or less, more preferably $1 \times 10^{-8}$ M or less, more preferably $6 \times 10^{-9}$ M or less, more preferably $3 \times 10^{-9}$ M or less, even more preferably $2 \times 10^{-9}$ M or less. The antibody can be chimeric, humanized, or, preferably, human. The heavy chain constant region can be engineered to affect glycosylation type or extent, to extend antibody half-life, to enhance or reduce interactions with effector cells or the complement system, or to modulate some other property. The engineering can be accomplished by replacement, addition, or deletion of one or more amino acids or by replacement of a domain with a domain from another immunoglobulin type, or a combination of the foregoing.

"Antigen binding fragment" and "antigen binding portion" of an antibody (or simply "antibody portion" or "antibody fragment") mean one or more fragments of an antibody that retain the ability to specifically bind to an antigen. It has been shown that the antigen-binding function of an antibody can be performed by fragments of a full-length antibody, such as (i) a Fab fragment, a monovalent fragment consisting of the V$_L$, V$_H$, C$_L$ and C$_{H1}$ domains; (ii) a F(ab')$_2$ fragment, a bivalent fragment comprising two Fab fragments linked by a disulfide bridge at the hinge region; (iii) a Fab' fragment, which is essentially an Fab with part of the hinge region (see, for example, Abbas et al., *Cellular and Molecular Immunology*, 6th Ed., Saunders Elsevier 2007); (iv) a Fd fragment consisting of the V$_H$ and C$_{H1}$ domains; (v) a Fv fragment consisting of the V$_L$ and V$_H$ domains of a single arm of an antibody, (vi) a dAb fragment (Ward et al., (1989) *Nature* 341:544-546), which consists of a V$_H$ domain; (vii) an isolated complementarity determining region (CDR); and (viii) a nanobody, a heavy chain variable region containing a single variable domain and two constant domains. Preferred antigen binding fragments are Fab, F(ab')$_2$, Fab', Fv, and Fd fragments. Furthermore, although the two domains of the Fv fragment, V$_L$ and V$_H$, are encoded by separate genes, they can be joined, using recombinant methods, by a synthetic linker that enables them to be made as a single protein chain in which the V$_L$ and V$_H$ regions pair to form monovalent molecules (known as single chain Fv, or scFv); see, e.g., Bird et al. (1988) *Science* 242:423-426; and Huston et al. (1988) *Proc. Natl. Acad. Sci. USA* 85:5879-5883). Such single chain antibodies are also encompassed within the term "antigen-binding portion" of an antibody.

An "isolated antibody" means an antibody that is substantially free of other antibodies having different antigenic specificities (e.g., an isolated antibody that specifically binds antigen X is substantially free of antibodies that specifically bind antigens other than antigen X). An isolated antibody that specifically binds antigen X may, however, have cross-reactivity to other antigens, such as antigen X molecules from other species. In certain embodiments, an isolated antibody specifically binds to human antigen X and does not cross-react with other (non-human) antigen X antigens. Moreover, an isolated antibody may be substantially free of other cellular material and/or chemicals.

"Monoclonal antibody" or "monoclonal antibody composition" means a preparation of antibody molecules of single molecular composition, which displays a single binding specificity and affinity for a particular epitope.

"Human antibody" means an antibody having variable regions in which both the framework and CDR regions (and the constant region, if present) are derived from human germline immunoglobulin sequences. Human antibodies may include later modifications, including natural or synthetic modifications. Human antibodies may include amino acid residues not encoded by human germline immunoglobulin sequences (e.g., mutations introduced by random or site-specific mutagenesis in vitro or by somatic mutation in vivo). However, "human antibody" does not include antibodies in which CDR sequences derived from the germline of another mammalian species, such as a mouse, have been grafted onto human framework sequences.

"Human monoclonal antibody" means an antibody displaying a single binding specificity, which has variable regions in which both the framework and CDR regions are derived from human germline immunoglobulin sequences. In one embodiment, human monoclonal antibodies are produced by a hybridoma that includes a B cell obtained from a transgenic nonhuman animal, e.g., a transgenic mouse, having a genome comprising a human heavy chain transgene and a light chain transgene fused to an immortalized cell.

"Aliphatic" means a straight- or branched-chain, saturated or unsaturated, non-aromatic hydrocarbon moiety having the specified number of carbon atoms (e.g., as in "$C_3$ aliphatic," "$C_1$-$C_5$ aliphatic," or "$C_1$ to $C_5$ aliphatic," the latter two phrases being synonymous for an aliphatic moiety having from 1 to 5 carbon atoms) or, where the number of carbon atoms is not explicitly specified, from 1 to 4 carbon atoms (2 to 4 carbons in the instance of unsaturated aliphatic moieties). A similar understanding is applied to the number of carbons in other types, as in $C_{2-4}$ alkene, $C_4$-$C_7$ cycloaliphatic, etc. In a similar vein, a term such as "$(CH_2)_{1-3}$" is to be understand as shorthand for the subscript being 1, 2, or 3, so that such term represents $CH_2$, $CH_2CH_2$, and $CH_2CH_2CH_2$.

"Alkyl" means a saturated aliphatic moiety, with the same convention for designating the number of carbon atoms being applicable. By way of illustration, $C_1$-$C_4$ alkyl moieties include, but are not limited to, methyl, ethyl, propyl, isopropyl, isobutyl, t-butyl, 1-butyl, 2-butyl, and the like. "Alkylene" means a divalent counterpart of an alkyl group, such as $CH_2CH_2$, $CH_2CH_2CH_2$, and $CH_2CH_2CH_2CH_2$.

"Alkenyl" means an aliphatic moiety having at least one carbon-carbon double bond, with the same convention for designating the number of carbon atoms being applicable. By way of illustration, $C_2$-$C_4$ alkenyl moieties include, but are not limited to, ethenyl(vinyl), 2-propenyl(allyl or prop-2-enyl), cis-1-propenyl, trans-1-propenyl, E- (or Z-) 2-butenyl, 3-butenyl, 1,3-butadienyl(but-1,3-dienyl) and the like.

"Alkynyl" means an aliphatic moiety having at least one carbon-carbon triple bond, with the same convention for designating the number of carbon atoms being applicable.

By way of illustration, $C_2$-$C_4$ alkynyl groups include ethynyl (acetylenyl), propargyl(prop-2-ynyl), 1-propynyl, but-2-ynyl, and the like.

"Cycloaliphatic" means a saturated or unsaturated, non-aromatic hydrocarbon moiety having from 1 to 3 rings, each ring having from 3 to 8 (preferably from 3 to 6) carbon atoms. "Cycloalkyl" means a cycloaliphatic moiety in which each ring is saturated. "Cycloalkenyl" means a cycloaliphatic moiety in which at least one ring has at least one carbon-carbon double bond. "Cycloalkynyl" means a cycloaliphatic moiety in which at least one ring has at least one carbon-carbon triple bond. By way of illustration, cycloaliphatic moieties include, but are not limited to, cyclopropyl, cyclobutyl, cyclopentyl, cyclopentenyl, cyclohexyl, cyclohexenyl, cycloheptyl, cyclooctyl, and adamantyl. Preferred cycloaliphatic moieties are cycloalkyl ones, especially cyclopropyl, cyclobutyl, cyclopentyl, and cyclohexyl. "Cycloalkylene" means a divalent counterpart of a cycloalkyl group.

"Heterocycloaliphatic" means a cycloaliphatic moiety wherein, in at least one ring thereof, up to three (preferably 1 to 2) carbons have been replaced with a heteroatom independently selected from N, O, or S, where the N and S optionally may be oxidized and the N optionally may be quaternized. Similarly, "heterocycloalkyl," "heterocycloalkenyl," and "heterocycloalkynyl" means a cycloalkyl, cycloalkenyl, or cycloalkynyl moiety, respectively, in which at least one ring thereof has been so modified. Exemplary heterocycloaliphatic moieties include aziridinyl, azetidinyl, 1,3-dioxanyl, oxetanyl, tetrahydrofuryl, pyrrolidinyl, piperidinyl, piperazinyl, tetrahydropyranyl, tetrahydrothiopyranyl, tetrahydrothiopyranyl sulfone, morpholinyl, thiomorpholinyl, thiomorpholinyl sulfoxide, thiomorpholinyl sulfone, 1,3-dioxolanyl, tetrahydro-1,1-dioxothienyl, 1,4-dioxanyl, thietanyl, and the like. "Heterocycloalkylene" means a divalent counterpart of a heterocycloalkyl group.

"Alkoxy," "aryloxy," "alkylthio," and "arylthio" mean —O(alkyl), —O(aryl), —S(alkyl), and —S(aryl), respectively. Examples are methoxy, phenoxy, methylthio, and phenylthio, respectively.

"Halogen" or "halo" means fluorine, chlorine, bromine or iodine.

"Aryl" means a hydrocarbon moiety having a mono-, bi-, or tricyclic ring system wherein each ring has from 3 to 7 carbon atoms and at least one ring is aromatic. The rings in the ring system may be fused to each other (as in naphthyl) or bonded to each other (as in biphenyl) and may be fused or bonded to non-aromatic rings (as in indanyl or cyclohexylphenyl). By way of further illustration, aryl moieties include, but are not limited to, phenyl, naphthyl, tetrahydronaphthyl, indanyl, biphenyl, phenanthryl, anthracenyl, and acenaphthyl. "Arylene" means a divalent counterpart of an aryl group, for example 1,2-phenylene, 1,3-phenylene, or 1,4-phenylene.

"Heteroaryl" means a moiety having a mono-, bi-, or tricyclic ring system wherein each ring has from 3 to 7 carbon atoms and at least one ring is an aromatic ring containing from 1 to 4 heteroatoms independently selected from N, O, or S, where the N and S optionally may be oxidized and the N optionally may be quaternized. Such at least one heteroatom containing aromatic ring may be fused to other types of rings (as in benzofuranyl or tetrahydroisoquinolyl) or directly bonded to other types of rings (as in phenylpyridyl or 2-cyclopentylpyridyl). By way of further illustration, heteroaryl moieties include pyrrolyl, furanyl, thiophenyl(thienyl), imidazolyl, pyrazolyl, oxazolyl, isoxazolyl, thiazolyl, isothiazolyl, triazolyl, tetrazolyl, pyridyl, N-oxopyridyl, pyridazinyl, pyrimidinyl, pyrazinyl, quinolinyl, isoquinolynyl, quinazolinyl, cinnolinyl, quinozalinyl, naphthyridinyl, benzofuranyl, indolyl, benzothiophenyl, oxadiazolyl, thiadiazolyl, phenothiazolyl, benzimidazolyl, benzotriazolyl, dibenzofuranyl, carbazolyl, dibenzothiophenyl, acridinyl, and the like. "Heteroarylene" means a divalent counterpart of an aryl group.

Where it is indicated that a moiety may be substituted, such as by use of "unsubstituted or substituted" or "optionally substituted" phrasing as in "unsubstituted or substituted $C_1$-$C_5$ alkyl" or "optionally substituted heteroaryl," such moiety may have one or more independently selected substituents, preferably one to five in number, more preferably one or two in number. Substituents and substitution patterns can be selected by one of ordinary skill in the art, having regard for the moiety to which the substituent is attached, to provide compounds that are chemically stable and that can be synthesized by techniques known in the art as well as the methods set forth herein.

"Arylalkyl," (heterocycloaliphatic)alkyl," "arylalkenyl," "arylalkynyl," "biarylalkyl," and the like mean an alkyl, alkenyl, or alkynyl moiety, as the case may be, substituted with an aryl, heterocycloaliphatic, biaryl, etc., moiety, as the case may be, with the open (unsatisfied) valence at the alkyl, alkenyl, or alkynyl moiety, for example as in benzyl, phenethyl, N-imidazoylethyl, N-morpholinoethyl, and the like. Conversely, "alkylaryl," "alkenylcycloalkyl," and the like mean an aryl, cycloalkyl, etc., moiety, as the case may be, substituted with an alkyl, alkenyl, etc., moiety, as the case may be, for example as in methylphenyl(tolyl) or allylcyclohexyl. "Hydroxyalkyl," "haloalkyl," "alkylaryl," "cyanoaryl," and the like mean an alkyl, aryl, etc., moiety, as the case may be, substituted with one or more of the identified substituent (hydroxyl, halo, etc., as the case may be).

For example, permissible substituents include, but are not limited to, alkyl (especially methyl or ethyl), alkenyl (especially allyl), alkynyl, aryl, heteroaryl, cycloaliphatic, heterocycloaliphatic, halo (especially fluoro), haloalkyl (especially trifluoromethyl), hydroxyl, hydroxyalkyl (especially hydroxyethyl), cyano, nitro, alkoxy, —O (hydroxyalkyl), —O (haloalkyl) (especially —OCF$_3$), —O (cycloalkyl), —O (heterocycloalkyl), —O (aryl), alkylthio, arylthio, =O, =NH, =N(alkyl), =NOH, =NO(alkyl), —C(=O)(alkyl), —C(=O)H, —CO$_2$H, —C(=O)NHOH, —C(=O)O (alkyl), —C(=O)O(hydroxyalkyl), —C(=O)NH$_2$, —C(=O)NH(alkyl), —C(=O)N(alkyl)$_2$, —OC(=O) (alkyl), —OC(=O)(hydroxyalkyl), —OC(=O)O(alkyl), —OC(=O)O(hydroxyalkyl), —OC(=O)NH$_2$, —OC(=O)NH(alkyl), —OC(=O)N(alkyl)$_2$, azido, —NH$_2$, —NH (alkyl), —N(alkyl)$_2$, —NH(aryl), —NH(hydroxyalkyl), —NHC(=O)(alkyl), —NHC(=O)H, —NHC(=O)NH$_2$, —NHC(=O)NH(alkyl), —NHC(=O)N(alkyl)$_2$, —NHC (=NH)NH$_2$, —OSO$_2$(alkyl), —SH, —S(alkyl), —S(aryl), —S(cycloalkyl), —S(=O)alkyl, —SO$_2$(alkyl), —SO$_2$NH$_2$, —SO$_2$NH(alkyl), —SO$_2$N(alkyl)$_2$, and the like.

Where the moiety being substituted is an aliphatic moiety, preferred substituents are aryl, heteroaryl, cycloaliphatic, heterocycloaliphatic, halo, hydroxyl, cyano, nitro, alkoxy, —O (hydroxyalkyl), —O (haloalkyl), —O (cycloalkyl), —O (heterocycloalkyl), —O (aryl), alkylthio, arylthio, =O, =NH, =N(alkyl), =NOH, =NO(alkyl), —CO$_2$H, —C(=O)NHOH, —C(=O)O(alkyl), —C(=O)O(hydroxyalkyl), —C(=O)NH$_2$, —C(=O)NH(alkyl), —C(=O)N(alkyl)$_2$, —OC(=O)(alkyl), —OC(=O)(hydroxyalkyl), —OC(=O)O(alkyl), —OC(=O)O(hydroxyalkyl), —OC(=O)NH$_2$, —OC(=O)NH(alkyl), —OC(=O)N(alkyl)$_2$, azido, —NH$_2$, —NH(alkyl), —N(alkyl)$_2$, —NH (aryl), —NH(hydroxyalkyl), —NHC(=O)(alkyl), —NHC (=O)H, —NHC(=O)NH$_2$, —NHC(=O)NH(alkyl), —NHC(=O)N(alkyl)$_2$, —NHC(=NH)NH$_2$, —OSO$_2$ (alkyl), —SH, —S(alkyl), —S(aryl), —S(=O)alkyl, —S(cycloalkyl), —SO$_2$(alkyl), —SO$_2$NH$_2$, —SO$_2$NH (alkyl), and —SO$_2$N(alkyl)$_2$. More preferred substituents are halo, hydroxyl, cyano, nitro, alkoxy, —O (aryl), =O, =NOH, =NO(alkyl), —OC(=O)(alkyl), —OC(=O)O (alkyl), —OC(=O)NH$_2$, —OC(=O)NH(alkyl), —OC (=O)N(alkyl)$_2$, azido, —NH$_2$, —NH(alkyl), —N(alkyl)$_2$, —NH(aryl), —NHC(=O)(alkyl), —NHC(=O)H, —NHC (=O)NH$_2$, —NHC(=O)NH(alkyl), —NHC(=O)N (alkyl)$_2$, and —NHC(=NH)NH$_2$. Especially preferred are phenyl, cyano, halo, hydroxyl, nitro, $C_1$-$C_4$alkyoxy, O($C_2$-$C_4$ alkylene)OH, and O($C_2$-$C_4$ alkylene)halo.

Where the moiety being substituted is a cycloaliphatic, heterocycloaliphatic, aryl, or heteroaryl moiety, preferred substituents are alkyl, alkenyl, alkynyl, halo, haloalkyl, hydroxyl, hydroxyalkyl, cyano, nitro, alkoxy, —O (hydroxyalkyl), —O (haloalkyl), —O (aryl), —O (cycloalkyl), —O (heterocycloalkyl), alkylthio, arylthio, —C(=O) (alkyl), —C(=O)H, —CO$_2$H, —C(=O)NHOH, —C(=O) O(alkyl), —C(=O)O(hydroxyalkyl), —C(=O)NH$_2$, —C(=O)NH(alkyl), —C(=O)N(alkyl)$_2$, —OC(=O) (alkyl), —OC(=O)(hydroxyalkyl), —OC(=O)O(alkyl), —OC(=O)O(hydroxyalkyl), —OC(=O)NH$_2$, —OC(=O) NH(alkyl), —OC(=O)N(alkyl)$_2$, azido, —NH$_2$, —NH (alkyl), —N(alkyl)$_2$, —NH(aryl), —NH(hydroxyalkyl), —NHC(=O)(alkyl), —NHC(=O)H, —NHC(=O)NH$_2$, —NHC(=O)NH(alkyl), —NHC(=O)N(alkyl)$_2$, —NHC (=NH)NH$_2$, —OSO$_2$(alkyl), —SH, —S(alkyl), —S(aryl), —S(cycloalkyl), —S(=O)alkyl, —SO$_2$(alkyl), —SO$_2$NH$_2$, —SO$_2$NH(alkyl), and —SO$_2$N(alkyl)$_2$. More preferred substituents are alkyl, alkenyl, halo, haloalkyl, hydroxyl, hydroxyalkyl, cyano, nitro, alkoxy, —O (hydroxyalkyl), —C(=O)(alkyl), —C(=O)H, —CO$_2$H, —C(=O)NHOH, —C(=O)O(alkyl), —C(=O)O(hydroxyalkyl), —C(=O) NH$_2$, —C(=O)NH(alkyl), —C(=O)N(alkyl)$_2$, —OC(=O) (alkyl), —OC(=O)(hydroxyalkyl), —OC(=O)O(alkyl), —OC(=O)O(hydroxyalkyl), —OC(=O)NH$_2$, —OC(=O) NH(alkyl), —OC(=O)N(alkyl)$_2$, —NH$_2$, —NH(alkyl), —N(alkyl)$_2$, —NH(aryl), —NHC(=O)(alkyl), —NHC (=O)H, —NHC(=O)NH$_2$, —NHC(=O)NH(alkyl), —NHC(=O)N(alkyl)$_2$, and —NHC(=NH)NH$_2$. Especially preferred are $C_1$-$C_4$ alkyl, cyano, nitro, halo, and $C_1$-$C_4$alkoxy.

Where a range is stated, as in "$C_1$-$C_5$ alkyl" or "5 to 10%," such range includes the end points of the range, as in $C_1$ and $C_5$ in the first instance and 5% and 10% in the second instance.

Unless particular stereoisomers are specifically indicated (e.g., by a bolded or dashed bond at a relevant stereocenter in a structural formula, by depiction of a double bond as having E or Z configuration in a structural formula, or by use stereochemistry-designating nomenclature), all stereoisomers are included within the scope of the invention, as pure compounds as well as mixtures thereof. Unless otherwise indicated, individual enantiomers, diastereomers, geometrical isomers, and combinations and mixtures thereof are all encompassed by this invention.

Those skilled in the art will appreciate that compounds may have tautomeric forms (e.g., keto and enol forms), resonance forms, and zwitterionic forms that are equivalent to those depicted in the structural formulae used herein and that the structural formulae encompass such tautomeric, resonance, or zwitterionic forms.

"Pharmaceutically acceptable ester" means an ester that hydrolyzes in vivo (for example in the human body) to produce the parent compound or a salt thereof or has per se activity similar to that of the parent compound. Suitable esters include $C_1$-$C_5$ alkyl, $C_2$-$C_5$ alkenyl or $C_2$-$C_5$ alkynyl esters, especially methyl, ethyl or n-propyl.

"Pharmaceutically acceptable salt" means a salt of a compound suitable for pharmaceutical formulation. Where a compound has one or more basic groups, the salt can be an acid addition salt, such as a sulfate, hydrobromide, tartrate, mesylate, maleate, citrate, phosphate, acetate, pamoate (embonate), hydroiodide, nitrate, hydrochloride, lactate, methylsulfate, fumarate, benzoate, succinate, mesylate, lactobionate, suberate, tosylate, and the like. Where a compound has one or more acidic groups, the salt can be a salt such as a calcium salt, potassium salt, magnesium salt, meglumine salt, ammonium salt, zinc salt, piperazine salt, tromethamine salt, lithium salt, choline salt, diethylamine salt, 4-phenyl-cyclohexylamine salt, benzathine salt, sodium salt, tetramethylammonium salt, and the like. Polymorphic crystalline forms and solvates are also encompassed within the scope of this invention.

In the formulae of this specification, a wavy line transverse to a bond denotes a covalent attachment site. For instance, a statement that R is

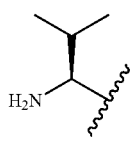

in the formula

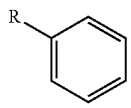

refers to

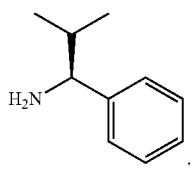

In the formulae of this specification, a bond traversing a phenyl ring between two carbons thereof means that the group attached to the bond may be located at any of the ortho, meta, or para positions of the phenyl ring. By way of illustration, the formula

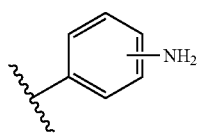

represents

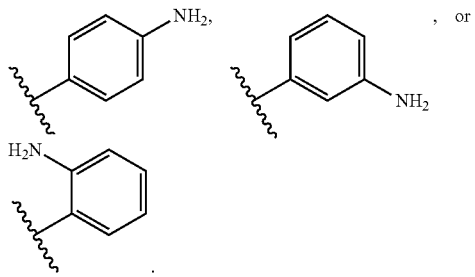

Analogs

In one embodiment of tubulysin analogs according to formula (I)

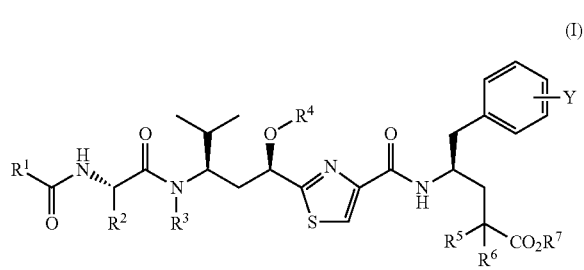

$R^1$ preferably is

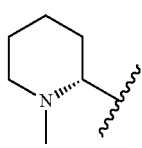

In another preferred embodiment of analogs according to formula (I), $R^1$ is

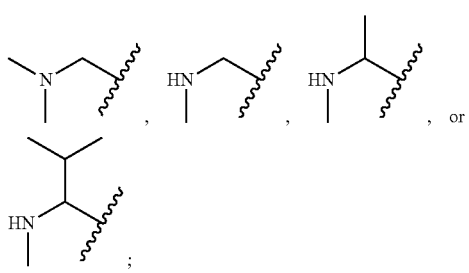

more preferably

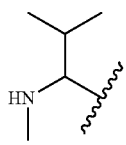

Preferably one of $R^{3a}$ and Y is $NH_2$ in formula (I) when $R^1$ is

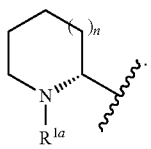

Also in formula (I), preferred groups $N(R^{4a})(R^{4b})$ are:

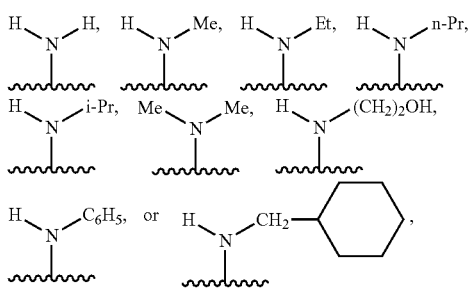

with it being especially preferred that one of $R^{4a}$ and $R^{4b}$ is H and the other is Me. In other preferred embodiments, $R^{4a}$ and $R^{4b}$ are both H or both Me, or one of $R^{4a}$ and $R^{4b}$ is H and the other is $C_6H_5$. Preferably, W is O.

In another preferred embodiment of compounds according to formula (I), $R^5$ and $R^6$ are each Me.

In the definitions of $R^2$ and $R^3$ in formula (I), where a group is defined as being either unsubstituted or substituted, it preferably is unsubstituted.

The synthesis of tubulysin analogs with various groups at the $R^3$, $R^4$, $R^7$, and Y positions of formula (I) is taught by Cheng et al. 2013 and Cong et al. 2014, the disclosures of which are incorporated herein by reference. The techniques disclosed there for the synthesis of structural variants at those positions are applicable to the compounds of this invention, mutatis mutandis.

In one preferred embodiment, a compound of formula (I) has a structure represented by formula (Ia)

(Ia)

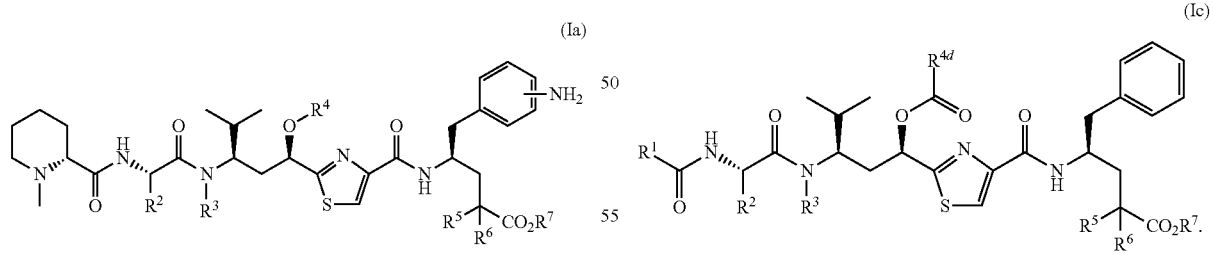

wherein $R^2$ is Me, Et, $CH_2CH_2CH_3$, $CH(Me)_2$, $CH(Et)_2$, or

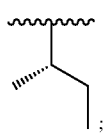

$R^3$ is H, $C_1$-$C_5$ alkyl, $C_1$-$C_5$ alkenyl, $C_1$-$C_5$ alkynyl, $CH_2OC(=O)C_1$-$C_5$ alkyl, $CH_2OC(=O)C_1$-$C_5$ alkenyl, or $CH_2OC(=O)C_1$-$C_5$ alkynyl; and $R^4$, $R^5$, $R^6$ and $R^7$ are as defined in respect formula (I).

A preferred compound according to formula (Ia) has a structure represented by formula (Ia'):

(Ia')

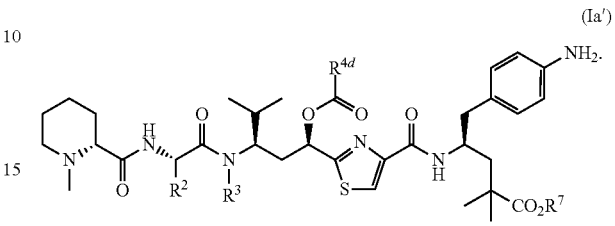

Another preferred compound according to formula (Ia) has a structure represented by formula (Ib'):

(Ib')

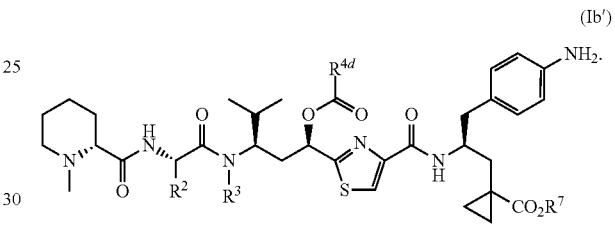

In formulae (Ia') and (Ib'), $R^2$ is $CH(Me)_2$, $CH(Et)_2$, or

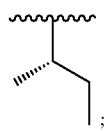

$R^3$ is $C_{1-5}$ alkyl; $R^{4d}$ is Me or NHMe; and $R^7$ is H, Me, or Et.

In yet another preferred embodiment, a compound of formula (I) has a structure represented by formula (Ic):

(Ic)

wherein
$R^1$ is

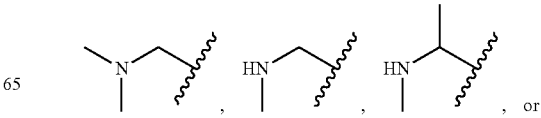

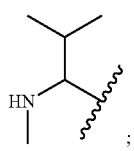

$R^2$ is $CH(Me)_2$, $CH(Et)_2$, or

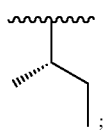

$R^3$ is $C_{1-5}$ alkyl; $R^{4d}$ is Me or NHMe; $R^5$ and $R^6$ are each Me or combine with the carbon to which they are bonded to form a cyclopropyl ring; and $R^7$ is H, Me, or Et. Preferably, $R^5$ and $R^6$ are each Me and $R^1$ is

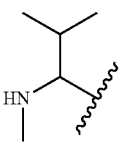

Specific examples of compounds of this invention wherein, in formula (I), $R^5$ and $R^6$ are both methyl and $R^1$ is

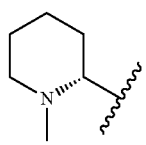 [SMILES: *[C@H]1CCCCN1C]

are shown following:

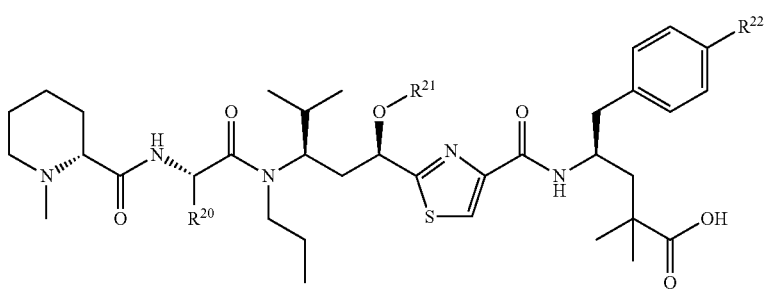

| Compound | $R^{20}$ | $R^{21}$ | $R^{22}$ |
|---|---|---|---|
| (Ia-1) | ![sec-butyl] | ![acetyl] | $NH_2$ |
| (Ia-2) | ![sec-butyl] | ![NHMe amide] | $NH_2$ |
| (Ia-3) | ![isobutyl] | ![acetyl] | $NH_2$ |
| (Ia-4) | ![3-pentyl] | ![acetyl] | $NH_2$ |

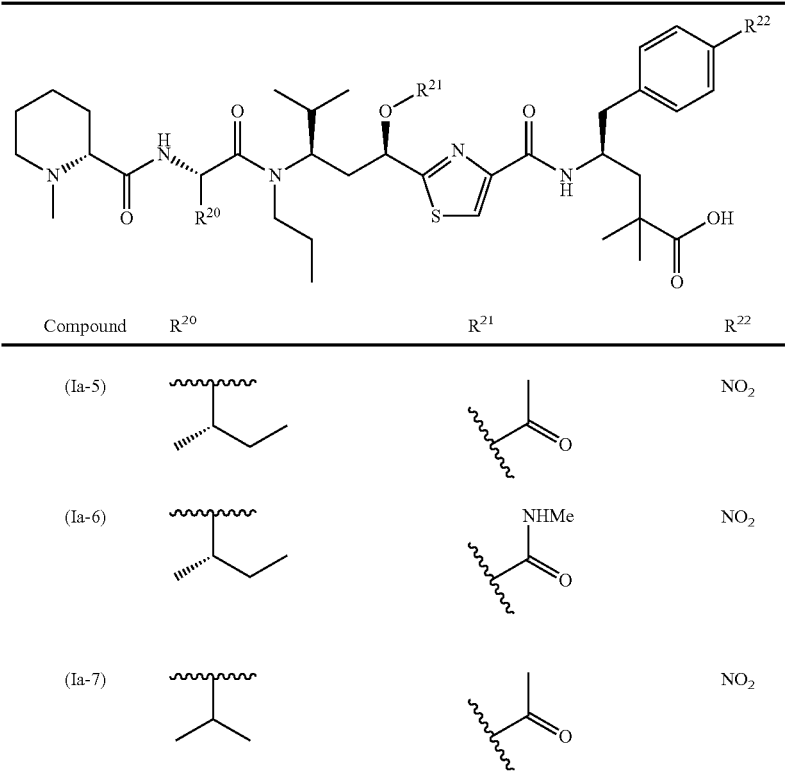

| Compound | $R^{20}$ | $R^{21}$ | $R^{22}$ |
|---|---|---|---|
| (Ia-5) | sec-butyl | acetyl | $NO_2$ |
| (Ia-6) | sec-butyl | N-methylcarbamoyl | $NO_2$ |
| (Ia-7) | isobutyl | acetyl | $NO_2$ |

Specific examples of compounds of this invention wherein, in formula (I), $R^5$ and $R^6$ combine with the carbon to which they are bonded to form a cyclopropyl ring and $R^1$ is Specific examples of compounds of this invention wherein, in formula (I), $R^5$ and $R^6$ are both Me and $R^1$ is

are shown following:

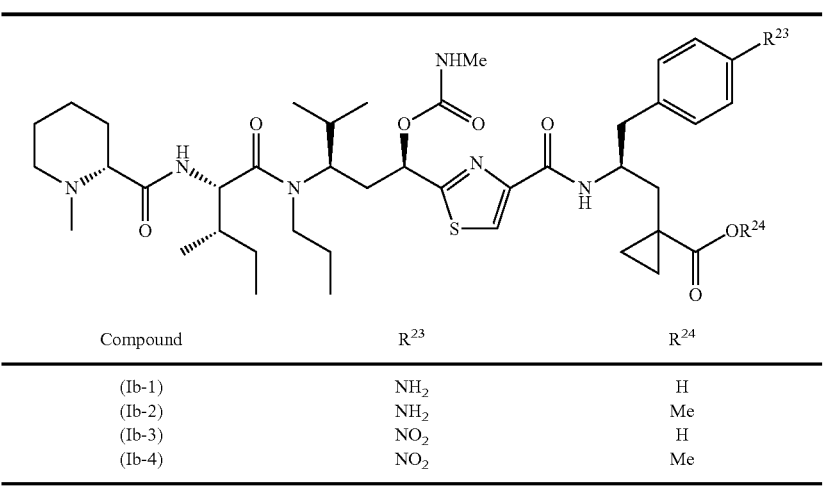

| Compound | $R^{23}$ | $R^{24}$ |
|---|---|---|
| (Ib-1) | $NH_2$ | H |
| (Ib-2) | $NH_2$ | Me |
| (Ib-3) | $NO_2$ | H |
| (Ib-4) | $NO_2$ | Me | are shown following:

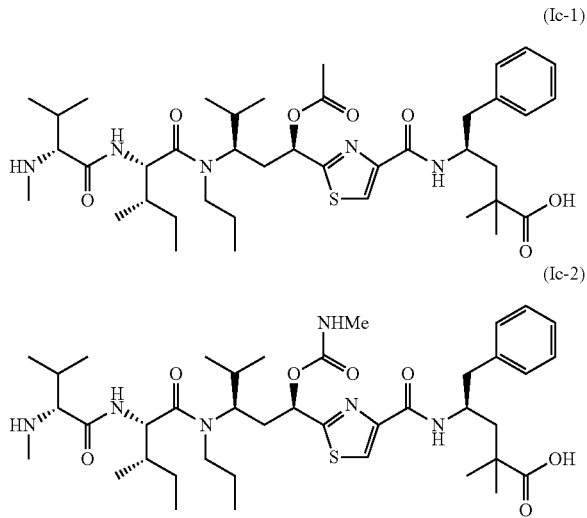

(Ic-1)

(Ic-2)

Conjugates
General

Optionally, compounds of this invention can be conjugated to a targeting moiety that specifically or preferentially binds to a chemical entity on a cancer cell. Preferably, the targeting moiety is an antibody or antigen binding portion thereof and the chemical entity is a tumor associated antigen. For a review on the mechanism of action and use of ADCs in cancer therapy, see Schrama et al. 2006.

Thus, another embodiment of this invention is a conjugate comprising cytotoxic compound according to this invention and a ligand, represented by formula (II)

(II)

where Z is a ligand, D is a tubulysin analog of this invention, and $-(X^D)_a C(X^Z)_b-$ are collectively referred to as a "linker moiety" or "linker" because they link Z and D. Within the linker, C is a cleavable group designed to be cleaved at or near the site of intended biological action of compound D; $X^D$ and $X^Z$ are referred to as spacer moieties (or "spacers") because they space apart D and C and C and Z, respectively; subscripts a, b, and c are independently 0 or 1 (that is, the presence of $X^D$, $X^Z$ and C are optional). Subscript m is 1, 2, 3, 4, 5, 6, 7, 8, 9, or 10 (preferably 1, 2, 3, or 4). D, $X^D$, C, $X^Z$ and Z are more fully described hereinbelow.

Ligand Z—for example an antibody—performs a targeting function. By binding to a target tissue or cell where its antigen or receptor is located, ligand Z directs the conjugate there. (When ligand Z is an antibody, the conjugate is sometimes referred to as antibody-drug conjugate (ADC) or an immunoconjugate. Preferably, the target tissue or cell is a cancer tissue or cell and the antigen or receptor is a tumor-associated antigen, that is, an antigen that is uniquely expressed by cancerous cells or is overexpressed by cancer cells, compared to non-cancerous cells. Cleavage of group C at the target tissue or cell releases compound D to exert its cytotoxic effect locally. In some instances, the conjugate is internalized into a target cell by endocytosis and cleavage takes place within the target cell. In this manner, precise delivery of compound D is achieved at the site of intended action, reducing the dosage needed. Also, compound D is normally biologically inactive (or significantly less active) in its conjugated state, thereby reducing undesired toxicity against non-target tissue or cells. As anticancer drugs are often highly toxic to cells in general, this is an important consideration.

As reflected by the subscript m, each molecule of ligand Z can conjugate with more than one compound D, depending on the number of sites ligand Z has available for conjugation and the experimental conditions employed. Those skilled in the art will appreciate that, while each individual molecule of ligand Z is conjugated to an integer number of compounds D, a preparation of the conjugate may analyze for a non-integer ratio of compounds D to ligand Z, reflecting a statistical average. This ratio is referred to as the substitution ratio (SR) or, alternatively, the drug-antibody ratio (DAR).

Ligand Z

Preferably, ligand Z is an antibody. For convenience and brevity and not by way of limitation, the detailed subsequent discussion herein about the conjugation of ligand Z is written in the context of its being an antibody, but those skilled in the art will understand that other types of ligand Z can be conjugated, mutatis mutandis. For example, conjugates with folic acid as the ligand can target cells having the folate receptor on their surfaces (Vlahov et al. 2008; Leamon et al. 2008). For the same reason, the detailed discussion below is primarily written in terms of a 1:1 ratio of antibody Z to analog D (m=1).

Preferably, ligand Z is an antibody against a tumor associated antigen, allowing the selective targeting of cancer cells. Examples of such antigens include: mesothelin, prostate specific membrane antigen (PSMA), CD19, CD22, CD30, CD70, B7H4 (also known as O8E), protein tyrosine kinase 7 (PTK7), glypican-3, RG1, CTLA-4, and CD44. The antibody can be animal (e.g., murine), chimeric, humanized, or, preferably, human. The antibody preferably is monoclonal, especially a monoclonal human antibody. The preparation of human monoclonal antibodies against some of the aforementioned antigens is disclosed in Korman et al., US 2009/0074660 A1 (B7H4); Rao-Naik et al., U.S. Pat. No. 8,097,703 B2 (CD19); King et al., US 2010/0143368 A1 (CD22); Keler et al., U.S. Pat. No. 7,387,776 B2 (2008) (CD30); Terrett et al., U.S. Pat. No. 8,124,738 B2 (CD70); Korman et al., U.S. Pat. No. 6,984,720 B1 (2006) (CTLA-4); Korman et al., U.S. Pat. No. 8,008,449 B2 (2011) (PD-1); Huang et al., US 2009/0297438 A1 and Cardarelli et al., U.S. Pat. No. 7,875,278 B2 (PSMA); Terrett et al., US 2010/0034826 A1 (PTK7); Terrett et al., US 2010/0209432 (A1) (glypican-3); Harkins et al., U.S. Pat. No. 7,335,748 B2(2008) (RG1); Terrett et al., U.S. Pat. No. 8,268,970 B2 (2012) (mesothelin); and Xu et al., US 2010/0092484 A1 (CD44); the disclosures of which are incorporated herein by reference.

Ligand Z can also be an antibody fragment or antibody mimetic, such as an affibody, a domain antibody (dAb), a nanobody, a unibody, a DARPin, an anticalin, a versabody, a duocalin, a lipocalin, or an avimer.

Any one of several different reactive groups on ligand Z can be a conjugation site, including ε-amino groups in lysine residues, pendant carbohydrate moieties, carboxylic acid groups, disulfide groups, and thiol groups. Each type of reactive group represents a trade-off, having some advantages and some disadvantages. For reviews on antibody reactive groups suitable for conjugation, see, e.g., Garnett, *Adv. Drug Delivery Rev.* 53 (2001), 171-216 and Dubowchik and Walker, *Pharmacology & Therapeutics* 83 (1999), 67-123, the disclosures of which are incorporated herein by reference.

In one embodiment, ligand Z is conjugated via a lysine ε-amino group. Most antibodies have multiple lysine ε-amino groups, which can be conjugated via amide, urea, thiourea, or carbamate bonds using techniques known in the art. However, it is difficult to control which and how many ε-amino groups react, leading to potential batch-to-batch variability in conjugate preparations. Also, conjugation may cause neutralization of a protonated ε-amino group important for maintaining the antibody's native conformation or may take place at a lysine near or at the antigen binding site, neither being a desirable occurrence.

In another embodiment, ligand Z can be conjugated via a carbohydrate side chain, as many antibodies are glycosylated. The carbohydrate side chain can be oxidized with periodate to generate aldehyde groups, which in turn can be reacted with amines to form an imine group, such as in a semicarbazone, oxime, or hydrazone. If desired, the imine group can be converted to a more stable amine group by reduction with sodium cyanoborohydride. For additional disclosures on conjugation via carbohydrate side chains, see, e.g., Rodwell et al., *Proc. Nat'l Acad. Sci. USA* 83, 2632-2636 (1986); the disclosure of which is incorporated herein by reference. As with lysine ε-amino groups, there are concerns regarding reproducibility of the location of the conjugation site(s) and stoichiometry.

In yet another embodiment, ligand Z can be conjugated via a carboxylic acid group. In one embodiment, a terminal carboxylic acid group is functionalized to generate a carbohydrazide, which is then reacted with an aldehyde-bearing conjugation moiety. See Fisch et al., *Bioconjugate Chemistry* 1992, 3, 147-153.

In yet another embodiment, antibody Z can be conjugated via a disulfide group bridging a cysteine residue on antibody Z and a sulfur on the other portion of the conjugate. Some antibodies lack free thiol (sulfhydryl) groups but have disulfide groups, for example in the hinge region. In such case, free thiol groups can be generated by reduction of native disulfide groups. The thiol groups so generated can then be used for conjugation. See, e.g., Packard et al., *Biochemistry* 1986, 25, 3548-3552; King et al., *Cancer Res.* 54, 6176-6185 (1994); and Doronina et al., *Nature Biotechnol.* 21(7), 778-784 (2003); the disclosures of which are incorporated herein by reference. Again, there are concerns regarding conjugation site location and stoichiometry and the possible disruption of antibody native conformation.

A number of methods are known for introducing free thiol groups into antibodies without breaking native disulfide bonds, which methods can be practiced with a ligand Z of this invention. Depending on the method employed, it may be possible to introduce a predictable number of free sulfhydryls at predetermined locations. In one approach, mutated antibodies are prepared in which a cysteine is substituted for another amino acid. See, for example, Eigenbrot et al., U.S. Pat. No. 7,521,541 B2 (2009); Chilkoti et al., *Bioconjugate Chem.* 1994, 5, 504-507; Urnovitz et al., U.S. Pat. No. 4,698,420 (1987); Stimmel et al., *J. Biol. Chem.*, 275 (39), 30445-30450 (2000); Bam et al., U.S. Pat. No. 7,311,902 B2 (2007); Kuan et al., *J. Biol. Chem.*, 269 (10), 7610-7618 (1994); Poon et al., *J. Biol. Chem.*, 270 (15), 8571-8577 (1995). In another approach, an extra cysteine is added to the C-terminus See, e.g. Cumber et al., *J. Immunol.*, 149, 120-126 (1992); King et al, *Cancer Res.*, 54, 6176-6185 (1994); Li et al., *Bioconjugate Chem.*, 13, 985-995 (2002); Yang et al., *Protein Engineering*, 16, 761-770 (2003); and Olafson et al., *Protein Engineering Design & Selection*, 17, 21-27 (2004). A preferred method for introducing free cysteines is that taught by Liu et al., WO 2009/026274 A1, in which a cysteine bearing amino acid sequence is added to the C-terminus of the heavy chain of an antibody. This method introduces a known number of cysteine residues (one per heavy chain) at a known location awat from the antigen binding site. The disclosures of the documents cited in this paragraph are all incorporated herein by reference.

In yet another embodiment, lysine ε-amino groups can be modified with reagents such as 2-iminothiolane or N-succinimidyl-3-(2-pyridyldithio)propionate (SPDP), converting an ε-amino group into a thiol or disulfide group—creating a cysteine surrogate, as it were. However, this method suffers from the same conjugation location and stoichiometry limitations associated with ε-amino groups proper.

Linker Components

As noted above, the linker portion of a conjugate of this invention comprises up to three elements: a cleavable group C and optional spacers $X^Z$ and $X^D$.

Cleavable group C is a group cleavable under physiological conditions, preferably selected such that it is relatively stable while the conjugate is in general circulation in the blood plasma, but is readily cleaved once the conjugate reaches its site of intended action, that is, near, at, or within the target cell. Preferably, the conjugate is internalized by a target cell upon binding of antibody Z to an antigen displayed on the surface of the target cell. Subsequently, cleavage of group C occurs in a vesicular body of the target cell (an early endosome, a late endosome, or, especially, a lysosome).

In one embodiment, group C is a pH sensitive group. The pH in blood plasma is slightly above neutral, while the pH inside a lysosome is acidic, circa 5. Thus, a group C whose cleavage is acid catalyzed will cleave at a rate several orders of magnitude faster inside a lysosome than in the blood plasma rate. Examples of suitable acid-sensitive groups include cis-aconityl amides and hydrazones, as described in Shen et al., U.S. Pat. No. 4,631,190 (1986); Shen et al., U.S. Pat. No. 5,144,011 (1992); Shen et al., *Biochem. Biophys. Res. Commun.* 102, 1048-1054 (1981) and Yang et al., *Proc. Natl Acad. Sci (USA)*, 85, 1189-1193 (1988); the disclosures of which are incorporated herein by reference.

In another embodiment, group C is a disulfide. Disulfides can be cleaved by a thiol-disulfide exchange mechanism, at a rate dependent on the ambient thiol concentration. As the intracellular concentration of glutathione and other thiols is higher than their serum concentrations, the cleavage rate of a disulfide will be higher intracellularly. Further, the rate of thiol-disulfide exchange can be modulated by adjustment of the steric and electronic characteristics of the disulfide (e.g., an alkyl-aryl disulfide versus an alkyl-alkyl disulfide; substitution on the aryl ring, etc.), enabling the design of disulfide linkages that have enhanced serum stability or a particular cleavage rate. For additional disclosures relating to disulfide cleavable groups in conjugates, see, e.g., Thorpe et al., *Cancer Res.* 48, 6396-6403 (1988); Santi et al., U.S. Pat. No. 7,541,530 B2 (2009); Ng et al., U.S. Pat. No. 6,989,452 B2 (2006); Ng et al., WO 2002/096910 A1; Boyd et al., U.S. Pat. No. 7,691,962 B2; and Sufi et al., US 2010/0145036 A1; the disclosures of which are incorporated herein by reference.

A preferred cleavable group is a peptide that is cleaved selectively by a protease inside the target cell, as opposed to by a protease in the serum. Typically, a cleavable peptide group comprises from 1 to 20 amino acids, preferably from 1 to 6 amino acids, more preferably from 1 to 3 amino acids. The amino acid(s) can be natural and/or non-natural α-amino acids. Natural amino acids are those encoded by the genetic code, as well as amino acids derived therefrom, e.g., hydroxyproline, γ-carboxyglutamate, citrulline, and O-phosphoserine. In this context, the term "amino acid" also includes amino acid analogs and mimetics. Analogs are compounds having the same general $H_2N(R)CHCO_2H$ structure of a natural amino acid, except that the R group is not one found among the natural amino acids. Examples of analogs include homoserine, norleucine, methionine-sulfoxide, and methionine methyl sulfonium. An amino acid mimetic is a compound that has a structure different from the general chemical structure of an α-amino acid but functions in a manner similar to one. The amino acid can be of the "L" stereochemistry of the genetically encoded amino acids, as well as of the enantiomeric "D" stereochemistry.

Preferably, group C contains an amino acid sequence that is a cleavage recognition sequence for a protease. Many cleavage recognition sequences are known in the art. See, e.g., Matayoshi et al. *Science* 247: 954 (1990); Dunn et al. *Meth. Enzymol.* 241: 254 (1994); Seidah et al. *Meth. Enzymol.* 244: 175 (1994); Thornberry, *Meth. Enzymol.* 244: 615 (1994); Weber et al. *Meth. Enzymol.* 244: 595 (1994); Smith et al. *Meth. Enzymol.* 244: 412 (1994); and Bouvier et al. *Meth. Enzymol.* 248: 614 (1995); the disclosures of which are incorporated herein by reference.

For conjugates that are not intended to be internalized by a cell, a group C can be chosen such that it is cleaved by a protease present in the extracellular matrix in the vicinity of the target tissue, e.g., a protease released by nearby dying cells or a tumor-associated protease. Exemplary extracellular tumor-associated proteases are matrix metalloproteases (MMP), thimet oligopeptidase (TOP) and CD10.

For conjugates that are designed to be internalized by a cell, group C preferably comprises an amino acid sequence selected for cleavage by an endosomal or lysosomal protease, especially the latter. Non-limiting examples of such proteases include cathepsins B, C, D, H, L and S, especially cathepsin B. Cathepsin B preferentially cleaves peptides at a sequence -$AA^2$-$AA^1$- where $AA^1$ is a basic or strongly hydrogen bonding amino acid (such as lysine, arginine, or citrulline) and $AA^2$ is a hydrophobic amino acid (such as phenylalanine, valine, alanine, leucine, or isoleucine), for example Val-Cit (where Cit denotes citrulline) or Val-Lys. (Herein, amino acid sequences are written in the N-to-C direction, as in $H_2N$-$AA^2$-$AA^1$-$CO_2H$, unless the context clearly indicates otherwise.) Lys-Val-Ala, Asp-Val-Ala, Val-Ala, Lys-Val-Cit, and Asp-Val-Cit are also substrate peptide motifs for cathpsin B, although in some instances the cleavage rate may be slower. For additional information regarding cathepsin-cleavable groups, see Dubowchik et al., *Biorg. Med. Chem. Lett.* 8, 3341-3346 (1998); Dubowchik et al., *Bioorg. Med. Chem. Lett.,* 8 3347-3352 (1998); and Dubowchik et al., *Bioconjugate Chem.* 13, 855-869 (2002); the disclosures of which are incorporated by reference. Another enzyme that can be utilized for cleaving peptidyl linkers is legumain, a lysosomal cysteine protease that preferentially cleaves at Ala-Ala-Asn.

In one embodiment, Group C is a peptide comprising a two-amino acid sequence -$AA^2$-$AA^1$- wherein $AA^1$ is lysine, arginine, or citrulline and $AA^2$ is phenylalanine, valine, alanine, leucine or isoleucine. In another embodiment, C consists of a sequence of one to three amino acids, selected from the group consisting of Val-Cit, Ala-Val, Val-Ala-Val, Lys-Lys, Ala-Asn-Val, Val-Leu-Lys, Cit-Cit, Val-Lys, Ala-Ala-Asn, Lys, Cit, Ser, and Glu.

The preparation and design of cleavable groups C consisting of a single amino acid is disclosed in Chen et al., US 2010/0113476 A1, the disclosure of which is incorporated herein by reference.

Group C can also be a photocleavable one, for example a nitrobenzyl ether that is cleaved upon exposure to light.

Group C can be bonded directly to antibody Z or analog D; i.e. spacers $X^Z$ and $X^D$, as the case may be, can be absent. For example, if group C is a disulfide, one of the two sulfurs can be a cysteine residue or its surrogate on antibody Z. Or, group C can be a hydrazone bonded to an aldehyde on a carbohydrate side chain of the antibody. Or, group C can be a peptide bond formed with a lysine ε-amino group of antibody Z. In a preferred embodiment, compound D is directly bonded to group C via a peptidyl bond to a carboxyl or amine group in compound D.

When present, spacer $X^Z$ provides spatial separation between group C and antibody Z, least the former sterically interfere with antigen binding by latter or the latter sterically interfere with cleavage of the former. Further, spacer $X^Z$ can be used to confer increased solubility or decreased aggregation properties to conjugates. A spacer $X^Z$ can comprise one or more modular segments, which can be assembled in any number of combinations. Examples of suitable segments for a spacer $X^Z$ are:

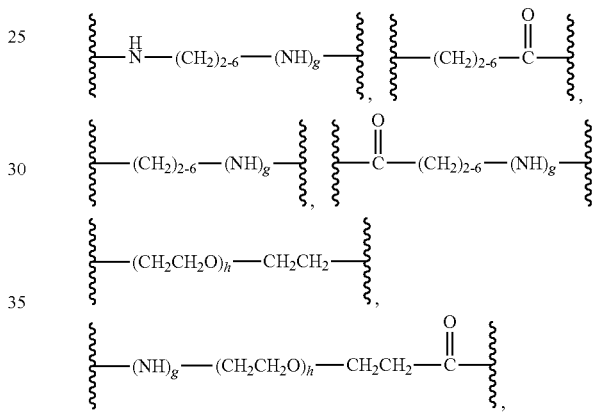

and combinations thereof,
where the subscript g is 0 or 1 and the subscript h is 1 to 24, preferably 2 to 4. These segments can be combined, such as illustrated below:

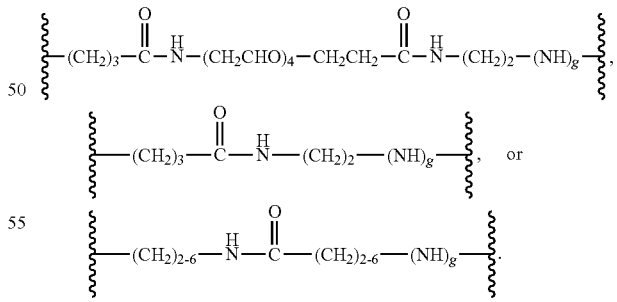

Spacer $X^D$, if present, provides spatial separation between group C and compound D, least the latter interfere sterically or electronically with cleavage of the former. Spacer $X^D$ also can serve to introduce additional molecular mass and chemical functionality into a conjugate. Generally, the additional mass and functionality will affect the serum half-life and other properties of the conjugate. Thus, through judicious selection of spacer groups, the serum half-live of a conjugate can be modulated. Spacer $X^D$ also can be assembled from modular segments, as described above in the context of spacer $X^Z$.

Spacers $X^Z$ and/or $X^D$, where present, preferably provide a linear separation of from 4 to 25 atoms, more preferably from 4 to 20 atoms, between Z and C or D and C, respectively.

The linker can perform other functions in addition to covalently linking the antibody and the drug. For instance, the linker can contain poly(ethylene glycol) (PEG) groups, which enhance solubility either during the performance the conjugation chemistry or in the final ADC product. Where a PEG group is present, it may be incorporated into either spacer $X^Z$ of $X^D$, or both. The number of repeat units in a PEG group can be from 2 to 20, preferably between 4 and 10.

Either spacer $X^Z$ or $X^D$, or both, can comprise a self-immolating moiety. A self-immolating moiety is a moiety that (1) is bonded to group C and either antibody Z or cytotoxin D and (2) has a structure such that cleavage from group C initiates a reaction sequence resulting in the self-immolating moiety disbonding itself from antibody Z or cytotoxin D, as the case may be. In other words, reaction at a site distal from antibody Z or cytotoxin D (cleavage from group C) causes the $X^Z$—Z or the $X^D$-D bond to rupture as well. The presence of a self-immolating moiety is desirable in the case of spacer $X^D$ because, if, after cleavage of the conjugate, spacer $X^D$ or a portion thereof were to remain attached to cytotoxin D, the biological activity of the latter may be impaired. The use of a self-immolating moiety is especially desirable where cleavable group C is a polypeptide, in which instance the self-immolating moiety typically is located adjacent thereto.

Exemplary self-immolating moieties (i)-(v) bonded to a hydroxyl or amino group on a partner molecule D are shown below:

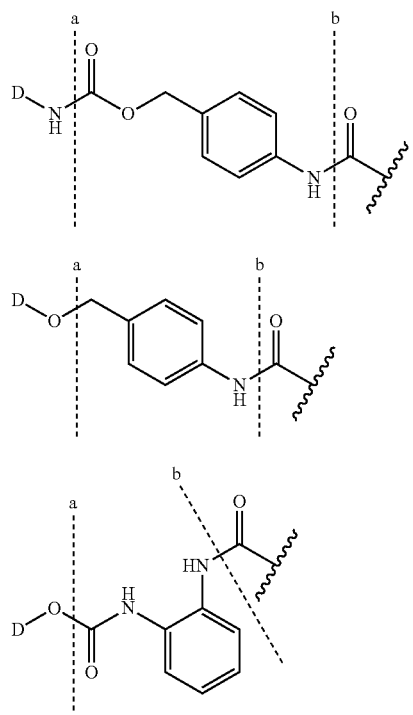

The self-immolating moiety is the structure between dotted lines a and b, with adjacent structural features shown to provide context. Self-immolating moieties (i) and (v) are bonded to a compound D-NH$_2$ (i.e., compound D is conjugated via an amino group), while self-immolating moieties (ii), (iii), and (iv) are bonded to a compound D-OH (i.e., compound D is conjugated via a hydroxyl or carboxyl group). Cleavage of the amide bond at dotted line b (e.g., by a peptidase) releases the amide nitrogen as an amine nitrogen, initiating a reaction sequence that results in the cleavage of the bond at dotted line a and the consequent release of D-OH or D-NH$_2$, as the case may be. Alternatively, the cleavage that triggers the self-immolating reaction can be by a different type of enzyme, for example by a β-glucuronidase, as in the instance of structure (vi). For additional disclosures regarding self-immolating moieties, see Carl et al., *J. Med. Chem.*, 24 (3), 479-480 (1981); Carl et al., WO 81/01145 (1981); Dubowchik et al., *Pharmacology & Therapeutics*, 83, 67-123 (1999); Firestone et al., U.S. Pat. No. 6,214,345 B1 (2001); Toki et al., *J. Org. Chem.* 67, 1866-1872 (2002); Doronina et al., *Nature Biotechnology* 21 (7), 778-784 (2003) (erratum, p. 941); Boyd et al., U.S. Pat. No. 7,691,962 B2; Boyd et al., US 2008/0279868 A1; Sufi et al., WO 2008/083312 A2; Feng, U.S. Pat. No. 7,375,078 B2; Jeffrey et al., U.S. Pat. No. 8,039,273; and Senter et al., US 2003/0096743 A1; the disclosures of which are incorporated by reference. A preferred self-immolating group is p-aminobenzyl oxycarbonyl (PABC) group, as shown in structure (i).

In another embodiment, an antibody targeting moiety and the cytotoxic compound D are linked by a non-cleavable linker, i.e., element C is absent. Degradation of the antibody eventually reduces the linker to a small appended moiety that does not interfere with the biological activity of cytotoxic compound D.

Conjugation Techniques

Conjugates of this invention preferably are made by first preparing a compound comprising an analog of this invention (represented by D in the formulae below) and linker $(X^D)_a(C)_c(X^Z)_b$ (where $X^D$, C, $X^Z$, a, b, and c are as defined for formula (II)) to form an analog-linker composition represented by formula (III):

where $R^{31}$ is a functional group suitable for reacting with a complementary functional group on antibody Z to form the conjugate. Examples of suitable groups $R^{31}$ include amino, azide, cyclooctyne,

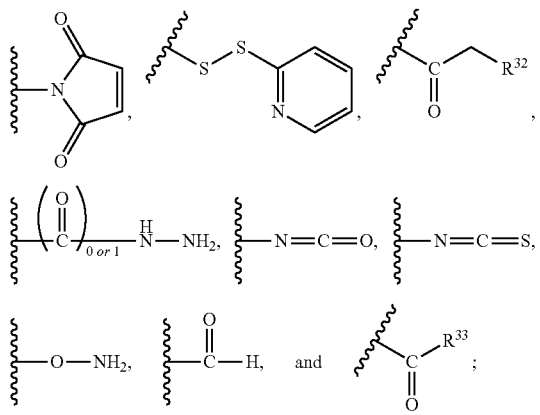

where $R^{32}$ is Cl, Br, F, mesylate, or tosylate and $R^{33}$ is Cl, Br, I, F, OH, —O—N-succinimidyl, —O-(4-nitrophenyl), —O-pentafluorophenyl, or —O-tetrafluorophenyl. Chemistry generally usable for the preparation of suitable moieties $D-(X^D)_aC(X^Z)_b—R^{31}$ is disclosed in Ng et al., U.S. Pat. No. 7,087,600 B2 (2006); Ng et al., U.S. Pat. No. 6,989,452 B2 (2006); Ng et al., U.S. Pat. No. 7,129,261 B2 (2006); Ng et al., WO 02/096910 A1; Boyd et al., U.S. Pat. No. 7,691,962 B2; Chen et al., U.S. Pat. No. 7,517,903 B2 (2009); Gangwar et al., U.S. Pat. No. 7,714,016 B2 (2010); Boyd et al., US 2008/0279868 A1; Gangwar et al., U.S. Pat. No. 7,847,105 B2 (2010); Gangwar et al., U.S. Pat. No. 7,968,586 B2 (2011); Sufi et al., US 2010/0145036 A1; and Chen et al., US 2010/0113476 A1; the disclosures of which are incorporated herein by reference.

Preferably reactive functional group —$R^{31}$ is —$NH_2$, —OH, —$CO_2H$, —SH, maleimido, cyclooctyne, azido (—$N_3$), hydroxylamino (—$ONH_2$) or N-hydroxysuccinimido. Especially preferred functional groups —$R^{31}$ are:

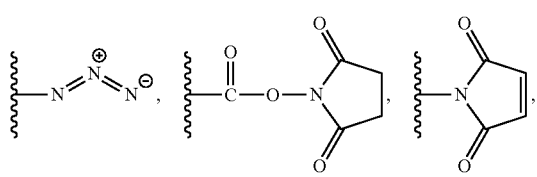

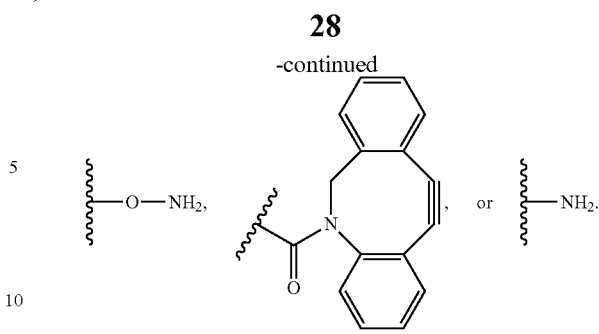

An —OH group can be esterified with a carboxy group on the antibody, for example, on an aspartic or glutamic acid side chain.

A —$CO_2H$ group can be esterified with a —OH group or amidated with an amino group (for example on a lysine side chain) on the antibody.

An N-hydroxysuccinimide group is functionally an activated carboxyl group and can conveniently be amidated by reaction with an amino group (e.g., from lysine).

A maleimide group can be conjugated with an —SH group on the antibody (e.g., from cysteine or from the chemical modification of the antibody to introduce a sulfhydryl functionality), in a Michael addition reaction.

Various techniques can be introducing an —SH group into an antibody. In a preferred one, an ε-amino group in the side chain of a lysine residue in the antibody is reacted with 2-iminothiolane to introduce a free thiol (—SH) group. The thiol group can react with a maleimide or other nucleophile acceptor group to effect conjugation:

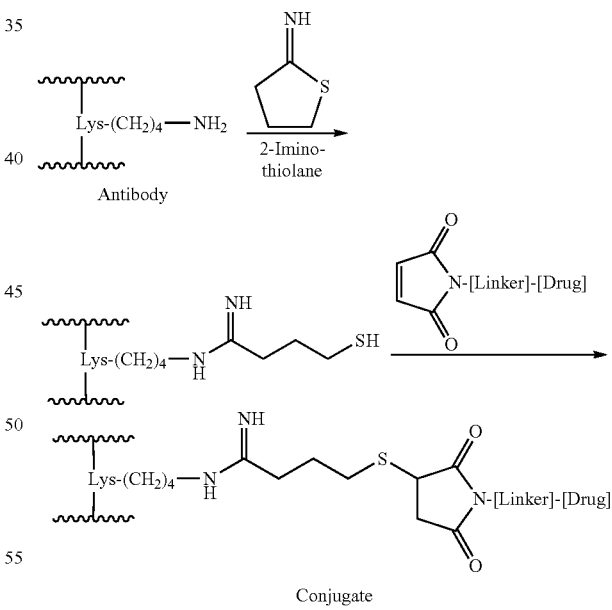

Conjugate

Typically, a thiolation level of two to three thiols per antibody is achieved. For a representative procedure, see Cong et al. 2014, the disclosure of which is incorporated herein by reference. Thus, in one embodiment, an antibody for conjugation to a tubulysin analog of this invention has one or more lysine residues (preferably two or three) modified by reaction with iminothiolane.

An —SH group can also be used for conjugation where the antibody has been modified to introduce a maleimide group thereto, in a Michael addition reaction that is the "mirror image" of that described above. Antibodies can be modified to have maleimide groups with N-succinimidyl 4-(maleimidomethyl)-cyclohexanecarboxylate (SMCC) or its sulfonated variant sulfo-SMCC, both reagents being available from Sigma-Aldrich.

An alternative conjugation technique employs copper-free "click chemistry," in which an azide group adds across the strained alkyne bond of a cyclooctyne to form an 1,2,3-triazole ring. See, e.g., Agard et al., *J. Amer. Chem. Soc.* 2004, 126, 15046; Best, *Biochemistry* 2009, 48, 6571, the disclosures of which are incorporated herein by reference. The azide can be located on the antibody and the cyclooctyne on the drug moiety, or vice-versa. A preferred cyclooctyne group is dibenzocyclooctyne (DIBO). Various reagents having a DIBO group are available from Invitrogen/Molecular Probes, Eugene, Oreg. The reaction below illustrates click chemistry conjugation for the instance in which the DIBO group is attached to the antibody (Ab):

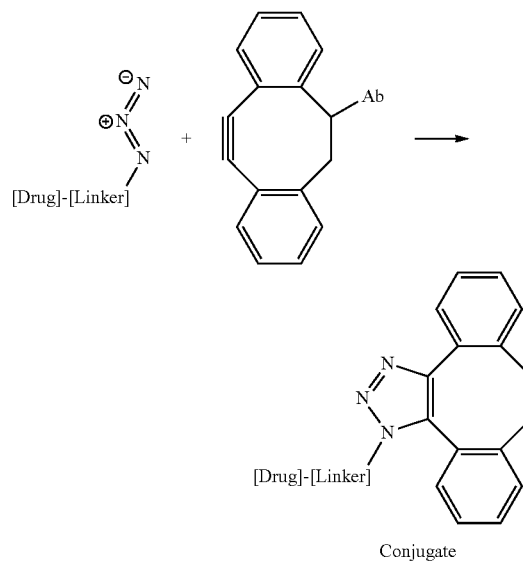

Conjugate

Yet another conjugation technique involves introducing a non-natural amino acid into an antibody, with the non-natural amino acid providing a functionality for conjugation with a reactive functional group in the drug moiety. For instance, the non-natural amino acid p-acetylphenylalanine can be incorporated into an antibody or other polypeptide, as taught in Tian et al., WO 2008/030612 A2 (2008). The ketone group in p-acetylphenylalanine can be a conjugation site via the formation of an oxime with a hydroxylamino group on the linker-drug moiety. Alternatively, the non-natural amino acid p-azidophenylalanine can be incorporated into an antibody to provide an azide functional group for conjugation via click chemistry, as discussed above. Non-natural amino acids can also be incorporated into an antibody or other polypeptide using cell-free methods, as taught in Goerke et al., US 2010/0093024 A1 (2010) and Goerke et al., *Biotechnol. Bioeng.* 2009, 102 (2), 400-416. The foregoing disclosures are incorporated herein by reference. Thus, in one embodiment, an antibody that is used for making a conjugate with a tubulysin of this invention has one or more amino acids replaced by a non-natural amino acid, which preferably is p-acetylphenylalanine or p-azidophenylalanine, more preferably p-acetylphenylalanine.

Still another conjugation technique uses the enzyme transglutaminase (preferably bacterial transglutaminase or BTG), per Jeger et al., *Angew. Chem. Int. Ed.* 2010, 49, 9995. BTG forms an amide bond between the side chain carboxamide of a glutamine (the amine acceptor) and an alkyleneamino group (the amine donor), which can be, for example, the ε-amino group of a lysine or a 5-amino-n-pentyl group. In a typical conjugation reaction, the glutamine residue is located on the antibody, while the alkyleneamino group is located on the linker-drug moiety, as shown below:

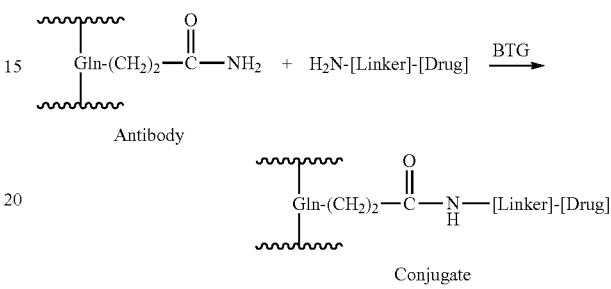

The positioning of a glutamine residue on a polypeptide chain has a large effect on its susceptibility to BTG mediated transamidation. None of the glutamine residues on an antibody are normally BTG substrates. However, if the antibody is deglycosylated—the glycosylation site being asparagine 297 (N297)-nearby glutamine 295 (Q295) is rendered BTG susceptible. An antibody can be deglycosylated enzymatically by treatment with PNGase F (Peptide-N-Glycosidase F). Alternatively, an antibody can be synthesized glycoside free by introducing an N297A mutation in the constant region, to eliminate the N297 glycosylation site. Further, it has been shown that an N297Q substitution in an antibody not only eliminates glycosylation, but also introduces a second glutamine residue (at position 297) that too is an amine acceptor. Thus, in one embodiment, an antibody that is conjugated to a tubulysin analog of this invention is deglycosylated. In another embodiment, the antibody has an N297Q substitution. Those skilled in the art will appreciate that deglycosylation by post-synthesis modification or by introducing an N297A mutation generates two BTG-reactive glutamine residues per antibody (one per heavy chain, at position 295), while an antibody with an N297Q substitution will have four BTG-reactive glutamine residues (two per heavy chain, at positions 295 and 297).

Conjugation can also be effected using the enzyme Sortase A, as taught in Levary et al., *PLoS One* 2011, 6(4), e18342; Proft, *Biotechnol. Lett.* 2010, 32, 1-10; Ploegh et al., WO 2010/087994 A2 (2010); and Mao et al., WO 2005/051976 A2 (2005). The Sortase A recognition motif (typically LPXTG, where X is any natural amino acid) may be located on the ligand Z and the nucleophilic acceptor motif (typically GGG) may be the group $R^{31}$ in formula (III), or vice-versa.

An antibody also can be adapted for conjugation by modifying its glycosyl group to introduce a keto group that serves as a conjugation site by oxime formation, as taught by Zhu et al., *mAbs* 2014, 6, 1. In another glycoengineering variation, an antibody's glycosyl group can be modified to introduce an azide group for conjugation by "click chemistry." See Huang et al., *J. Am. Chem. Soc.* 2012, 134, 12308 and Wang, U.S. Pat. No. 8,900,826 B2 (2014) and U.S. Pat. No. 7,807,405 B2 (2010).

Yet another conjugation technique can be generally referred to as disulfide bridging: the disulfide bonds in an antibody are cleaved, creating a pair of thiol (—SH) groups. The antibody is then treated with a drug-linker compound that contains two thiol-reactive sites. Reaction of the thiol groups with the two sites effects a re-bridging that re-creates, in a fashion, the original disulfide bridge, thus preserving the antibody tertiary structure and attaching a drug-linker moiety. See, e.g., Burt et al., WO 2013/190292 A2 (2013) and Jackson et al., US 2013/0224228 A1 (2013).

Analog-Linker Compounds

Generally, an ADC of a tubulysin analog of this invention comprises a linker attached at one end thereof to an amine group located at a modified Mep, Tuv, or Tup subunit (preferably a modified Mep or Tup subunit). The linker is attached at the other end thereof to the antibody. Reflecting the diversity of conjugation techniques available, the tubulysin analogs of this invention can be elaborated into many different tubulysin analog-linker compounds suitable for conjugation to an antibody.

A preferred tubulysin analog-linker compound has a structure represented by formula (IIIa):

$R^{4d}$ is Me or NHMe;

$R^5$ and $R^6$ are each Me or combine with the carbon to which they are bonded to form a cyclopropyl ring (preferably both are Me);

$R^7$ is H, Me, or Et;

T is a self-immolating group;

t is 0 or 1;

$AA^a$ and each $AA^b$ are independently selected from the group consisting of alanine, β-alanine, γ-aminobutyric acid, arginine, asparagine, aspartic acid, γ-carboxyglutamic acid, citrulline, cysteine, glutamic acid, glutamine, glycine, histidine, isoleucine, leucine, lysine, methionine, norleucine, norvaline, ornithine, phenylalanine, proline, serine, threonine, tryptophan, tyrosine, and valine;

p is 1, 2, 3, or 4;

q is 1, 2, 3, 4, 5, 6, 7, 8, 9, or 10 (preferably 2, 3, or 4);

r is 1, 2, 3, 4, or 5;

s is 0 or 1; and (IIIa)

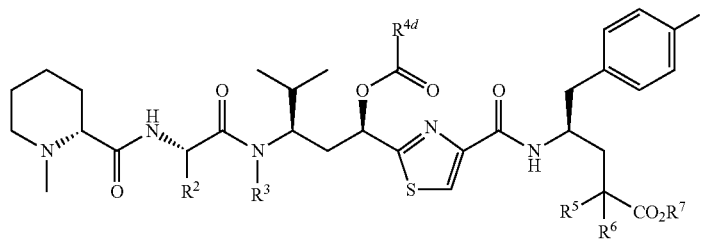
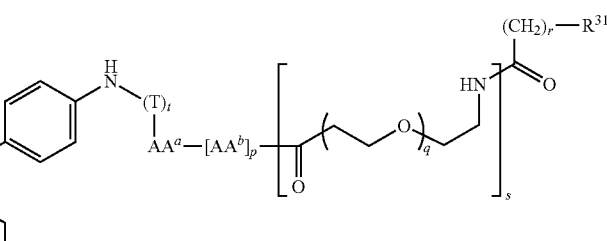

or a pharmaceutically acceptable salt thereof;
wherein
$R^2$ is Me, Et, $CH_2CH_2CH_3$, $CH(Me)_2$, $CH(Et)_2$, or

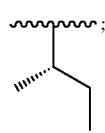

preferably $CH(Me)_2$, $CH(Et)_2$, or

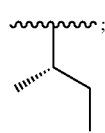

$R^3$ is H, $C_1$-$C_5$ alkyl, $C_1$-$C_5$ alkenyl, $C_1$-$C_5$ alkynyl, $CH_2OC(=O)C_1$-$C_5$ alkyl, $CH_2OC(=O)C_1$-$C_5$ alkenyl, or $CH_2OC(=O)C_1$-$C_5$ alkynyl (preferably $C_{1-5}$ alkyl);

$R^{31}$ is 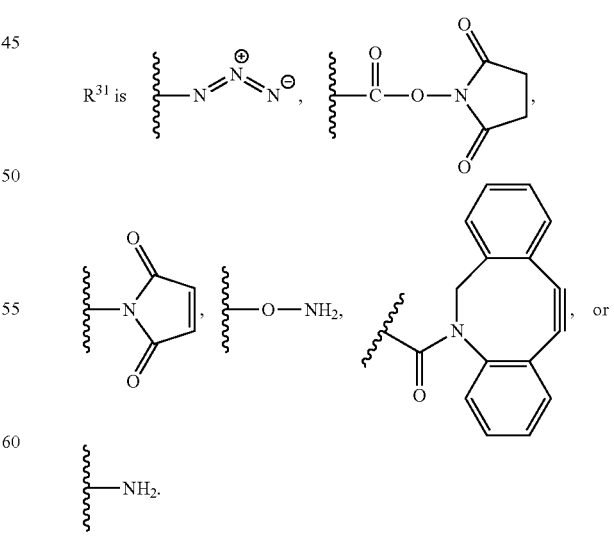

Another preferred tubulysin analog-linker compound has a structure represented by formula (IIIc):

(IIIc)

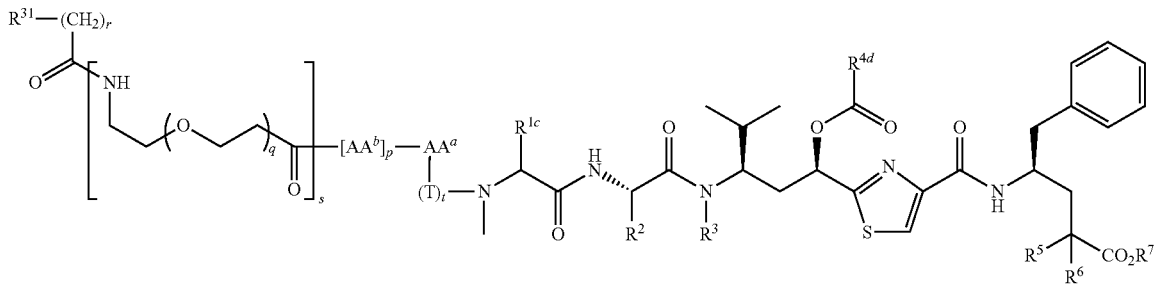

or a pharmaceutically acceptable salt thereof;
wherein
$R^{1c}$ is H, Me, or CH(Me)$_2$ (preferably CH(Me)$_2$);
$R^2$ is Me, Et, CH$_2$CH$_2$CH$_3$, CH(Me)$_2$, CH(Et)$_2$, or

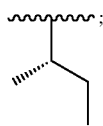;

preferably CH(Me)$_2$, CH(Et)$_2$, or

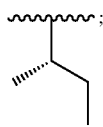;

$R^3$ is H, C$_1$-C$_5$ alkyl, C$_1$-C$_5$ alkenyl, C$_1$-C$_5$ alkynyl, CH$_2$OC(=O)C$_1$-C$_5$ alkyl, CH$_2$OC(=O)C$_1$-C$_5$ alkenyl, or CH$_2$OC(=O)C$_1$-C$_5$ alkynyl (preferably C$_{1-5}$ alkyl);
$R^{4d}$ is Me or NHMe;
$R^5$ and $R^6$ are each Me or combine with the carbon to which they are bonded to form a cyclopropyl ring (preferably both are Me);
$R^7$ is H, Me, or Et;
T is a self-immolating group;
t is 0 or 1;
AA$^a$ and each AA$^b$ are independently selected from the group consisting of alanine, β-alanine, γ-aminobutyric acid, arginine, asparagine, aspartic acid, γ-carboxyglutamic acid, citrulline, cysteine, glutamic acid, glutamine, glycine, histidine, isoleucine, leucine, lysine, methionine, norleucine, norvaline, ornithine, phenylalanine, proline, serine, threonine, tryptophan, tyrosine, and valine;
p is 1, 2, 3, or 4;
q is 1, 2, 3, 4, 5, 6, 7, 8, 9, or 10 (preferably 2, 3, or 4);
r is 1, 2, 3, 4, or 5;
s is 0 or 1; and $R^{31}$ is 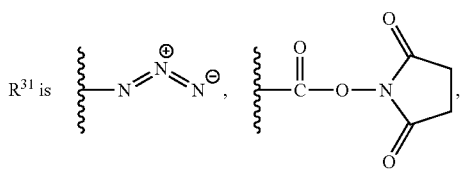

-continued

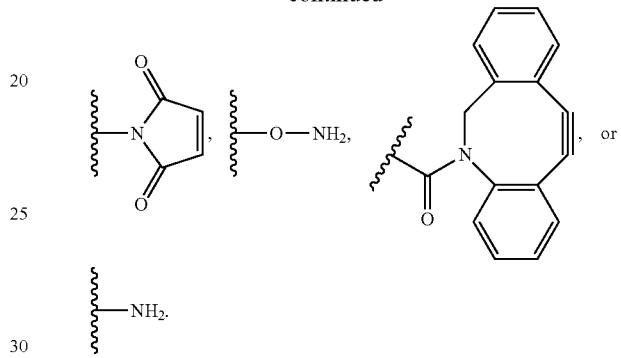

Thus, $R^{31}$ in formulae (IIIa) and (IIIc) is a reactive functional group capable of reacting with a complementary functional group on the antibody.

In formulae (IIIa) and (IIIc), -AA$^a$-[AA$^b$]$_p$- represents a polypeptide whose length is determined by the value of p (dipeptide if p is 1, tetrapeptide if p is 3, etc.). AA$^a$ is at the carboxy terminus of the polypeptide and its carboxyl group forms a peptide (amide) bond with an amine nitrogen of the tubulysin analog. Conversely, the last AA$^b$ is at the amino terminus of the polypeptide and its α-amino group forms a peptide bond with

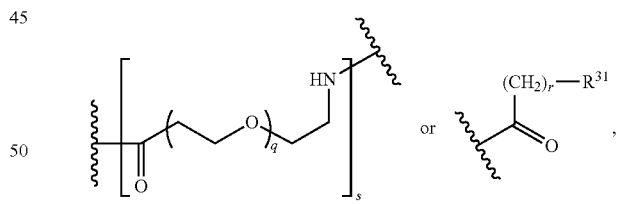

depending on whether s is 1 or 0, respectively.

In formulae (IIIa) and (IIIc), preferred polypeptides -AA$^a$-[AA$^b$]$_p$- are Val-Cit, Val-Lys, Lys-Val-Ala, Asp-Val-Ala, Val-Ala, Lys-Val-Cit, or Asp-Val-Cit, written in the conventional N-to-C direction, as in H$_2$N-Val-Cit-CO$_2$H). More preferably, the polypeptide is Val-Cit, Val-Lys, or Val-Ala.

As indicated by the subscript t equals 0 or 1, the self-immolating group is optionally present in compounds of formulae (IIIa) and (IIIc). When present, self-immolating group C preferably is a p-aminobenzyl oxycarbonyl (PABC) group, whose structure is shown below, with an asterisk (*) denoting the end of the PABC bonded to an amine nitrogen of the tubulysin analog.

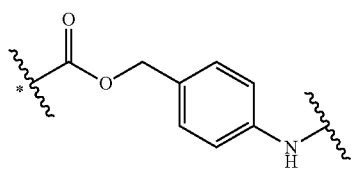
Examples of analog-linker compounds of this invention according to formula (IIIa), wherein $R^5$ and $R^6$ are both methyl include compounds (IIIa-1) through (IIIa-4):
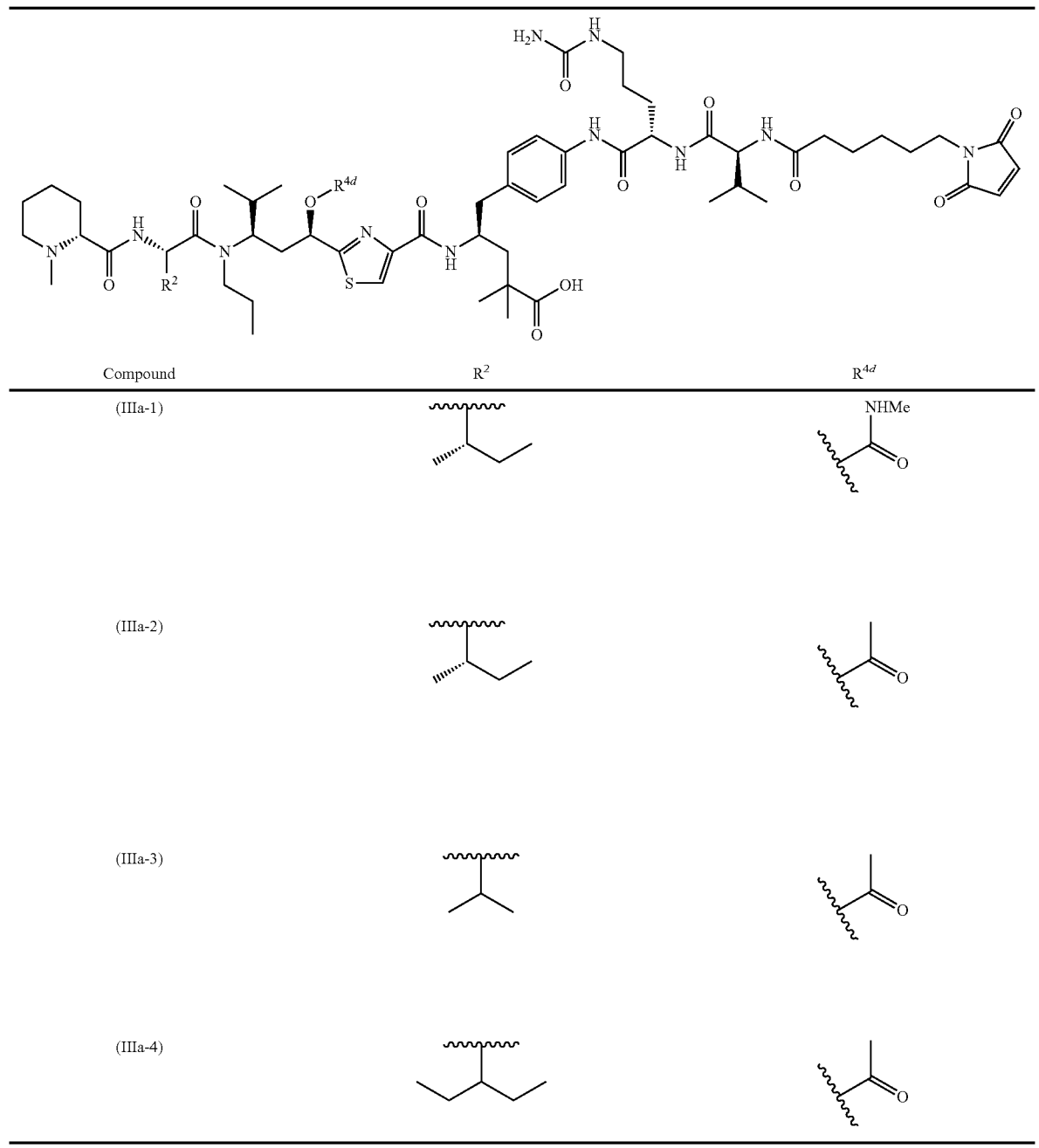
Specific tubulysin analog-linker compounds according to formula (IIIc) include those having structures represented by formulae (IIIc-1) through (IIIc-3):

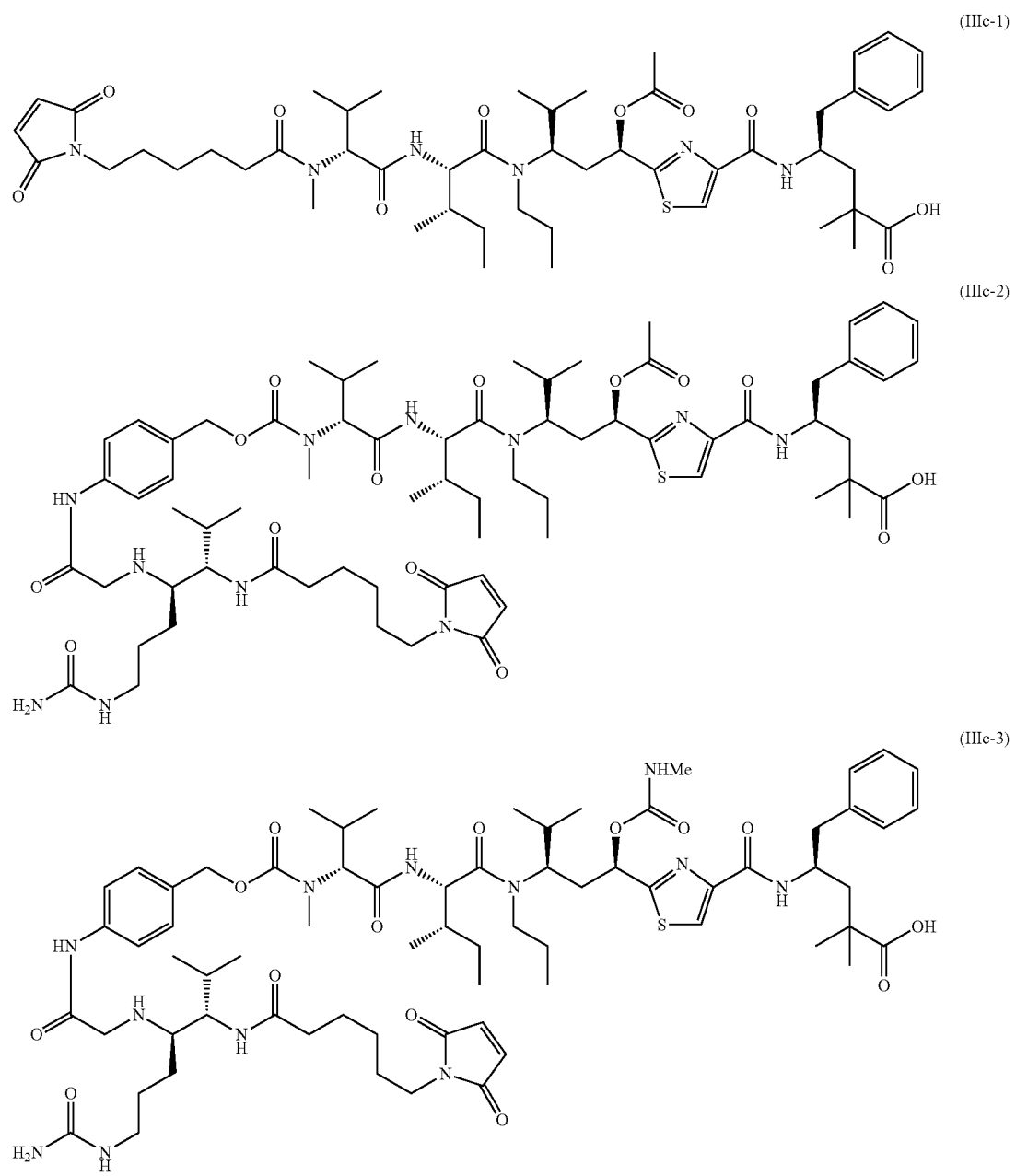

Preparation of Conjugates

This general procedure is based on introduction of free thiol groups into an antibody by reaction of lysine ε-amino groups with 2-iminothiolane, followed by reaction with a maleimide-containing drug-linker moiety, such as described above. Initially the antibody is buffer exchanged into 0.1 M phosphate buffer (pH 8.0) containing 50 mM NaCl and 2 mM diethylene triamine pentaacetic acid (DTPA) and concentrated to 5-10 mg/mL. Thiolation is achieved through addition of 2-iminothiolane to the antibody. The amount of 2-iminothiolane to be added can be determined by a preliminary experiment and varies from antibody to antibody. In the preliminary experiment, a titration of increasing amounts of 2-iminothiolane is added to the antibody, and following incubation with the antibody for 1 h at RT (room temperature, circa 25° C.), the antibody is desalted into 50 mM HEPES, 5 mM Glycine, 2 mM DTPA, pH 5.5 using a SEPHADEX™ G-25 column and the number of thiol groups introduced determined rapidly by reaction with dithiodipyridine (DTDP). Reaction of thiol groups with DTDP results in liberation of thiopyridine, which can be monitored spectroscopically at 324 nm. Samples at a protein concentration of 0.5-1.0 mg/mL are typically used. The absorbance at 280 nm can be used to accurately determine the concentration of protein in the samples, and then an aliquot of each sample (0.9 mL) is incubated with 0.1 mL DTDP (5 mM stock solution in ethanol) for 10 min at RT. Blank samples of buffer alone plus DTDP are also incubated alongside. After 10 min, absorbance at 324 nm is measured and the number of thiol groups is quantitated using an extinction coefficient for thiopyridine of 19,800 $M^{-1}$.

Typically a thiolation level of about two to three thiol groups per antibody is desirable. For example, with some antibodies this can be achieved by adding a 15-fold molar excess of 2-iminothiolane followed by incubation at RT for 1 h. The antibody is then incubated with 2-iminothiolane at the desired molar ratio and then desalted into conjugation buffer (50 mM HEPES, 5 mM glycine, 2 mM DTPA, pH 5.5)). The thiolated material is maintained on ice while the number of thiols introduced is quantitated as described above.

After verification of the number of thiols introduced, the drug (cytotoxin)-linker moiety is added at a 2.5-fold molar excess per thiol. The conjugation reaction is allowed to proceed in conjugation buffer containing a final concentration of 25% propylene glycol and 5% trehalose. Commonly, the drug-linker stock solution is dissolved in 100% DMSO. The stock solution is added directly to the thiolated antibody.

The conjugation reaction mixture is incubated at RT for 2 h with gentle stirring. A 10-fold molar excess of N-ethyl maleimide (100 mM Stock in DMSO) is then added to the conjugation mixture and stirred for an additional hour to block any unreacted thiols.

The sample is then filtered via a 0.2μ filter The material is buffer exchanged via TFF VivaFlow 50 Sartorius 30 MWCO PES membrane into 10 mg/mL glycine, 20 mg/mL sorbitol, 15% acetonitrile pH 5.0 (5×TFF buffer exchange volume), to remove any unreacted drug. The final formulation is carried out by TFF into 20 mg/mL sorbitol, 10 mg/mL glycine, pH 5.0.

Those skilled in the art will understand that the above-described conditions and methodology are exemplary and non-limiting and that other approaches for conjugation are known in the art and usable in the present invention.

A preferred antibody-drug conjugate of this invention is represented by formula (IIa):

wherein $R^2$ is Me, Et, $CH_2CH_2CH_3$, $CH(Me)_2$, $CH(Et)_2$, or

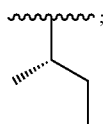

preferably $CH(Me)_2$, $CH(Et)_2$, or

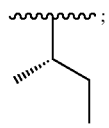

$R^3$ is H, $C_1$-$C_5$ alkyl, $C_1$-$C_5$ alkenyl, $C_1$-$C_5$ alkynyl, $CH_2OC(=O)C_1$-$C_5$ alkyl, $CH_2OC(=O)C_1$-$C_5$ alkenyl, or $CH_2OC(=O)C_1$-$C_5$ alkynyl (preferably $C_{1-5}$ alkyl);

$R^{4d}$ is Me or NHMe;

$R^5$ and $R^6$ are each Me or combine with the carbon to which they are bonded to form a cyclopropyl ring (preferably both are Me);

$R^7$ is H, Me, or Et;

T is a self-immolating group;

t is 0 or 1;

$AA^a$ and each $AA^b$ are independently selected from the group consisting of alanine, β-alanine, γ-aminobutyric acid, arginine, asparagine, aspartic acid, γ-carboxyglutamic acid, citrulline, cysteine, glutamic acid, glutamine, glycine, histidine, isoleucine, leucine, lysine, methionine, norleucine, norvaline, ornithine, phenylalanine, proline, serine, threonine, tryptophan, tyrosine, and valine;

p is 1, 2, 3, or 4;

q is 1, 2, 3, 4, 5, 6, 7, 8, 9, or 10 (preferably 2, 3, or 4);

r is 1, 2, 3, 4, or 5;

s is 0 or 1;

Ab is an antibody;

$R^{40}$ is

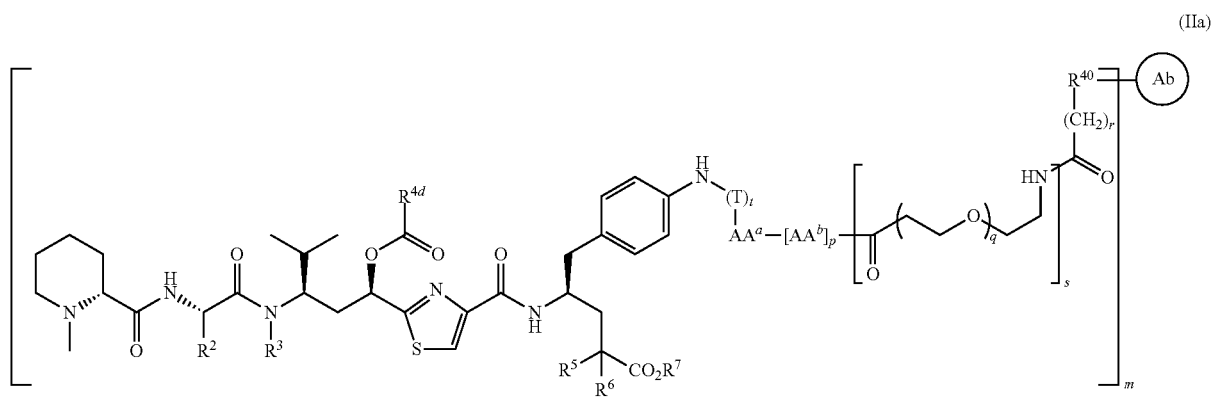

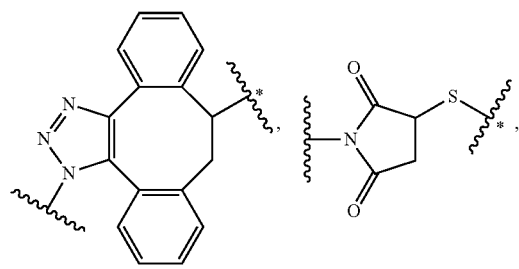

-continued

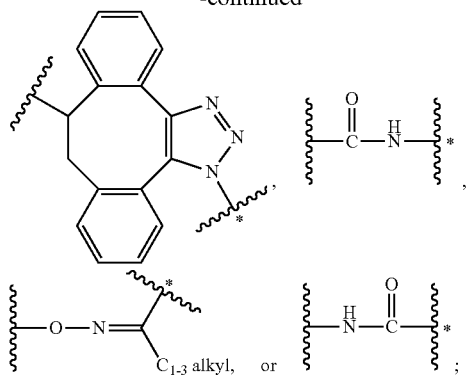

where the open valence of $R^{40}$ that is bonded to Ab is denoted by an asterisk (*); and m is 1, 2, 3, or 4.

Another preferred embodiment of an antibody-drug conjugate of this invention has a structure represented by formula (IIc):

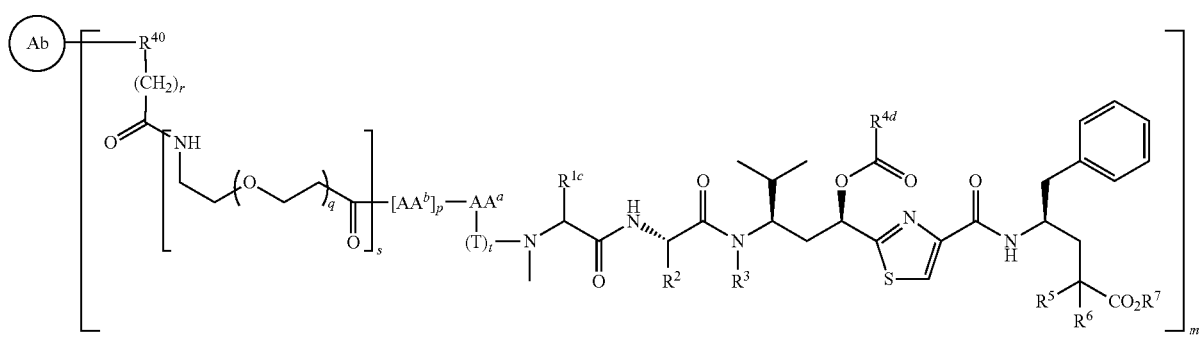

wherein
$R^2$ is Me, Et, $CH_2CH_2CH_3$, $CH(Me)_2$, $CH(Et)_2$, or

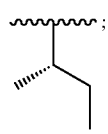

preferably $CH(Me)_2$, $CH(Et)_2$, or

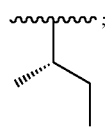

$R^3$ is H, $C_1$-$C_5$ alkyl, $C_1$-$C_5$ alkenyl, $C_1$-$C_5$ alkynyl, $CH_2OC(=O)C_1$-$C_5$ alkyl, $CH_2OC(=O)C_1$-$C_5$ alkenyl, or $CH_2OC(=O)C_1$-$C_5$ alkynyl (preferably $C_{1-5}$ alkyl);
$R^{4d}$ is Me or NHMe;
$R^5$ and $R^6$ are each Me or combine with the carbon to which they are bonded to form a cyclopropyl ring (preferably both are Me);
$R^7$ is H, Me, or Et;

T is a self-immolating group;

t is 0 or 1;

$AA^a$ and each $AA^b$ are independently selected from the group consisting of alanine, β-alanine, γ-aminobutyric acid, arginine, asparagine, aspartic acid, γ-carboxyglutamic acid, citrulline, cysteine, glutamic acid, glutamine, glycine, histidine, isoleucine, leucine, lysine, methionine, norleucine, norvaline, ornithine, phenylalanine, proline, serine, threonine, tryptophan, tyrosine, and valine;

p is 1, 2, 3, or 4;
q is 1, 2, 3, 4, 5, 6, 7, 8, 9, or 10 (preferably 2, 3, or 4);
r is 1, 2, 3, 4, or 5;
s is 0 or 1;
Ab is an antibody;

$R^{40}$ is

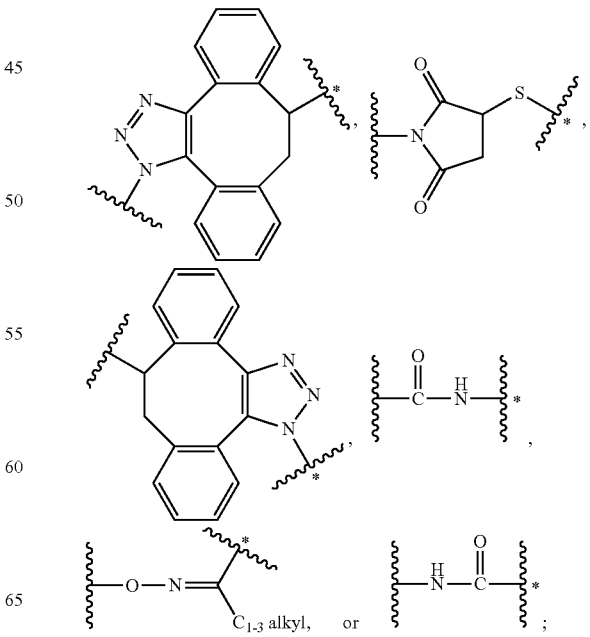

where the open valence of $R^{40}$ that is bonded to Ab is denoted by an asterisk (*); and m is 1, 2, 3, or 4.

Preferred polypeptides -$AA^a$-$[AA^b]_p$- in formula (IIa) and (IIc) are the same as in formulae (IIIa) and (IIIc).

Specific conjugates of tubulysin analogs of this invention include:

Pharmaceutical Compositions

In another aspect, the present disclosure provides a pharmaceutical composition comprising a compound of the present invention, or of a conjugate thereof, formulated together with a pharmaceutically acceptable carrier or excipient. It may optionally contain one or more additional pharmaceutically active ingredients, such as an antibody or another drug. The pharmaceutical compositions can be administered in a combination therapy with another therapeutic agent, especially another anti-cancer agent.

The pharmaceutical composition may comprise one or more excipients. Excipients that may be used include carriers, surface active agents, thickening or emulsifying agents, solid binders, dispersion or suspension aids, solubilizers, colorants, flavoring agents, coatings, disintegrating agents, lubricants, sweeteners, preservatives, isotonic agents, and combinations thereof. The selection and use of suitable excipients is taught in Gennaro, ed., *Remington: The Science and Practice of Pharmacy*, 20th Ed. (Lippincott Williams & Wilkins 2003), the disclosure of which is incorporated herein by reference.

Preferably, a pharmaceutical composition is suitable for intravenous, intramuscular, subcutaneous, parenteral, spinal or epidermal administration (e.g., by injection or infusion). Depending on the route of administration, the active compound may be coated in a material to protect it from the action of acids and other natural conditions that may inactivate it. The phrase "parenteral administration" means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion. Alternatively, the pharmaceutical composition can be administered via a non-parenteral route, such as a topical, epidermal or mucosal route of administration, for example, intranasally, orally, vaginally, rectally, sublingually or topically.

Pharmaceutical compositions can be in the form of sterile aqueous solutions or dispersions. They can also be formulated in a microemulsion, liposome, or other ordered structure suitable to achieve high drug concentration. The compositions can also be provided in the form of lyophilates, for reconstitution in water prior to administration.

The amount of active ingredient which can be combined with a carrier material to produce a single dosage form will vary depending upon the subject being treated and the particular mode of administration and will generally be that amount of the composition which produces a therapeutic effect. Generally, out of one hundred percent, this amount will range from about 0.01 percent to about ninety-nine percent of active ingredient, preferably from about 0.1 percent to about 70 percent, most preferably from about 1 percent to about 30 percent of active ingredient in combination with a pharmaceutically acceptable carrier.

Dosage regimens are adjusted to provide a therapeutic response. For example, a single bolus may be administered, several divided doses may be administered over time, or the dose may be proportionally reduced or increased as indicated by the exigencies of the situation. It is especially advantageous to formulate parenteral compositions in dosage unit form for ease of administration and uniformity of dosage. "Dosage unit form" refers to physically discrete units suited as unitary dosages for the subjects to be treated; each unit containing a predetermined quantity of active compound calculated to produce the desired therapeutic response, in association with the required pharmaceutical carrier.

The dosage ranges from about 0.0001 to 100 mg/kg, and more usually 0.01 to 5 mg/kg, of the host body weight. For example dosages can be 0.3 mg/kg body weight, 1 mg/kg body weight, 3 mg/kg body weight, 5 mg/kg body weight or 10 mg/kg body weight or within the range of 1-10 mg/kg. Exemplary treatment regimens are administration once per week, once every two weeks, once every three weeks, once every four weeks, once a month, once every 3 months, or once every three to 6 months. Preferred dosage regimens include 1 mg/kg body weight or 3 mg/kg body weight via intravenous administration, using one of the following dosing schedules: (i) every four weeks for six dosages, then every three months; (ii) every three weeks; (iii) 3 mg/kg body weight once followed by 1 mg/kg body weight every three weeks. In some methods, dosage is adjusted to achieve a plasma antibody concentration of about 1-1000 µg/mL and in some methods about 25-300 µg/mL.

A "therapeutically effective amount" of a compound of the invention preferably results in a decrease in severity of disease symptoms, an increase in frequency and duration of disease symptom-free periods, or a prevention of impairment or disability due to the disease affliction. For example, for the treatment of tumor-bearing subjects, a "therapeutically effective amount" preferably inhibits tumor growth by at least about 20%, more preferably by at least about 40%, even more preferably by at least about 60%, and still more preferably by at least about 80% relative to untreated subjects. A therapeutically effective amount of a therapeutic compound can decrease tumor size, or otherwise ameliorate symptoms in a subject, which is typically a human but can be another mammal.

The pharmaceutical composition can be a controlled or sustained release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. See, e.g., *Sustained and Controlled Release Drug Delivery Systems*, J. R. Robinson, ed., Marcel Dekker, Inc., New York, 1978.

Therapeutic compositions can be administered via medical devices such as (1) needleless hypodermic injection devices (e.g., U.S. Pat. Nos. 5,399,163; 5,383,851; 5,312,335; 5,064,413; 4,941,880; 4,790,824; and 4,596,556); (2) micro-infusion pumps (U.S. Pat. No. 4,487,603); (3) transdermal devices (U.S. Pat. No. 4,486,194); (4) infusion apparati (U.S. Pat. Nos. 4,447,233 and 4,447,224); and (5) osmotic devices (U.S. Pat. Nos. 4,439,196 and 4,475,196); the disclosures of which are incorporated herein by reference.

In certain embodiments, the pharmaceutical composition can be formulated to ensure proper distribution in vivo. For example, to ensure that the therapeutic compounds of the invention cross the blood-brain barrier, they can be formulated in liposomes, which may additionally comprise targeting moieties to enhance selective transport to specific cells or organs. See, e.g. U.S. Pat. Nos. 4,522,811; 5,374,548; 5,416,016; and 5,399,331; V. V. Ranade (1989) *J. Clin. Pharmacol.* 29:685; Umezawa et al., (1988) *Biochem. Biophys. Res. Commun.* 153:1038; Bloeman et al. (1995) *FEBS*

Lett. 357:140; M. Owais et al. (1995) *Antimicrob. Agents Chemother.* 39:180; Briscoe et al. (1995) *Am. J. Physiol.* 1233:134; Schreier et al. (1994) *J. Biol. Chem.* 269:9090; Keinanen and Laukkanen (1994) *FEBS Lett.* 346:123; and Killion and Fidler (1994) *Immunomethods* 4:273.

Uses

Compounds of this invention or their conjugates can be used for treating diseases such as, but not limited to, hyperproliferative diseases, including: cancers of the head and neck which include tumors of the head, neck, nasal cavity, paranasal sinuses, nasopharynx, oral cavity, oropharynx, larynx, hypopharynx, salivary glands, and paragangliomas; cancers of the liver and biliary tree, particularly hepatocellular carcinoma; intestinal cancers, particularly colorectal cancer; ovarian cancer; small cell and non-small cell lung cancer (SCLC and NSCLC); breast cancer sarcomas, such as fibrosarcoma, malignant fibrous histiocytoma, embryonal rhabdomyosarcoma, leiomysosarcoma, neurofibrosarcoma, osteosarcoma, synovial sarcoma, liposarcoma, and alveolar soft part sarcoma; leukemias such as acute promyelocytic leukemia (APL), acute myelogenous leukemia (AML), acute lymphoblastic leukemia (ALL), and chronic myelogenous leukemia (CML); neoplasms of the central nervous systems, particularly brain cancer; multiple myeloma (MM), lymphomas such as Hodgkin's lymphoma, lymphoplasmacytoid lymphoma, follicular lymphoma, mucosa-associated lymphoid tissue lymphoma, mantle cell lymphoma, B-lineage large cell lymphoma, Burkitt's lymphoma, and T-cell anaplastic large cell lymphoma. Clinically, practice of the methods and use of compositions described herein will result in a reduction in the size or number of the cancerous growth and/or a reduction in associated symptoms (where applicable). Pathologically, practice of the method and use of compositions described herein will produce a pathologically relevant response, such as inhibition of cancer cell proliferation, reduction in the size of the cancer or tumor, prevention of further metastasis, and inhibition of tumor angiogenesis. The method of treating such diseases comprises administering a therapeutically effective amount of an inventive combination to a subject. The method may be repeated as necessary. Especially, the cancer can be renal, lung, gastric, or ovarian cancer.

Compounds of this invention or their conjugates can be administered in combination with other therapeutic agents, including antibodies, alkylating agents, angiogenesis inhibitors, antimetabolites, DNA cleavers, DNA crosslinkers, DNA intercalators, DNA minor groove binders, enediynes, heat shock protein 90 inhibitors, histone deacetylase inhibitors, immunomodulators, microtubule stabilizers, nucleoside (purine or pyrimidine) analogs, nuclear export inhibitors, proteasome inhibitors, topoisomerase (I or II) inhibitors, tyrosine kinase inhibitors, and serine/threonine kinase inhibitors. Specific therapeutic agents include adalimumab, ansamitocin P3, auristatin, bendamustine, bevacizumab, bicalutamide, bleomycin, bortezomib, busulfan, callistatin A, camptothecin, capecitabine, carboplatin, carmustine, cetuximab, cisplatin, cladribin, cytarabin, cryptophycins, dacarbazine, dasatinib, daunorubicin, docetaxel, doxorubicin, duocarmycin, dynemycin A, epothilones, etoposide, floxuridine, fludarabine, 5-fluorouracil, gefitinib, gemcitabine, ipilimumab, hydroxyurea, imatinib, infliximab, interferons, interleukins, β-lapachone, lenalidomide, irinotecan, maytansine, mechlorethamine, melphalan, 6-mercaptopurine, methotrexate, mitomycin C, nilotinib, oxaliplatin, paclitaxel, procarbazine, suberoylanilide hydroxamic acid (SAHA), 6-thioguanidine, thiotepa, teniposide, topotecan, trastuzumab, trichostatin A, vinblastine, vincristine, and vindesine.

EXAMPLES

The practice of this invention can be further understood by reference to the following examples, which are provided by way of illustration and not of limitation.

Example 1—Compounds (Ia-2) and (Ia-6)

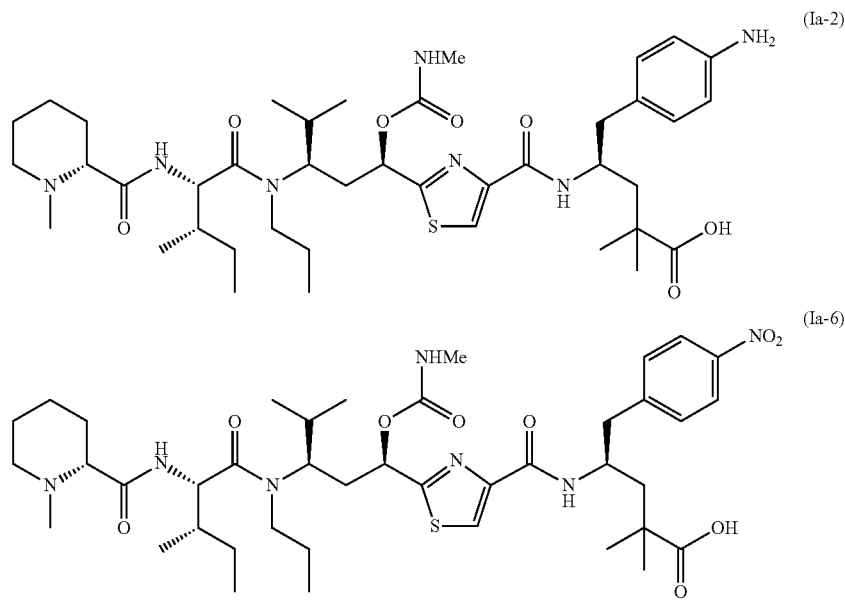

The synthesis of compounds (Ia-2) and (Ia-6) is shown in the scheme of FIG. 1.

To a solution of (S)-2-((tert-butoxycarbonyl)amino)-3-(4-nitrophenyl)propanoic acid 1 (2.0 g, 6.45 mmol; Cong et al. 2014) in dichloromethane (DCM) (20 mL) at 0° C. was added 4-(dimethylamino)pyridine (DMAP, 1.18 g, 9.67 mmol) and then 2,2-dimethyl-1,3-dioxane-4,6-dione 2 (Meldrum's acid, 1.02 g, 7.09 mmol). Solid N-(3-dimethylaminopropyl)-N'-ethylcarbodiimide hydrochloride (EDC, 1.36 g, 7.09 mmol) was added. The reaction was stirred at 0° C. for 8 h. The brown reaction mixture was washed with 5% aqueous KHSO$_4$ solution (4×) and brine. The organic layer was dried over anhydrous MgSO$_4$ and filtered to give crude (S)-tert-butyl(1-(2,2-dimethyl-4,6-dioxo-1,3-dioxan-5-ylidene)-1-hydroxy-3-(4-nitrophenyl)propan-2-yl)carbamate 3 as a yellow DCM solution which was used directly in the next step. MS (ESI$^+$) m/z 437.4 (M+H)$^+$.

To a solution of the above compound 3 in DCM (50 mL) at 0° C. was added acetic acid (4.06 mL, 71.0 mmol) followed by NaBH$_4$ (0.610 g, 16.1 mmol) in 0.2 gram portions over 15 min. After stirring at 0° C. for 2 h, additional NaBH$_4$ (0.2 g) was added. After stirring at 0° C. for an additional 30 min, the reaction was complete. The reaction was quenched with brine and extracted with DCM (3×). The pooled organic extracts were dried over anhydrous MgSO$_4$, filtered, and concentrated in vacuo. The residue was purified by silica gel flash chromatography (gradient from 0% to 40% EtOAc/DCM) to afford (R)-tert-butyl(1-(2,2-dimethyl-4,6-dioxo-1,3-dioxan-5-yl)-3-(4-nitrophenyl)propan-2-yl)carbamate 4 (2.54 g, 93%) as a clear tan oil. $^1$H NMR (CDCl$_3$) δ 8.20 (d, J=8.8 Hz, 2H), 7.42 (d, J=8.8 Hz, 2H), 4.31 (m, 1H), 3.86 (br s, 1H), 3.64 (s, 1H), 2.93-3.03 (m, 2H), 2.16-2.38 (m, 2H), 1.80 (s, 3H), 1.78 (s, 3H), 1.37 (s, 9H). MS (ESI$^+$) m/z 423.4 (M+H)$^+$.

A solution of compound 4 (2.54 g, 6.01 mmol) in toluene (50 mL) was stirred at 90° C. for 6 h. After cooling to room temperature (RT), the reaction mixture was concentrated in vacuo. The residue was purified by silica gel flash chromatography (gradient from 0% to 60% EtOAc/DCM) to afford (R)-tert-butyl 2-(4-nitrobenzyl)-5-oxopyrrolidine-1-carboxylate 5 (0.80 g, 42%) as a tan solid. $^1$H NMR (CDCl$_3$) δ ppm 8.22 (d, J=8.6 Hz, 2H), 7.41 (d, J=8.6 Hz, 2H), 4.39-4.48 (m, 1H), 3.31 (dd, J=13.2, 3.6 Hz, 1H), 2.87 (dd, J=13.2, 9.2 Hz, 1H), 2.39-2.48 (m, 1H), 1.98-2.12 (m, 1H), 1.73-1.84 (m, 2H), 1.60 (s, 9H). MS (ESI$^+$) m/z 343.2 (M+Na)$^+$.

To a solution of compound 5 (150 mg, 0.468 mmol) in tetrahydrofuran (THF, 3 mL) at −78° C. was added LiHMDS (1.17 mL, 1.17 mmol, 1M in toluene). The reaction mixture was stirred at −78° C. for 30 min. Iodomethane (266 mg, 1.87 mmol) in 1 mL of THF was added dropwise. The reaction mixture was stirred at −78° C. for 2 h, gradually warmed up to 0° C., and then stirred at 0° C. for 1 h. The reaction was quenched by adding saturated aqueous NH$_4$Cl solution and extracted with DCM (3×). The combined organic extracts were dried over anhydrous MgSO$_4$, filtered, and concentrated in vacuo. The residue was purified on a C18 Phenomenex Luna S5 ODS 30×100 mm reverse phase preparative HPLC column eluting with 10-90% aq. CH$_3$CN containing 0.05% trifluoroacetic acid (TFA) over a 12 minute gradient to afford (S)-tert-butyl 3,3-dimethyl-5-(4-nitrobenzyl)-2-oxopyrrolidine-1-carboxylate 6 (61 mg, 37%) as a white solid. $^1$H NMR (CDCl$_3$) δ 8.18 (d, J=8.6 Hz, 2H), 7.38 (d, J=8.6 Hz, 2H), 4.19-4.28 (m, 1H), 3.59 (dd, J=13.0, 3.5 Hz, 1H), 2.75 (dd, J=13.0, 9.9 Hz, 1H), 1.83 (dd, J=13.0, 8.3 Hz, 1H), 1.61 (m, 1H), 1.59 (s, 9H), 1.23 (s, 3H), 1.15 (s, 3H). MS (ESI$^+$) m/z 719.1 (2M+Na)$^+$.

To a solution of compound 6 (110 mg, 0.316 mmol) in THF (1.0 mL) and MeOH (1.0 mL) at RT was added 3N aqueous NaOH solution (0.21 mL, 0.63 mmol) dropwise. The reaction mixture was stirred at RT for 4 h. After cooling to 0° C., the pH of the reaction mixture was adjusted to pH 3 with 1N aqueous HCl solution and extracted with DCM (3×). The combined organic extracts were dried over anhydrous MgSO$_4$, filtered, and concentrated in vacuo to give crude (S)-4-((tert-butoxycarbonyl)amino)-2,2-dimethyl-5-(4-nitrophenyl)pentanoic acid 7. MS (ESI$^+$) m/z 755.0 (2M+Na)$^+$.

The above crude product was dissolved in 1.5 mL of DCM. TFA (0.5 mL) was added. The reaction mixture was stirred at RT for 1 h and then concentrated in vacuo. The residue was purified on a C18 Phenomenex Luna S5 ODS 30×100 mm reverse phase preparative HPLC column eluting with 10-90% aq CH$_3$CN containing 0.05% TFA over a 12 minute gradient to give (S)-4-amino-2,2-dimethyl-5-(4-nitrophenyl)pentanoic acid 8 (48 mg, 40%) as a white solid. $^1$H NMR (CD$_3$OD) δ 8.25 (d, J=8.8 Hz, 2H), 7.55 (d, J=8.8 Hz, 2H), 3.58-3.66 (m, 1H), 3.03-3.11 (m, 2H), 1.97 (dd, J=15.4, 6.6 Hz, 1H), 1.75 (dd, J=15.4, 3.7 Hz, 1H), 1.23 (s, 3H), 1.10 (s, 3H). MS (ESI$^+$) m/z 296.3 (M+Na)$^+$.

To a solution of 2-((5R,7R,10S)-10-((S)-sec-butyl)-7-isopropyl-12-((R)-1-methylpiperidin-2-yl)-3,9,12-trioxo-8-propyl-4-oxa-2,8,11-triazadodecan-5-yl)thiazole-4-carboxylic acid 9 (Cong et al. 2014, 20 mg, 0.034 mmol) in DMF (0.5 mL) was added N,N,N',N'-tetramethyl-O-(7-azabenzotriazol-1-yl)uronium hexafluorophosphate (HATU, 15.7 mg, 0.041 mmol) and N,N-diisopropylethylamine (DIEA, 0.018 mL, 0.103 mmol). The reaction mixture was stirred at RT for 30 min. A solution of pentanoic acid 8 (9.15 mg, 0.034 mmol) and 1 eq. of DIEA (4.4 mg, 0.034 mmol) in DMF (0.5 mL) were added and the reaction mixture was stirred at RT overnight. The reaction mixture was purified on a C18 Phenomenex Luna S5 ODS 30×100 mm reverse phase HPLC column eluting with 10-90% aq CH$_3$CN containing 0.05% TFA over a 12 minute gradient to give (S)-5-(4-nitrophenyl)-4-(2-((5R,7R,10S)-10-((S)-sec-butyl)-7-isopropyl-12-((R)-1-methylpiperidin-2-yl)-3,9,12-trioxo-8-propyl-4-oxa-2,8,11-triazadodecan-5-yl)thiazole-4-carboxamido)-2,2-dimethylpentanoic acid (Ia-6) (16 mg, 56%) as a white solid. MS (ESI$^+$) m/z 830.2 (M+H)$^+$.

To a solution of the compound (Ia-6) (15 mg, 0.018 mmol) in MeOH (4 mL) was added palladium on carbon, 50% wet (7.69 mg, 3.61 μmol). The resulting suspension was stirred under a hydrogen balloon at RT for 4 h. The reaction mixture was filtered through a pipette containing a cotton plug and CELITE™ and the filtrate was concentrated in vacuo. The residue was purified on a C18 Phenomenex Luna S5 ODS 21×100 mm reverse phase preparative HPLC column eluting with 10-90% aq CH$_3$CN containing 0.05% TFA over a 12 minute gradient to give (S)-5-(4-aminophenyl)-4-(2-((5R,7R,10S)-10-((S)-sec-butyl)-7-isopropyl-12-((R)-1-methylpiperidin-2-yl)-3,9,12-trioxo-8-propyl-4-oxa-2,8,11-triazadodecan-5-yl)thiazole-4-carboxamido)-2,2-dimethylpentanoic acid (Ia-2) (6 mg, 37%) as a white solid. $^1$H NMR (CD$_3$OD) δ 8.03 (s, 1H), 7.35 (d, J=8.1 Hz, 2H), 7.16 (d, J=8.1 Hz, 2H), 5.62 (d, J=10.8 Hz, 1H), 4.64-4.74 (m, 1H), 4.44 (br s, 1H), 3.78 (m, 1H), 3.41-3.53 (m, 2H), 3.01-3.12 (m, 2H), 2.83-2.96 (m, 1H), 2.75 (s, 3H), 2.72 (s, 3H), 2.22 (m, 5H), 1.95 (m, 3H), 1.68-1.85 (m, 3H), 1.23 (s, 3H), 1.20 (d, J=7.04 Hz, 6H), 1.16 (s, 3H), 0.98-1.08 (m, 16H). MS (ESI$^+$) m/z 800.1 (M+H)$^+$.

Example 2—Compounds (Ia-1) and (Ia-5)

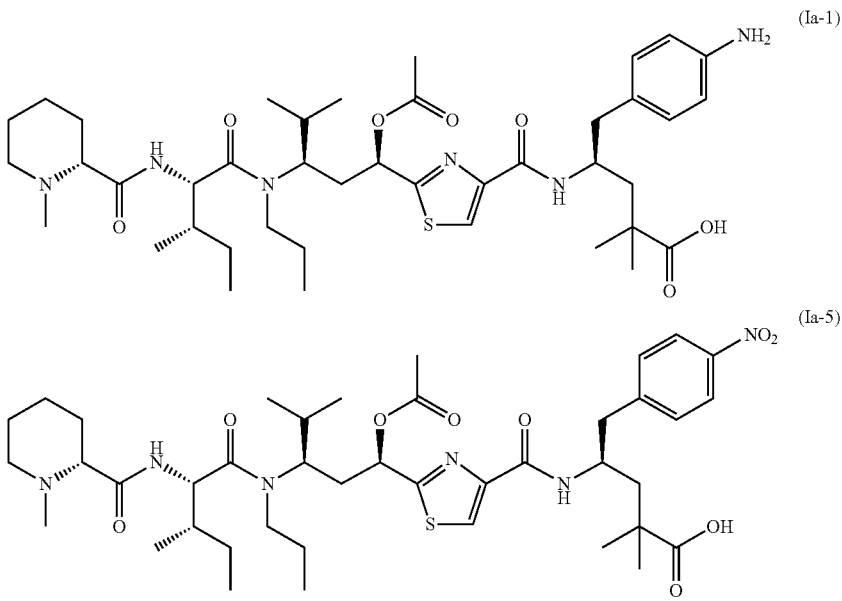

Generally following the procedure of FIG. 1 and Example 1, acid 10 (Cheng et al. 2013) was used to prepare compound (Ia-5), which was then converted to compound (Ia-1) (10 mg, 44% over two steps).

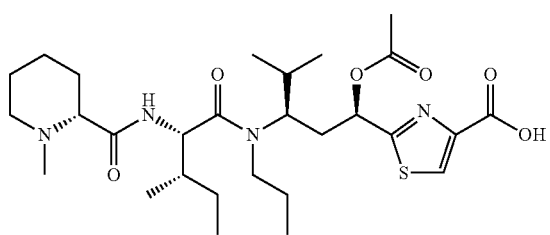

The analytical properties of compound (Ia-1) were: $^1$H NMR (400 MHz, CD$_3$OD) δ 8.04 (s, 1H), 7.38 (d, J=8.4 Hz, 2H), 7.18 (d, J=8.4 Hz, 2H), 5.70 (d, J=10.6 Hz, 1H), 4.55 (d, J=8.2 Hz, 1H), 4.45-4.43 (m, 1H), 3.79 (d, J=9.5 Hz, 1H), 3.57-3.53 (m, 1H), 3.47-3.45 (m, 1H), 3.26-3.14 (m, 1H), 3.06 (m, 1H), 2.93-2.81 (m, 3H), 2.74 (s, 3H), 2.39-2.33 (m, 1H), 2.22-2.25 (m, 4H), 2.18 (s, 3H), 1.93-1.91 (m, 3H), 1.82-1.69 (m, 4H), 1.67-1.58 (m, 3H), 1.19 (s, 3H), 1.14 (s, 3H), 1.05-0.86 (m, 17H); MS (ESI$^+$) m/z 785.5 (M+H)$^+$.

The analytical properties of compound (Ia-5) were: $^1$H NMR (400 MHz, CD$_3$OD) δ 8.17 (d, J=8.4 Hz, 2H), 8.04 (s, 1H), 7.48 (d, J=8.4 Hz, 2H), 5.75 (d, J=12.1 Hz, 1H), 4.64 (t, J=8.9 Hz, 1H), 4.58-4.47 (m, 1H), 3.75 (dd, J=12.2, 2.8 Hz, 1H), 3.59 (m, 1H), 3.44 (d, J=12.2 Hz, 1H), 3.20-3.09 (m, 1H), 3.07-2.96 (m, 3H), 2.74 (s, 3H), 2.41-2.31 (m, 1H), 2.22-2.24 (m, 3H), 2.19 (s, 3H), 1.93 (m, 4H), 1.79 (m, 3H), 1.66-1.50 (m, 2H), 1.21 (s, 3H), 1.15 (s, 3H), 1.05 (d, J=6.6 Hz, 3H), 1.00-0.86 (m, 17H); MS (ESI$^+$) m/z 815.4 (M+H)$^+$.

Example 3—Compounds (Ia-3) and (Ia-7)

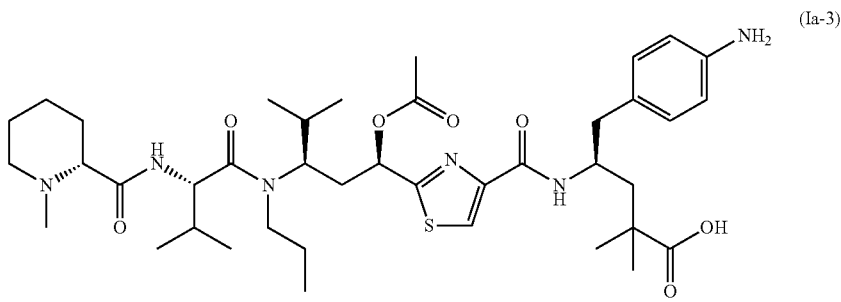

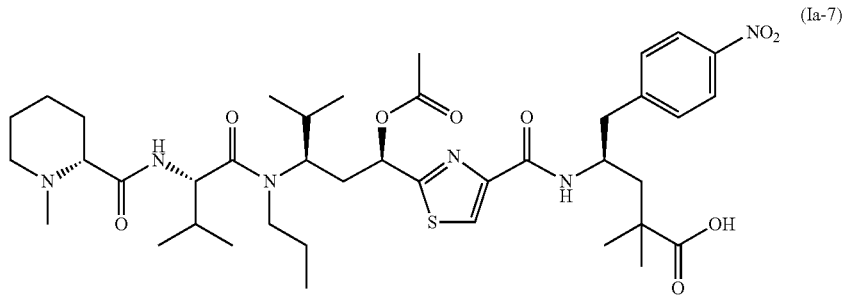
(Ia-7)

Figure 2:
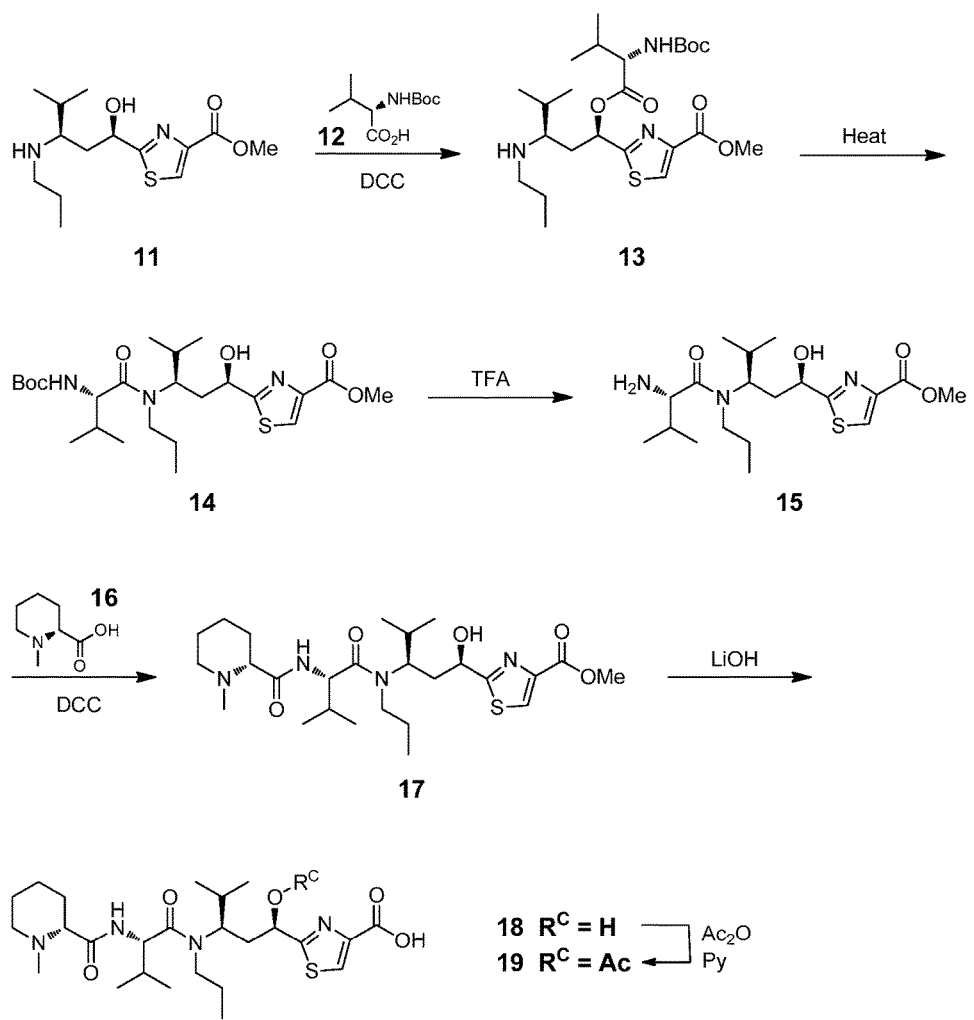
FIG. 2 shows a scheme for the synthesis of intermediate acid 19, which is used for the synthesis of compounds (Ia-3) and (Ia-7).

FIG. 2 shows a scheme for the synthesis of acid 19, which is a precursor for the synthesis of compounds (Ia-7) and (Ia-3).

Dicyclohexylcarbodiimide (DCC, 0.824 g, 3.99 mmol) was added to a mixture of methyl 2-((1R,3R)-1-hydroxy-4-methyl-3-(propylamino)pentyl)thiazole-4-carboxylate 11 (Cheng et al. 2013, 1 g, 3.33 mmol), Boc-protected valine 12 (0.796 g, 3.66 mmol) and t-butanol hydrate (0.612 g, 3.99 mmol) in DCM (15 mL) at 0° C. The reaction mixture was allowed to warm up to RT and stirred at RT overnight. The solid was filtered off, and the filtrate was concentrated. The crude product was purified by flash chromatography eluting from silica gel with a gradient of 0-8% MeOH in DCM containing 1% $NH_4OH$ to afford 1.3 g of methyl 2-((6S,9R,11R)-6,11-diisopropyl-2,2-dimethyl-4,7-dioxo-3,8-dioxa-5,12-diazapentadecan-9-yl)thiazole-4-carboxylate 13 as a colorless oil. MS: (+) m/z 500.3 (M+1).

A solution of compound 13 (0.5 g, 1.001 mmol) in o-xylene (3 mL) was heated at 120° C. overnight. The solvent was evaporated off. The crude product was purified by flash chromatography eluting from silica gel with a gradient of 0-100% EtOAc in hexanes to afford 0.29 g of methyl 2-((1R,3R)-3-((S)-2-((tert-butoxycarbonyl)amino)-3-methyl-N-propylbutanamido)-1-hydroxy-4-methylpentyl)thiazole-4-carboxylate 14 as a light-yellow solid. MS: (+) m/z 500.3 (M+1).

TFA (7.7 mL, 1.571 mmol) was added to a mixture of compound 14 (0.785 g, 1.571 mmol) in DCM (15 mL). After the reaction mixture was stirred at RT for 30 min, it was concentrated by evaporation of solvent, diluted with EtOAc, and washed once with saturated aqueous $NaHCO_3$. The aqueous solution was back-extracted twice with EtOAc. The combined organic layers were dried, filtered, and concentrated to afford 0.63 g of methyl 2-((1R,3R)-3-((S)-2-amino-3-methyl-N-propylbutanamido)-1-hydroxy-4-methylpentyl)-thiazole-4-carboxylate 15 as a light-yellow solid. MS: (+) m/z 400.3 (M+1).

DCC (0.258 g, 1.251 mmol) was added to a mixture of compound 15 (0.25 g, 0.626 mmol), (R)-1-methylpiperidine-2-carboxylic acid 16 (0.11 g, 0.751 mmol, Oakwood Products), and t-butanol hydrate (0.192 g, 1.251 mmol) in DCM (10 mL) at 0° C. The reaction mixture was allowed to warm to RT and stirred at RT overnight. The solid was filtered off, and the filtrate was concentrated. The residue was dissolved in EtOAc, and washed once with saturated aqueous $NaHCO_3$. The aqueous solution was back-extracted twice with EtOAc. The combined organic layers were dried, filtered, and concentrated. The crude product was purified by flash chromatography eluting from silica gel with a gradient of 0-20% MeOH in DCM to afford 0.12 g of methyl 2-((1R,3R)-1-hydroxy-4-methyl-3-((S)-3-methyl-2-((R)-1-methylpiperidine-2-carboxamido)-N-propylbutanamido)pentyl)thiazole-4-carboxylate 17 as a light yellow solid. MS: (+) m/z 525.3 (M+1).

LiOH (10.95 mg, 0.457 mmol) in water (0.5 mL) was added to a solution of compound 17 (0.12 g, 0.229 mmol) in THF (1 mL) at RT. After the reaction mixture was stirred at RT for 2 h. The solvent was removed by evaporation. The crude product was purified by flash chromatography, eluting from silica gel with a gradient of 0-30% MeOH in DCM to afford 95 mg of 2-((1R,3R)-1-hydroxy-4-methyl-3-((S)-3-methyl-2-((R)-1-methylpiperidine-2-carboxamido)-N-propylbutanamido)pentyl)thiazole-4-carboxylic acid 18 as a white solid. MS: (+) m/z 511.3 (M+1).

A solution of compound 18 (95 mg, 0.186 mmol) in pyridine (1.8 mL) was cooled in an ice-water bath and acetic anhydride (0.088 mL, 0.930 mmol) was added. The reaction mixture was allowed to warm up to RT, and stirred at RT overnight. A 1:1 (v/v) solution of degassed water and THF (8 mL) was added after the reaction mixture was cooled in an ice-water bath. The reaction mixture was then stirred at RT for 8 h. The solvent was evaporated off. The crude product was purified by flash chromatography eluting from silica gel with a gradient of 0-30% MeOH in DCM to afford 90 mg of 2-((1R,3R)-1-acetoxy-4-methyl-3-((S)-3-methyl-2-((R)-1-methylpiperidine-2-carboxamido)-N-propylbutanamido)pentyl)thiazole-4-carboxylic acid 19 as a white solid. MS: (+) m/z 553.3 (M+1).

Generally following the procedure of FIG. 1 and Example 1, acid 19 was used to prepare compound (Ia-7), which was then converted to compound (Ia-3) (11 mg, 48% over two steps). The analytical properties of compound (Ia-3) were: $^1$H NMR (400 MHz, $CD_3OD$) δ 8.03 (s, 1H), 7.92 (d, J=9.5 Hz, 1H), 7.31 (d, J=8.4 Hz, 2H), 7.11 (d, J=8.4 Hz, 2H), 5.75 (d, J=10.8 Hz, 1H), 4.59 (d, J=7.9 Hz, 1H), 4.45-4.43 (m, 1H), 3.79 (d, J=9.5 Hz, 1H), 3.57-3.53 (m, 1H), 3.47-3.45 (m, 1H), 3.26-3.14 (m, 1H), 3.06 (m, 1H), 2.93-2.81 (m, 3H), 2.74 (s, 3H), 2.39-2.33 (m, 1H), 2.22-2.25 (m, 4H), 2.18 (s, 3H), 1.93-1.91 (m, 3H), 1.82-1.69 (m, 4H), 1.67-1.58 (m, 1H), 1.20 (s, 3H), 1.16 (s, 3H), 1.08-0.96 (m, 14H), 0.91 (d, J=6.6 Hz, 3H); MS (ESI$^+$) m/z 771.3 (M+H)$^+$.

The analytical properties of compound (Ia-7) were: $^1$H NMR (400 MHz, $CD_3OD$) δ 8.13 (d, J=8.6 Hz, 2H), 8.04 (s, 1H), 7.48 (d, J=8.6 Hz, 2H), 5.75 (d, J=11.8 Hz, 1H), 4.64-4.7 (m, 2H), 3.77 (d, J=9.7 Hz, 1H), 3.60-3.39 (m, 2H), 3.23-3.12 (m, 2H), 3.07-2.96 (m, 3H), 2.74 (s, 3H), 2.36 (t, J=11.8 Hz, 1H), 2.22-2.24 (m, 3H), 2.18 (s, 3H), 1.93 (m, 3H), 1.79 (m, 3H), 1.83-1.74 (m, 2H), 1.23 (s, 3H), 1.19 (s, 3H), 1.11-0.87 (m, 17H); MS (ESI$^+$) m/z 801.4 (M+H)$^+$.

Example 4—Compounds (Ib-1) to (Ib-4)

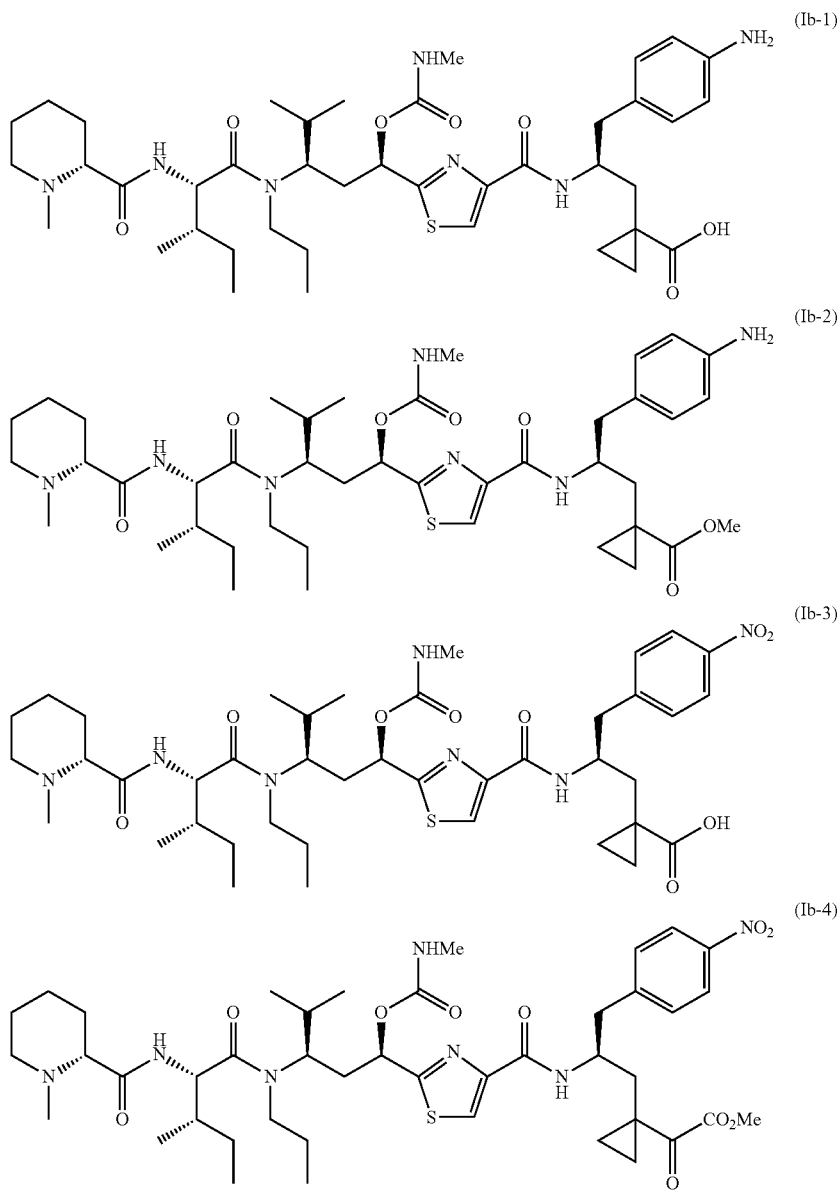

Figure 3:
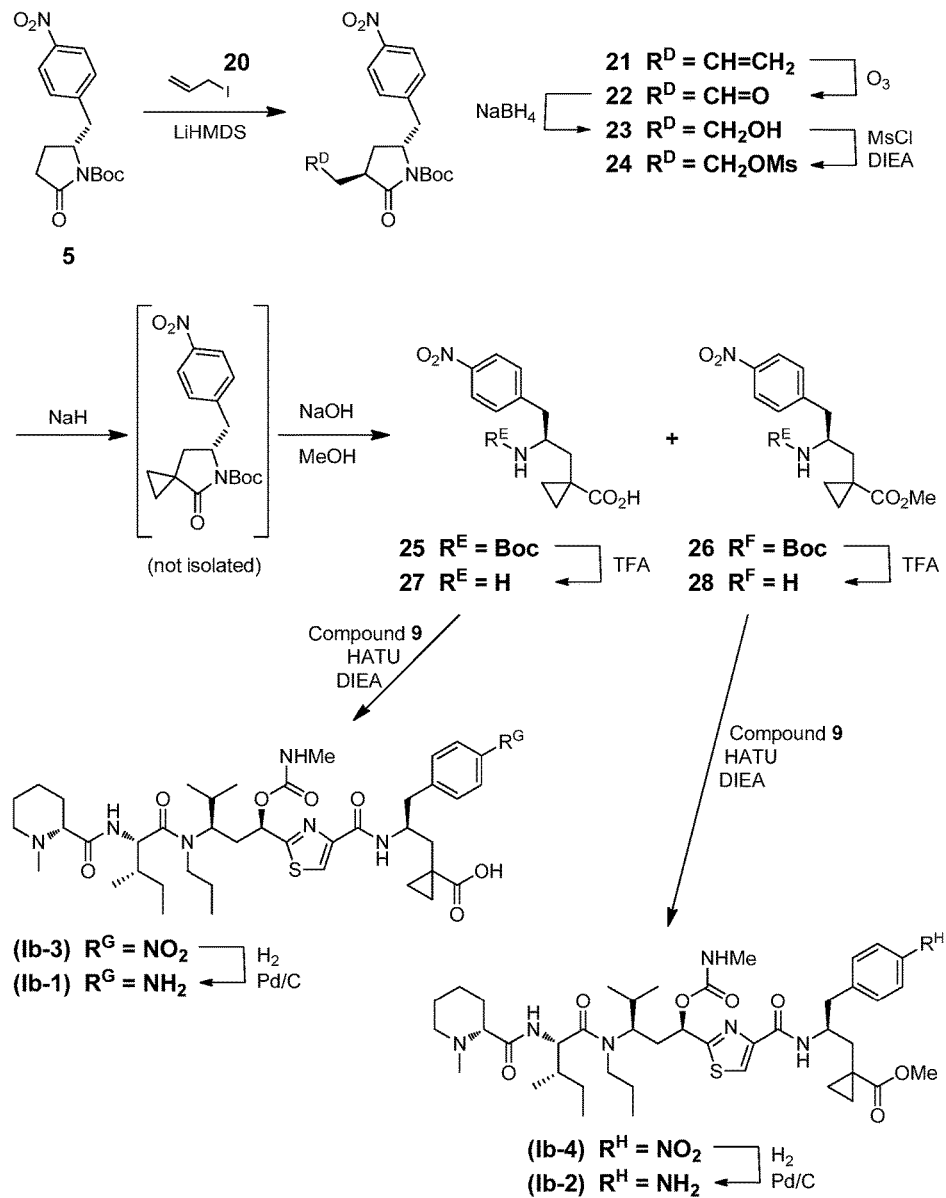
FIG. 3 shows a scheme for the synthesis of compounds (Ib-1) to (Ib-4).

The synthesis of compounds (Ib-1) to (Ib-4) is shown in the scheme of FIG. 3.

To a solution of (R)-tert-butyl 2-(4-nitrobenzyl)-5-oxopyrrolidine-1-carboxylate 5 (740 mg, 2.31 mmol) in THF (15 mL) at −78° C. was added LiHMDS (2.31 mL, 2.31 mmol, 1N toluene) dropwise. The brown solution was stirred at −78° C. for 30 min. A solution of 3-iodoprop-1-ene 20 (388 mg, 2.31 mmol) in 2 mL of THF was added dropwise. The reaction mixture was stirred at −78° C. for 7 h. The reaction was quenched by adding saturated aq. NaHCO$_3$ solution. After warming up to RT, the mixture was extracted with EtOAc (3×). The combined organic extracts were washed with brine, dried over anhydrous MgSO$_4$, filtered, and concentrated in vacuo to give a thick oil which was purified by silica gel flash chromatography (gradient from 0% to 50% EtOAc/hexanes) to afford (3S,5R)-tert-butyl 3-allyl-5-(4-nitrobenzyl)-2-oxopyrrolidine-1-carboxylate 21 (0.60 g, 72%) as a tan solid. $^1$H NMR (CDCl$_3$) δ 8.22 (d, J=8.8 Hz, 2H), 7.41 (d, J=8.8 Hz, 2H), 5.74 (ddt, J=17.2, 9.9, 7.0, 7.0 Hz, 1H), 5.03-5.12 (m, 2H), 4.36 (td, J=8.6, 3.5 Hz, 1H), 3.29 (dd, J=13.2, 3.5 Hz, 1H), 2.84 (dd, J=13.2, 9.5 Hz, 1H), 2.49-2.68 (m, 2H), 2.10-2.21 (m, 1H), 1.92 (dd, J=13.2, 8.6 Hz, 1H), 1.74 (td, J=12.4, 8.6 Hz, 1H), 1.60 (s, 9H). MS (ESI$^+$) m/z 743.5 (2M+Na)$^+$.

A solution of compound 21 (330 mg, 0.92 mmol) in DCM (6 mL) at −78° C. was bubbled with an O$_3$ stream until a blue color appeared (~3 min). The reaction mixture was flushed with O$_2$ for 5 min, and then N$_2$ for 5 min. DMSO (0.34 mL, 4.58 mmol) was added and the reaction mixture was warmed to RT and stirred at RT overnight. The reaction mixture was washed with water and brine. The organic layer was dried over anhydrous MgSO$_4$, filtered, and concentrated in vacuo to give a thick oil which was purified by silica gel flash chromatography (gradient from 0% to 70% EtOAc/DCM) to afford (3R,5R)-tert-butyl 5-(4-nitrobenzyl)-2-oxo-3-(2-oxoethyl)pyrrolidine-1-carboxylate 22 (0.26 g, 78%) as colorless oil. $^1$H NMR (CDCl$_3$) δ 9.76 (s, 1H), 8.16 (d, J=8.8 Hz, 2H), 7.40 (d, J=8.8 Hz, 2H), 4.35 (td, J=8.8, 3.6 Hz, 1H), 3.25 (dd, J=13.2, 3.6 Hz, 1H), 3.05 (dd, J=18.8, 4.2 Hz, 1H), 2.85-2.97 (m, 2H), 2.52 (dd, J=18.8, 8.2 Hz, 1H), 2.07-2.15 (m, 1H), 1.66 (td, J=12.5, 8.5 Hz, 1H), 1.54 (s, 9H). MS (ESI$^+$) m/z 747.5 (2M+Na)$^+$.

To a solution of compound 22 (259 mg, 0.72 mmol) in MeOH (5 mL) at 0° C. was added NaBH$_4$ (27.0 mg, 0.715 mmol). The reaction mixture was stirred at 0° C. for 20 h. The reaction was quenched by adding 10% aqueous citric acid and extracted with EtOAc (3×). The combined organic extracts were dried over anhydrous MgSO$_4$, filtered, and concentrated in vacuo. The residue was purified by silica gel flash chromatography (gradient from 0% to 80% EtOAc/DCM) to afford (3R,5R)-tert-butyl 3-(2-hydroxyethyl)-5-(4-nitrobenzyl)-2-oxopyrrolidine-1-carboxylate 23 (0.16 g, 60%) as a colorless oil. $^1$H NMR (CDCl$_3$) δ 8.15 (d, J=8.6 Hz, 2H), 7.39 (d, J=8.6 Hz, 2H), 4.33 (td, J=8.8, 3.6 Hz, 1H), 3.71-3.80 (m, 1H), 3.58-3.68 (m, 1H), 3.25 (dd, J=13.2, 3.6 Hz, 1H), 2.90 (br s, 1H), 2.83 (dd, J=13.2, 9.4 Hz, 1H), 2.64-2.74 (m, 1H), 1.95-2.06 (m, 2H), 1.68-1.79 (m, 1H), 1.59 (m, 1H), 1.54 (s, 9H). MS (ESI$^+$) m/z 751.5 (2M+Na)$^+$.

To a solution of compound 23 (156 mg, 0.43 mmol) in THF (4 mL) at RT was added mesyl chloride (0.043 mL, 0.58 mmol) and DIEA (0.097 mL, 0.56 mmol). The reaction mixture was stirred at RT for 3 h. The reaction mixture was diluted with DCM and washed with water. The organic layer was dried over anhydrous MgSO$_4$, filtered, and concentrated in vacuo. The residue was purified by silica gel flash chromatography (gradient from 0% to 60% EtOAc/DCM) to afford (3R,5R)-tert-butyl 3-(2-((methylsulfonyl)oxy)-ethyl)-5-(4-nitrobenzyl)-2-oxopyrrolidine-1-carboxylate 24 (0.17 g, 91%) as colorless oil. $^1$H NMR (CDCl$_3$) δ 8.20 (d, J=8.6 Hz, 2H), 7.42 (d, J=8.6 Hz, 2H), 4.29-4.45 (m, 2H), 3.26 (dd, J=13.0, 3.4 Hz, 1H), 3.02 (s, 3H), 2.88 (dd, J=13.2, 9.4 Hz, 1H), 2.59-2.69 (m, 1H), 2.30 (ddt, J=14.7, 7.0, 5.4, 5.4 Hz, 1H), 2.13 (dd, J=13.0, 8.3 Hz, 1H), 1.67-1.81 (m, 3H), 1.58 (s, 9H). MS (ESI$^+$) m/z 907.5 (2M+Na)$^+$.

To a solution of compound 24 (80 mg, 0.18 mmol) in DMF (1.0 mL) at 0° C. was added NaH (14.5 mg, 0.36 mmol). The reaction mixture was stirred at 0° C. for 1 h and RT for 2 h. To the reaction mixture was added THF, MeOH (0.5 mL each), and 3 eq. 1N aqueous NaOH solution. The reaction mixture was stirred at RT for 3 h. After cooling to 0° C., the pH of the reaction mixture was adjusted to pH 3-4 with 1N aq. HCl and then extracted with DCM (3×). The combined organic extracts were dried over anhydrous MgSO$_4$, filtered, and concentrated in vacuo. The residue was purified on a C18 Phenomenex Luna S5 ODS 30×100 mm reverse phase preparative HPLC column eluting with 10-90% aq CH$_3$CN containing 0.05% TFA over a 12 minute gradient). The following two compounds were isolated:

(S)-1-(2-((tert-Butoxycarbonyl)amino)-3-(4-nitrophenyl) propyl)cyclopropanecarboxylic acid 25 (20 mg, 30%). $^1$H NMR (CDCl$_3$) δ 8.15 (d, J=8.6 Hz, 2H), 7.37 (d, J=8.6 Hz, 2H), 4.11 (m, 1H), 2.79-3.03 (m, 2H), 1.38 (s, 9H), 1.30 (m, 2H), 0.86 (m, 2H), 0.76 (m, 2H). MS (ESI$^+$) m/z 751.6 (2M+Na)$^+$.

(S)-Methyl 1-(2-((tert-butoxycarbonyl)amino)-3-(4-nitrophenyl)propyl)cyclopropanecarboxylate 26 (20 mg, 29%). $^1$H NMR (CDCl$_3$) δ 8.15 (d, J=8.2 Hz, 2H), 7.36 (d, J=8.2 Hz, 2H), 4.05 (m, 1H), 2.80-3.02 (m, 2H), 1.82-1.93 (m, 2H), 1.38 (s, 9H), 0.74-0.82 (m, 2H), 0.62-0.71 (m, 2H). MS (ESI$^+$) m/z 379.1 (M+H)$^+$.

To a solution of cyclopropanecarboxylic acid 25 (20 mg, 0.055 mmol) in DCM (0.75 mL) was added TFA (0.25 mL). The reaction mixture was stirred at RT for 2 h and concentrated in vacuo. The product (S)-1-(2-amino-3-(4-nitrophenyl)propyl)cyclopropanecarboxylic acid 27 was obtained as its TFA salt and was used directly in the next reaction without purification (21 mg, 100%). $^1$H NMR (CD$_3$OD) δ 8.24 (d, J=8.8 Hz, 2H), 7.54 (d, J=8.80 Hz, 2H), 3.85-3.95 (m, 1H), 3.08 (dd, J=7.2, 2.2 Hz, 2H), 1.98-2.08 (m, 1H), 1.64 (dd, J=15.4, 4.2 Hz, 1H), 1.34-1.43 (m, 1H), 1.23-1.30 (m, 1H), 0.79-0.87 (m, 1H), 0.66 (m, 1H). MS (ESI$^+$) m/z 265.2 (M+H)$^+$.

Acid 27 was coupled with compound 9 to yield 1-((S)-2-(2-((5R,7R,10S)-10-((S)-sec-butyl)-7-isopropyl-12-((R)-1-methylpiperidin-2-yl)-3,9,12-trioxo-8-propyl-4-oxa-2,8,11-triazadodecan-5-yl)thiazole-4-carboxamido)-3-(4-nitrophenyl)propyl)cyclopropanecarboxylic acid (Ib-3), generally following the procedures described hereinabove. Then, compound (Ib-3) was converted to 1-((S)-3-(4-aminophenyl)-2-(2-((5R,7R,10S)-10-((S)-sec-butyl)-7-isopropyl-12-((R)-1-methylpiperidin-2-yl)-3,9,12-trioxo-8-propyl-4-oxa-2,8,11-triazadodecan-5-yl)thiazole-4-carboxamido) propyl)cyclopropanecarboxylic acid (Ib-1) by hydrogenation as described above (5 mg, 47%) as a white solid. $^1$H NMR (CD$_3$OD) δ 8.03 (s, 1H), 7.32 (d, J=8.2 Hz, 2H), 7.11 (d, J=8.2 Hz, 2H), 4.60-4.73 (m, 2H), 3.75 (d, J=10.1 Hz, 1H), 3.43 (m, 2H), 2.83-2.97 (m, 6H), 2.74 (s, 3H), 2.70 (s, 3H), 2.12-2.30 (m, 3H), 1.93 (m, 3H), 1.78 (m, 2H), 1.58 (m, 4H), 1.10-1.27 (m, 3H), 0.91-1.06 (m, 18H), 0.83-0.90 (m, 2H), 0.75 (m, 2H). MS (ESI$^+$) m/z 798.7 (M+H)$^+$.

To a solution of methyl ester 26 (20 mg, 0.053 mmol) in DCM (0.75 mL) was added TFA (0.25 mL). The reaction mixture was stirred at RT for 2 h and then concentrated in vacuo. The product (S)-methyl 1-(2-amino-3-(4-nitrophenyl)propyl)cyclopropanecarboxylate 28 was obtained as its TFA salt and was used in the next reaction without purification (21 mg, 100%). $^1$H NMR (CD$_3$OD) δ 8.25 (d, J=8.8 Hz, 2H), 7.54 (d, J=8.8 Hz, 2H), 3.87-3.98 (m, 1H), 3.65 (s, 3H), 3.08 (dd, J=7.2, 5.0 Hz, 2H), 1.96 (dd, J=15.2, 8.6 Hz, 1H), 1.75 (dd, J=15.2, 4.6 Hz, 1H), 1.34-1.42 (m, 1H), 1.22-1.30 (m, 1H), 0.86 (ddd, J=9.4, 6.8, 4.1 Hz, 1H), 0.73 (ddd, J=9.4, 6.8, 4.1 Hz, 1H). MS (ESI$^+$) m/z 279.2 (M+H)$^+$.

Methyl ester 28 was coupled with compound 9 to yield methyl 1-((S)-2-(2-((5R,7R,10S)-10-((S)-sec-butyl)-7-isopropyl-12-((R)-1-methylpiperidin-2-yl)-3,9,12-trioxo-8-propyl-4-oxa-2,8,11-triazadodecan-5-yl)thiazole-4-carboxamido)-3-(4-nitrophenyl)propyl)-cyclopropanecarboxylate (Ib-4), following the procedures hereinabove. Methyl ester (Ib-4) was converted to methyl 1-((S)-3-(4-aminophenyl)-2-(2-((5R,7R,10S)-10-((S)-sec-butyl)-7-isopropyl-12-((R)-1-methylpiperidin-2-yl)-3,9,12-trioxo-8-propyl-4-oxa-2,8,11-triazadodecan-5-yl)thiazole-4-carboxamido)propyl) cyclopropanecarboxylate (Ib-2) by hydrogenation per the previous example (9 mg, 59%) as a white solid. $^1$H NMR (CD$_3$OD) δ 8.06 (s, 1H), 7.41 (d, J=8.4 Hz, 2H), 7.24 (d, J=8.4 Hz, 2H), 5.68 (d, J=12.4 Hz, 1H), 4.64 (d, J=8.6 Hz, 2H), 3.81 (d, J=10.7 Hz, 1H), 3.71 (t, J=11.1 Hz, 1H), 3.58 (s, 3H), 3.49 (d, J=11.1 Hz, 1H), 3.05-3.20 (m, 3H), 2.91-2.96 (m, 3H), 2.80 (s, 3H), 2.71 (s, 3H), 2.21 (m, 1H), 1.90-2.07 (m, 5H), 1.75-1.87 (m, 4H), 1.56-1.69 (m, 3H), 1.14 (m, 3H), 0.96-1.04 (m, 16H), 0.88 (m, 2H), 0.71-0.78 (m, 2H). MS (ESI$^+$) m/z 812.7 (M+H)$^+$.

Example 5—Compound (Ic-1)

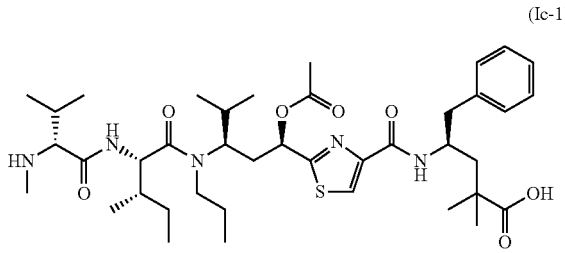

Figure 4:
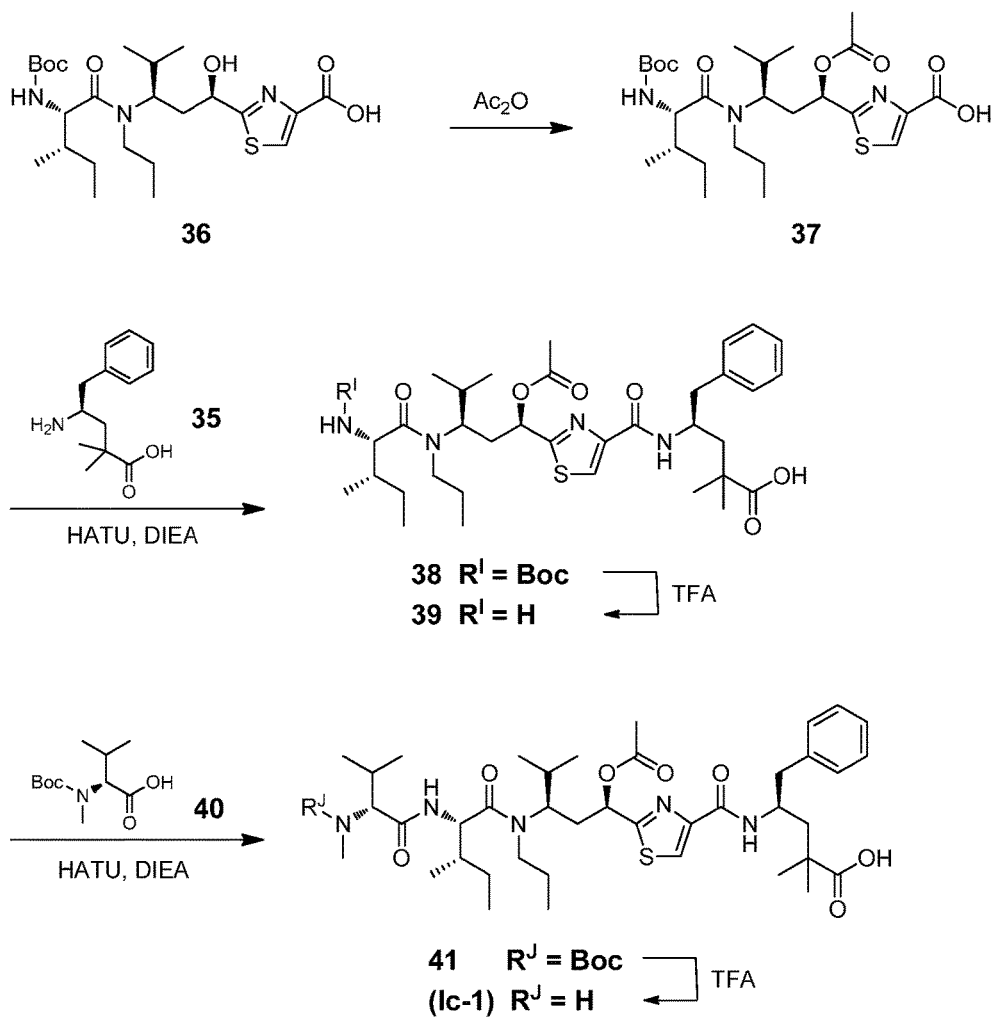
FIG. 4 shows a scheme for the synthesis of compound (Ic-1).

The synthesis of compound (Ic-1) is shown in the scheme of FIG. 4.

Generally following the procedures hereinabove, Boc-protected phenylalanine 34 was converted to (S)-4-amino-2,2-dimethyl-5-phenylpentanoic acid 35, which was used as precursor in this example, (0.265 gm, 70%) as a solid TFA salt. $^1$H NMR (400 MHz, DMSO-$d_6$) δ 12.62 (br. s., 1H), 7.74 (br. s., 2H), 7.43-7.09 (m, 5H), 3.47-3.35 (m, 1H), 2.91-2.70 (m, 2H), 1.81-1.56 (m, 2H), 1.10-0.95 (m, 6H); MS (ESI$^+$) m/z 222.1 (M+H)$^+$.

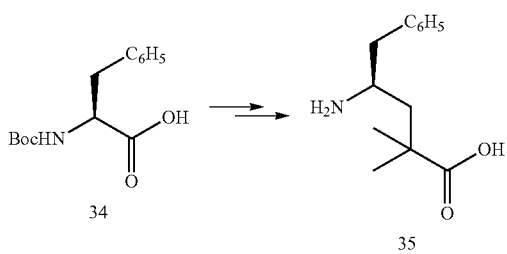

2-((1R,3R)-3-((2S,3S)-2-((tert-butoxycarbonyl)amino)-3-methyl-N-propylpentanamido)-1-hydroxy-4-methylpentyl)thiazole-4-carboxylic acid 36 was prepared by generally following the scheme and conditions of FIG. 1 of Cong et al. 2014, mutatis mutandis. A sample of it (0.0555 g, 0.111 mmol) was dissolved in THF (1 mL) with DMAP (0.027 g, 0.222 mmol) and the resulting solution then treated with acetic anhydride (0.021 mL, 0.222 mmol) at RT. Pyridine (0.193 µL, 0.222 mmol) was then added and the resulting reaction mixture then stirred at RT for 2 h. The reaction mixture was quenched with 1N HCl and the solution extracted with DCM (3×). The combined organic extracts were dried with anhydrous Na$_2$SO$_4$, filtered and the filtrate concentrated in vacuo to afford 2-((6S,9R,11R)-6-((S)-sec-butyl)-9-isopropyl-2,2-dimethyl-4,7,13-trioxo-8-propyl-3,12-dioxa-5,8-diazatetradecan-11-yl)thiazole-4-carboxylic acid 37 (0.064 gm, 100%) as a solid. The product was used in the next step without further purification. $^1$H NMR (400 MHz, DMSO-$d_6$) δ 8.42 (s, 1H), 7.00-6.78 (m, 1H), 5.62 (d, J=11.0 Hz, 1H), 4.24 (d, J=7.3 Hz, 1H), 4.09-3.94 (m, 1H), 3.01-2.80 (m, 2H), 2.29-2.11 (m, 3H), 1.93 (br. s., 3H), 1.86-1.66 (m, 4H), 1.60-1.47 (m, 1H), 1.42-1.28 (m, 9H), 1.00-0.59 (m, 15H); MS (ESI$^+$) m/z 542.2 (M+H)$^+$.

Acid 37 (0.063 g, 0.116 mmol) and HATU (0.053 g, 0.140 mmol) were dissolved in DMF (1 mL) and the resulting solution was treated with DIEA (0.101 mL, 0.582 mmol) at RT. The reaction mixture was stirred at RT for 30 minutes. A DMF (1 mL) solution of (S)-4-amino-2,2-dimethyl-5-phenylpentanoic acid 35, TFA salt (0.039 g, 0.116 mmol) with DIEA (0.101 mL, 0.582 mmol) was added to the activated ester and the resulting reaction mixture was stirred at RT for 1 h. The reaction mixture was then purified by wet loading on a C-18 reverse phase ISCO system, eluting with 50-100% aq. CH$_3$CN with 0.1% TFA over a 13 minute gradient. The appropriate fractions were isolated and freeze dried to afford (S)-4-(2-((6S,9R,11R)-6-((S)-sec-butyl)-9-isopropyl-2,2-dimethyl-4,7,13-trioxo-8-propyl-3,12-dioxa-5,8-diazatetradecan-11-yl)thiazole-4-carboxamido)-2,2-dimethyl-5-phenylpentanoic acid 38 (0.053 gm, 61%) as a solid. MS (ESI$^+$) m/z 745.4 (M+H)$^+$.

Acid 38 (0.053 g, 0.071 mmol) was dissolved in DCM (1.25 mL) and the resulting solution was then treated with TFA (0.4 mL) at RT. The reaction mixture was stirred at RT for 1 h then concentrated in vacuo. The residue was purified on a C-18 reverse phase 50 gm Gold ISCO column, eluting with 10-100% aq. CH$_3$CN with 0.1% TFA over a 14 minute gradient. The appropriate fractions were isolated and freeze dried to afford (S)-4-(2-((1R,3R)-1-acetoxy-3-((2S,3S)-2-amino-3-methyl-N-propylpentanamido)-4-methylpentyl)thiazole-4-carboxamido)-2,2-dimethyl-5-phenylpentanoic acid 39, TFA salt (0.032 gm, 67%) as a white solid. $^1$H NMR (400 MHz, DMSO-$d_6$) δ 8.17-8.09 (m, 1H), 7.32-7.06 (m, 5H), 5.72-5.40 (m, 1H), 4.27 (d, J=6.6 Hz, 1H), 4.02-3.87 (m, 2H), 3.56 (br. s., 1H), 3.20 (d, J=11.9 Hz, 1H), 3.04 (t, J=11.3 Hz, 1H), 2.91-2.72 (m, 2H), 2.42-2.28 (m, 2H), 2.15-2.09 (m, 3H), 2.00 (br. s., 1H), 1.93-1.85 (m, 1H), 1.82-1.71 (m, 2H), 1.62-1.46 (m, 2H), 1.13-0.75 (m, 24H); MS (ESI$^+$) m/z 645.4 (M+H)$^+$.

(R)-2-((tert-butoxycarbonyl)(methyl)amino)-3-methylbutanoic acid 40 (CAS Reg. No. 89536-85-6, 2.93 mg, 0.013 mmol) and HATU (4.81 mg, 0.013 mmol) were dissolved in DMF (0.5 mL) and the resulting solution was then treated with DIEA (7.34 µL, 0.042 mmol) at RT. The reaction mixture was stirred at RT for 30 minutes. Acid 39, TFA salt (0.008 g, 10.54 µmol) dissolved in DMF (0.5 mL) along with DIEA (7.34 µL, 0.042 mmol) was then added to the activated ester and the resulting reaction mixture was stirred at RT for 1 h. The reaction mixture was purified by wet loading on an ISCO 50 gm gold reverse phase C-18 column, eluting 50-100% aq. CH$_3$CN with 0.1% TFA over a 13 minute gradient. The appropriate fractions were isolated and freeze dried to afford (S)-4-(2-((6R,9S,12R,14R)-9-((S)-sec-butyl)-6,12-diisopropyl-2,2,5-trimethyl-4,7,10,16-tetraoxo-11-propyl-3,15-dioxa-5,8,11-triazaheptadecan-14-yl)thiazole-4-carboxamido)-2,2-dimethyl-5-phenylpentanoic acid 41 (0.009 gm, 95%) as a solid. MS (ESI$^+$) m/z 858.4 (M+H)$^+$.

A solution of acid 41 (0.008 g, 9.32 µmol) in DCM (1 mL) was treated at RT with TFA (0.3 mL). The reaction mixture was stirred RT for 1 h and concentrated in vacuo. The residue was purified by C-18 HPLC eluting on a C18 21×100 mm column with 9.5-95% aq. CH$_3$CN with 0.1% TFA over a 12 minute gradient. The appropriate fractions were isolated and freeze dried to afford (S)-4-(2-((3R,6S,9R,11R)-6-((S)-sec-butyl)-3,9-diisopropyl-4,7,13-trioxo-8-propyl-12-oxa-2,5,8-triazatetradecan-11-yl)thiazole-4-carboxamido)-2,2-dimethyl-5-phenylpentanoic acid (Ic-1) (0.005 gm, 62%) as a TFA salt. $^1$H NMR (400 MHz, CD$_3$OD) δ 8.07 (s, 1H), 7.81 (d, J=9.7 Hz, 1H), 7.35-7.07 (m, 5H), 5.75 (d, J=11.2 Hz, 1H), 4.70 (d, J=8.1 Hz, 1H), 4.45 (br. s., 1H), 3.65 (d, J=4.6 Hz, 1H), 3.19-3.06 (m, 1H), 2.96-2.65 (m, 4H), 2.52 (s, 3H), 2.39-2.30 (m, 1H), 2.27-2.04 (m, 6H), 1.94-1.86 (m, 2H), 1.72-1.54 (m, 3H), 1.32-0.77 (m, 31H); MS (ESI$^+$) m/z 758.4 (M+H)$^+$.

Example 6—Compound (Ic-2)

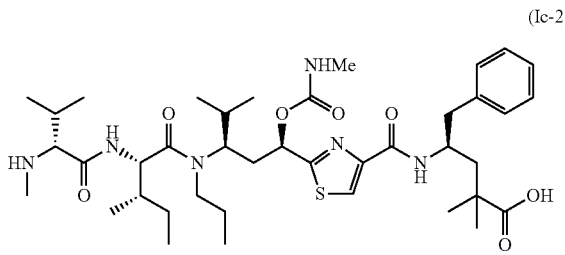

(Ic-2)

Figure 5A:
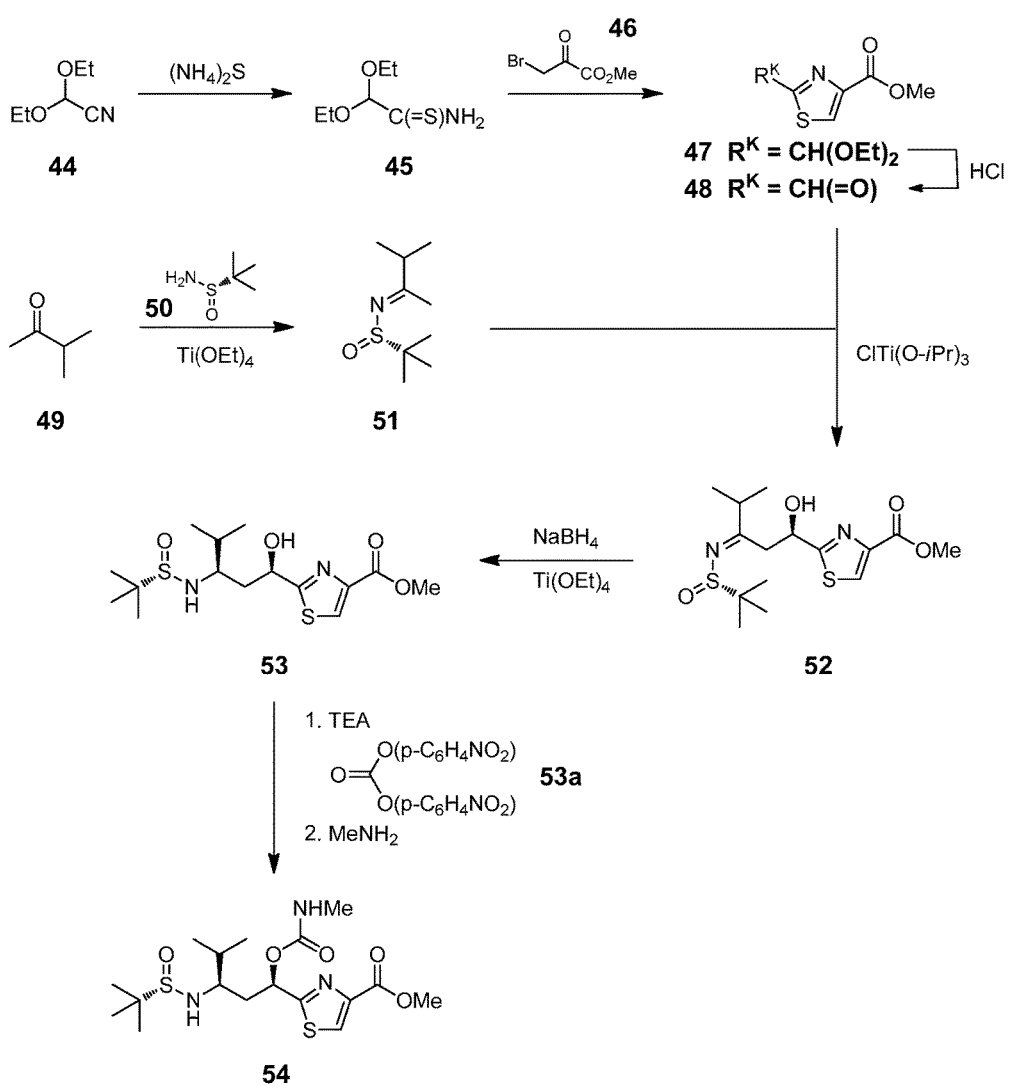
FIGS. 5a and 5b show, in combination, a scheme for the synthesis of compound (Ic-2).
Figure 5B:
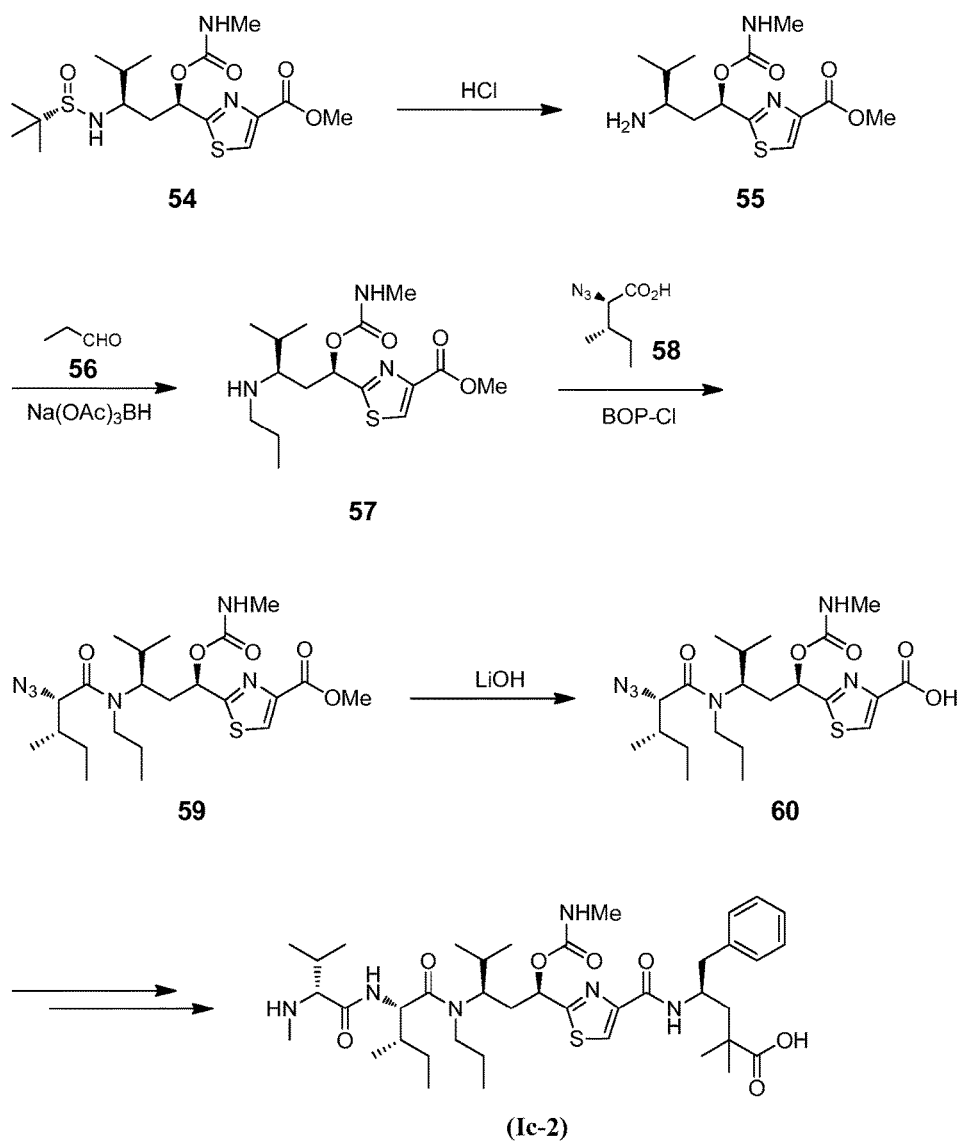

Compound (Ic-2) was prepared analogously to compound (Ic-1) using, as a precursor material, compound 60, whose synthesis is shown schematically in FIGS. 5a-5b.

To a solution of 2,2-diethoxyacetonitrile 44 (50 g, 387 mmol) in methanol (2.0 L) was added ammonium sulfide solution (50% aq.) (52.8 mL, 387 mmol). The reaction mixture was stirred at RT overnight. The reaction mixture was concentrated in vacuo to remove volatiles. The brown pasty residue was dissolved in ethyl acetate and the organic solution then washed with water and brine. The organic fraction was separated and dried with anhydrous $Na_2SO_4$ and filtered. The filtrate was concentrated in vacuo to afford a yellow solid. The solid was triturated with petroleum ether, filtered and the solid dried under high vacuum to afford 2,2-diethoxyethanethioamide 45 (35 g, 55.4%) as a white solid. $^1$H NMR ($CDCl_3$) (400 MHz) δ 1.27-1.24 (two merging triplets, 3H each, J=7.2 Hz), 3.78-3.61 (two merging quartets, 2H each, J=7.2 Hz), 5.04 (s, 1H), 7.61 & 7.86 (br. peak, 2H).

A mixture of thioamide 45 (50 g, 306 mmol) dissolved in methanol (450 mL) and size 3A molecular sieves (120 g) was heated with stirring to 65° C. Methyl bromopyruvate 46 (32.6 mL, 306 mmol) was added drop-wise over 15 min and the resulting reaction mixture was stirred at 65° C. for 3 h. The reaction mixture was cooled to RT and the brown solid that formed was filtered off and discarded. The filtrate was concentrated in vacuo to afford a black oil. The oil was dissolved in DCM and filtered through a pad of silica (60-120 mesh) and the filtrate concentrated in vacuo. The crude methyl 2-(diethoxymethyl)thiazole-4-carboxylate 47 (50 g, 66.5%, oil), was taken on to the next step without further purification.

A solution of ester 47 (50 g, 204 mmol) in acetone (1.5 L) was treated with 1.5 N HCl (1.0 L) drop wise at 50° C. The mixture was then heated at 60° C. for 3 h. The reaction mixture was cooled to RT and the solution was and extracted with ethyl acetate (3×). The combined organic layers were separated and the organic fraction washed with saturated aq. NaCl. The organic fraction was separated and dried with anhydrous $Na_2SO_4$ and filtered. The filtrate was concentrated in vacuo. The residue was purified by flash chromatography (230-400 mesh silica) with a gradient of 15-20% EtOAc-petroleum ether. The appropriate fractions were isolated and concentrated in vacuo to afford methyl 2-formylthiazole-4-carboxylate 48 (12 g., 34.4%) as a pare yellow solid. $^1$H NMR ($CDCl_3$) (400 MHz) δ 4.02 (s, 3H), 8.54 (d, 1H, J=1.2 Hz), 10.07 (d, 1H, J=1.2 Hz).

A solution of 3-methylbutan-2-one 49 (50 g, 580 mmol) and titanium tetraethoxide (265 g, 1160 mmol) in anhydrous THF (750 mL) was stirred under a nitrogen atmosphere in a round bottom flask at RT. (S)-t-Butyl sulfinimide 50 (70.4 g, 0.58 m) was added to the reaction mixture and the resulting reaction mixture was stirred at 70° C. overnight. The reaction mixture was cooled to RT and quenched with saturated aq. NaCl (500 mL). The resulting solution was stirred for 10 min and the mixture filtered through a CELITE™ pad. The pad was washed thoroughly with ethyl acetate, and the filtrate extracted with ethyl acetate (2×). The combined organic extracts were dried with anhydrous $Na_2SO_4$ and filtered. The filtrate concentrated in vacuo. The residue was purified by flash chromatography (230-400 mesh silica) with a gradient of 10-20% EtOAc-petroleum ether mixture to afford (R,E)-2-methyl-N-(3-methylbutan-2-ylidene)propane-2-sulfinamide 51 (70 g, 63.5%) as a yellow oil. $^1$H NMR ($CDCl_3$) (400 MHz) δ 1.14-1.11 (m, 6H), 1.23 (s, 9H), 2.31 (s, 3H), 2.57-2.52 (m, 1H).

A solution of DIEA (15.8 mL, 110 mmol) in anhydrous ether (200 mL) was cooled to −78° C. n-BuLi (2M, 55 ml, 110 mmol) was added drop wise. The resulting mixture was warmed to 0° C. then continued to be stirred for 45 min at 0° C. The mixture was recooled to −78° C. and a solution of sulfinamide 51 (10 g, 52 mmol) in ether (100 mL) was added dropwise. The reaction mixture and stirred at −78° C. for 1 h. Chlorotitanium triisopropoxide (31.7 g, 121 mmol) was added and resulting reaction mixture was continue stirred at −78° C. for 1 h. Compound 48 (9 g, 52 mmol) was added in one portion and the resulting reaction mixture was continue stirred at −78° C. overnight. The reaction mixture was quenched with 20% acetic acid in THF and allowed to warm to RT. Water (2.5 mL) was added and the resulting solution was filtered through a pad of CELITE™. The pad was washed thoroughly with ethyl acetate. The filtrate was extracted with ethyl acetate (3×). The combined organic extracts were washed 1× with saturated aq. NaCl. The organic fraction was dried with anhydrous $Na_2SO_4$ and filtered. The filtrate concentrated in vacuo. The residue was purified by flash chromatography (230-400 mesh silica) with a gradient of 15-20% ethylacetate-petroleum ether mixture to afford methyl 2-((R,E)-3-(((R)-tert-butylsulfinyl)imino)-1-hydroxy-4-methylpentyl)thiazole-4-carboxylate 52 (9.0 g, 47%) as a pale yellow viscous oil. $^1$H NMR ($CDCl_3$) (400 MHz) δ 1.17-1.06 (m, 6H), 1.23 (s, 9H), 2.88-2.84 (m, 1H), 3.37-3.34 (m, 2H), 3.94 (s, 3H), 5.17-5.09 (m, 1H), 6.63 (d, 1H, J=13.2 Hz), 8.16-8.13 (d, 1H, J=13.2 Hz); MS (ESI$^+$) m/z 361.0 (M+H)$^+$.

A solution of compound 52 (30 g, 83 mmol) in THF (300 mL) was cooled to −78° C. Titanium tetraethoxide (38 g, 166 mmol) was then added to the solution followed by portion-wise addition of $NaBH_4$ (12.6 g, 330 mmol). The mixture was stirred at −78° C. for 3 h. The reaction mixture was quenched with methanol (10 mL) followed by 20% acetic acid in THF (100 mL) and allowed then allowed to warm to RT. Water (50 mL) was added and the resulting solution was filtered over a pad of CELITE™. The pad was washed thoroughly with ethyl acetate. The filtrate was extracted with ethyl acetate (3×). The combined organic extracts were washed 1× with saturated aq. NaCl and dried with anhydrous $Na_2SO_4$. The filtrate was concentrated in vacuo. The residue was purified by flash silica gel chromatography eluting 40-50% gradient of ethylacetate in petroleum ether. The appropriate fractions were isolated and concentrated in vacuo to afford methyl 2-((1R,3R)-3-((S)-1,1-dimethylethylsulfinamido)-1-hydroxy-4-methylpentyl)thiazole-4-carboxylate 53 (20 g, 64%) as a solid. $^1$H NMR ($CDCl_3$) (400 MHz) δ 0.90-0.80 (m, 6H), 1.30 (s, 9H), 1.73-1.68 (m, 1H), 1.94-1.89 (m, 1H), 2.30-2.23 (m, 1H), 3.47-3.37 (m, 2H), 3.93 (s, 3H), 5.21-5.18 (m, 1H), 5.58-5.57 (m, 1H), 8.12 (s, 1H). MS (ESI$^+$) m/z 363.1 (M+H)$^+$.

Compound 53 (3.15 g, 8.69 mmol) was dissolved in DCM (65 mL) along with bis(4-nitrophenyl) carbonate 53a (CAS Reg. No. 5070-13-3, 5.29 g, 17.38 mmol). The resulting solution was then treated with triethylamine (3.03 mL, 21.72 mmol) and then the resulting reaction mixture was allowed to stir at RT overnight, turning yellow. The reaction mixture was then treated with methanamine (19.55 mL, 39.1 mmol) (2M in THF) at RT and the resulting reaction mixture was stirred at RT for 30 min. The orange slurry was filtered through a CELITE™ pad, which was washed with DCM. The filtrate was concentrated in vacuo and the residue purified by ISCO chromatography, eluting with 0-8.5% MeOH/DCM over a 20 min gradient. The appropriate fractions were vacuum concentrated in vacuo. The residue was dissolved in ethyl acetate and the solution washed 4× with 1N NaOH. The organic fraction was dried with anhydrous $Na_2SO_4$, filtered and concentrated in vacuo to afford clean compound 54 (3.1 gm, 78%), as a solid; MS (ESI$^+$) m/z 420.3 (M+H)$^+$.

Methyl carboxylate 54 (3.1 g, 7.39 mmol) was dissolved in MeOH (36.9 mL) and the resulting solution was treated with 4N HCl (1.85 mL, 7.39 mmol) in dioxane at RT stirred for 1 h. The reaction mixture was then concentrated in vacuo to afford crude methyl 2-((1R,3R)-3-amino-4-methyl-1-((methylcarbamoyl)oxy)pentyl)thiazole-4-carboxylate 55 (2.6 g, 95%) as its solid hydrochloride salt. MS(ESI$^+$) m/z 316.3 (M+H)$^+$.

To a 0° C. solution of compound 55 (1.85 g, 5.85 mmol) in DCM (29.2 mL) was added 4 Å molecular sieves followed by propionaldehyde 56 (0.422 mL, 5.85 mmol). After stirring at 0° C. for 45 min, sodium triacetoxyborohydride (1.86 g, 8.77 mmol) was added and the reaction mixture was stirred at 0° C. for 30 min. The reaction mixture was quenched with saturated aqueous $NaHCO_3$ solution and allowed to warm to RT. After 20 min gas evolution ceased and the solution was then extracted 3× with DCM. The combined organic extracts were dried over anhydrous $Na_2SO_4$, filtered and concentrated in vacuo to afford methyl 2-((1R,3R)-4-methyl-1-((methylcarbamoyl)oxy)-3-(propylamino)pentyl)thiazole-4-carboxylate 57 (2.05 g, 93%) as a solid. MS(ESI$^+$) m/z 358.5 (M+H)$^+$.

Compound 57 (1.00 g, 2.80 mmol) and (2S,3S)-2-azido-3-methylpentanoic acid 58 (0.440 g, 2.80 mmol; Peltier et al. 2006) were stirred together in DCM (14.0 mL). Bis(2-oxooxazolidin-3-yl)phosphinic chloride (0.855 g, 3.36 mmol) was added at RT followed by DIEA (1.46 mL, 8.39 mmol. The resulting reaction mixture was then stirred at RT overnight. The reaction mixture was quenched with 1N aqueous HCl solution and the mixture was extracted with DCM (3×). The combined organic extracts were then washed 3× with 10% aqueous $NaHCO_3$ solution. The organic fraction was dried over anhydrous $Na_2SO_4$, filtered and concentrated in vacuo. The solid product was found to be contaminated with about 25% of an impurity that was separated in a later step, giving methyl 2-((1R,3R)-3-((2S,3S)-2-azido-3-methyl-N-propylpentanamido)-4-methyl-1-((methylcarbamoyl)oxy)-pentyl)thiazole-4-carboxylate 59 (1.4 g, 76%) as a solid. MS(ESI$^+$) m/z 497.4 (M+H)$^+$.

Methyl ester 59 (1.39 g, 2.80 mmol) was dissolved in 1/1 MeOH (7.00 mL)/THF (7.00 mL) and the resulting solution was then treated at RT with 2N aqueous lithium hydroxide solution (2.80 mL, 5.60 mmol). The resulting reaction mixture was then stirred at RT for 12 h. The reaction mixture was concentrated in vacuo to remove any volatiles. The residue was treated with 1N aqueous HCl solution and the mixture was extracted with DCM (3×). The combined organic extracts were dried over anhydrous $Na_2SO_4$, filtered and concentrated in vacuo to afford 2-((1R,3R)-3-((2S,3S)-2-azido-3-methyl-N-propylpentanamido)-4-methyl-1-((methylcarbamoyl)oxy)pentyl)thiazole-4-carboxylic acid 60, still containing the impurity (1.4 g, 76%) as a solid. MS(ESI$^+$) m/z 483.5 (M+H)$^+$.

Coupling of pentanoic acid 35 and butanoic acid 40 to compound 60 introduce the Tup and Mep fragments, respectively, led to compound (Ic-2). The analytical data for compound (Ic-2) was as follows: $^1$H NMR (400 MHz, acetonitrile-d$_3$) δ 7.99-7.85 (m, 1H), 7.42-7.07 (m, 5H), 5.45 (d, J=10.1 Hz, 1H), 4.86-4.65 (m, 1H), 4.43-4.15 (m, 1H), 3.47-3.25 (m, 3H), 3.17-2.75 (m, 4H), 2.78-2.67 (m, 3H), 2.44-2.30 (m, 7H), 1.84-1.70 (m, 4H), 1.64-1.45 (m, 3H), 1.30-0.72 (m, 26H); MS (ESI$^+$) m/z 773.3 (M+H)$^+$.

Example 7—Compound (IIIa-2)

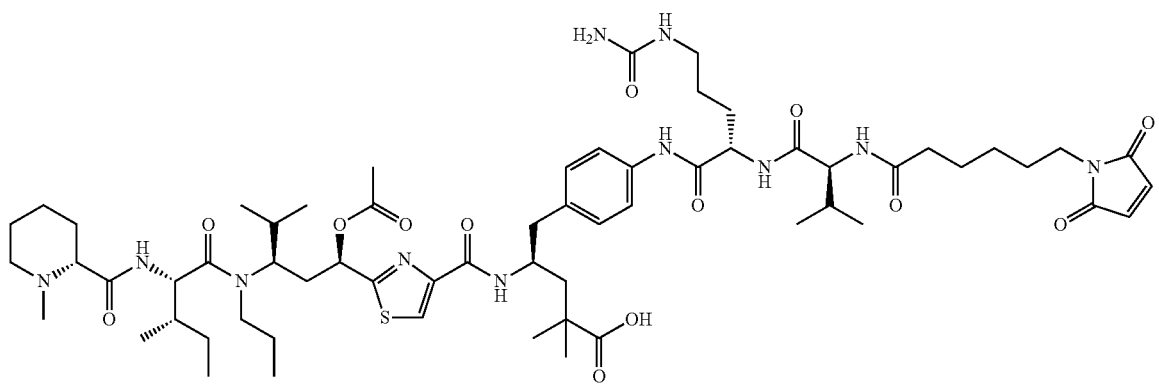

(IIIa-2)

Figure 6:
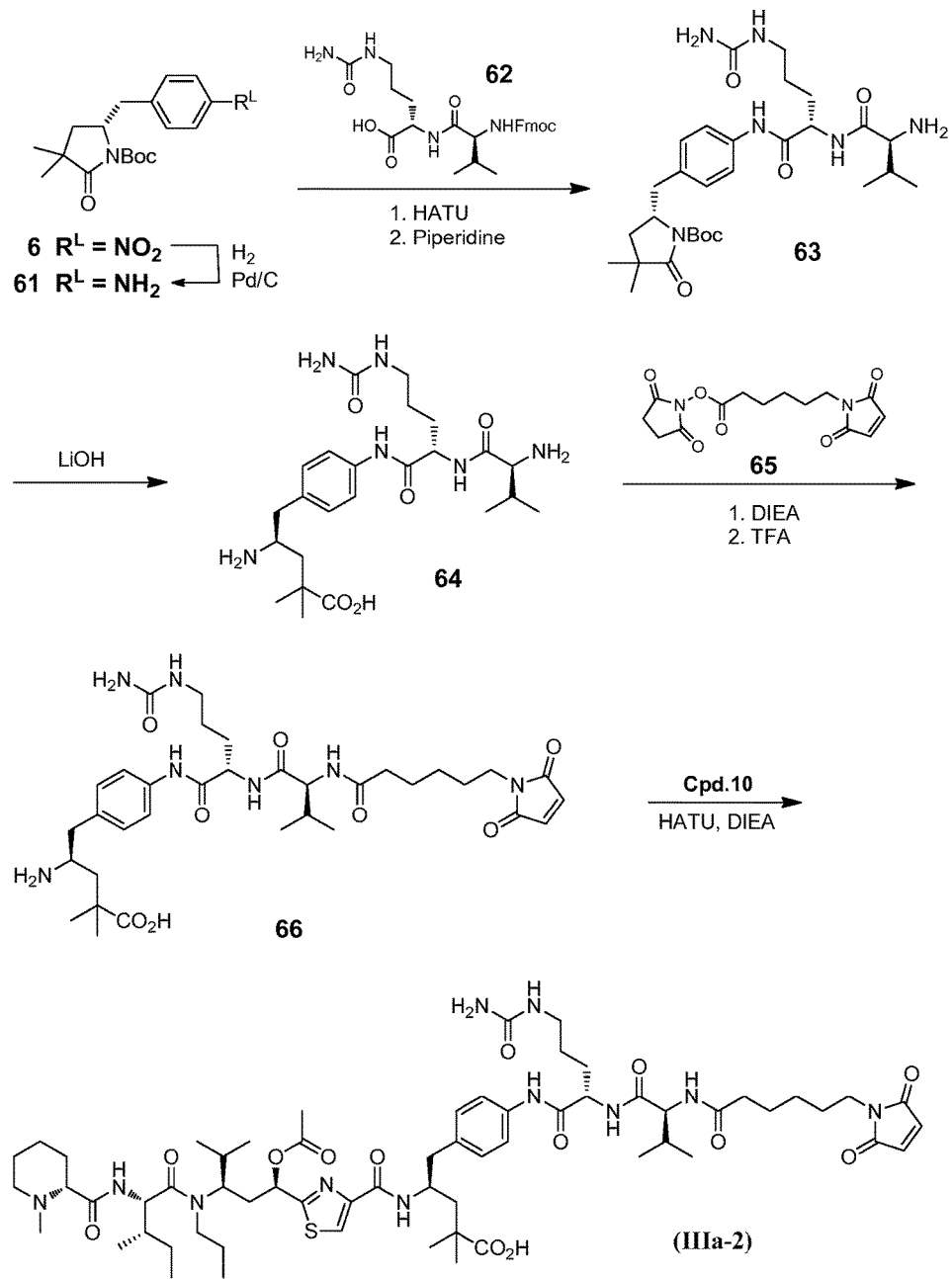
FIG. 6 shows a scheme for the synthesis of analog-linker compound (IIIa-2).

FIG. 6 shows schematically the preparation of compound (IIIa-2).

To a solution of compound 6 (FIG. 1 and Example 6, 420 mg, 1.206 mmol) in MeOH (10 mL) under nitrogen was added Pd/C (128 mg, 0.121 mmol, Aldrich). The reaction was placed under an $H_2$ atmosphere (balloon) and stirred for 3.0 h. The reaction vessel was flushed with nitrogen and CELITE™ was added. The mixture was filtered through a thin pad of CELITE™ and washed with MeOH. The filtrate was concentrated to give (S)-tert-butyl 5-(4-aminobenzyl)-

3,3-dimethyl-2-oxopyrrolidine-1-carboxylate 61 as a light yellow solid (382 mg, 100%). $^1$H NMR (400 MHz, CDCl$_3$) δ 6.99 (d, J=8.3 Hz, 1H), 6.66 (d, J=8.3 Hz, 1H), 4.15 (m, 1H), 3.64 (s, 2H), 3.34 (dd, J=13.1, 3.4 Hz, 1H), 2.53 (dd, J=13.1, 10.0 Hz, 1H), 1.86-1.76 (m, 1H), 1.72-1.64 (m, 1H), 1.61 (s, 9H), 1.22 (s, 3H), 1.16 (s, 3H); MS (ESI$^+$) m/z 659.6 (2M+Na)$^+$.

To a solution of compound 61 (382 mg, 1.20 mmol) and (S)-2-((S)-2-((((9H-fluoren-9-yl)methoxy)carbonyl)amino)-3-methylbutanamido)-5-ureidopentanoic acid 62 (CAS Reg. No. 557095-84-8, 596 mg, 1.20 mmol) in DMF (5 mL) at 0° C. were added HATU (593 mg, 1.560 mmol) and 2,6-dimethylpyridine (193 mg, 1.800 mmol). The reaction mixture was stirred at RT for 1.5 h. Cold water (50 mL) was added. The solid formed was collected by filtration, washed with water, and dried under vacuum to give a tan solid that was used for next reaction directly. MS (ESI$^+$) m/z 797.5 (M+H)$^+$.

To a solution of the above compound in THF (10 mL) and DMF (5 mL) was added piperidine (0.570 mL, 5.76 mmol). The reaction mixture was stirring at RT for 1 h. The reaction was concentrated in vacuo. The residue was suspended in MeOH. The white solid formed was removed by filtration. The filtrate was concentrated and purified by flash chromatography to give (S)-tert-butyl 5-(4-((S)-2-((S)-2-amino-3-methylbutanamido)-5-ureidopentanamido)benzyl)-3,3-dimethyl-2-oxopyrrolidine-1-carboxylate 63 as a colorless foamy solid (610 mg, 92% yield for two steps). $^1$H NMR (400 MHz, CDCl$_3$) δ 9.27 (s, 1H), 8.10 (d, J=8.7 Hz, 1H), 7.58 (d, J=8.4 Hz, 2H), 7.13 (d, J=8.4 Hz, 2H), 5.25 (br. s., 1H), 4.82 (td, J=9.0, 4.3 Hz, 1H), 4.61 (br. s., 2H), 4.25-4.14 (m, 1H), 3.54 (dd, J=14.3, 6.8 Hz, 1H), 3.40 (dd, J=13.1, 3.3 Hz, 1H), 3.32 (d, J=4.0 Hz, 1H), 3.24 (dd, J=14.3, 5.7 Hz, 1H), 2.61 (dd, J=13.1, 9.8 Hz, 1H), 2.31 (td, J=6.8, 4.0 Hz, 1H), 2.01 (dd, J=13.8, 4.7 Hz, 1H), 1.84-1.75 (m, 2H), 1.74-1.63 (m, 5H), 1.61 (s, 9H), 1.21 (s, 3H), 1.15 (s, 3H), 1.03 (d, J=7.0 Hz, 3H), 0.88 (d, J=7.0 Hz, 3H). MS (ESI$^+$) m/z 575.5 (M+H)$^+$.

To a solution of compound 63 (610 mg, 1.06 mmol) in THF (5 mL) and MeOH (5 mL) was added lithium hydroxide, 1 M in water (63.5 mg, 2.65 mmol). The reaction mixture was stirred at RT for 2 h. The reaction mixture was acidified to pH 2-3 with 1N HCl, and concentrated with a rotary evaporator to remove the organic solvents. The residue was lyophilized to dryness to give (S)-5-(4-((S)-2-((S)-2-amino-3-methylbutanamido)-5-ureidopentanamido)phenyl)-4-((tert-butoxycarbonyl)amino)-2,2-dimethylpentanoic acid 64 as a tan solid (593 mg, 94%). MS (ESI$^+$) m/z 593.6 (M+H)$^+$.

To a solution of acid 64 (592 mg, 1.00 mmol) in THF (2 mL) were added 2,5-dioxopyrrolidin-1-yl 6-(2,5-dioxo-2,5-dihydro-1H-pyrrol-1-yl)hexanoate 65 (Cheng et al. 2013, 339 mg, 1.10 mmol) and DIEA (0.524 mL, 3.00 mmol). DMF (0.5 mL) was added to solubilize the reaction mixture. The reaction was stirred at RT for 5 h, and diluted with cold 0.5N aqueous HCl solution (10 mL). The precipitate formed was collected by filtration to give crude product (510 mg, 65%). MS (ESI$^+$) m/z 786.7 (M+H)$^+$.

To a solution of the above product (370 mg, 0.471 mmol) in DCM (1.5 mL) was added TFA (0.5 mL). The reaction mixture was stirred at RT for 1 h and concentrated on a rotary evaporator. The residue was dissolved in CH$_3$CN/water and purified by preparative HPLC (C18 Phenomenex Luna S5 ODS 21×100 mm reverse phase prep HPLC column eluting with 10-90% aq. CH$_3$CN containing 0.05% TFA over a 12 minute gradient) to give (S)-4-amino-5-(4-((S)-2-((S)-2-(6-(2,5-dioxo-2,5-dihydro-1H-pyrrol-1-yl)hexanamido)-3-methylbutanamido)-5-ureidopentanamido)phenyl)-2,2-dimethylpentanoic acid 66 as a white solid (240 mg, 64%). $^1$H NMR (400 MHz, CD$_3$OD) δ 9.83 (s, 1H), 8.25 (d, J=7.3 Hz, 1H), 7.98 (d, J=7.8 Hz, 1H), 7.61 (dd, J=8.4, 1.8 Hz, 2H), 7.24 (d, J=8.4 Hz, 2H), 6.81 (s, 2H), 4.59-4.46 (m, 1H), 4.22-4.11 (m, 2H), 3.50 (t, J=7.1 Hz, 3H), 3.25-3.09 (m, 2H), 2.89 (dd, J=12.0, 7.4 Hz, 2H), 2.30 (t, J=7.4 Hz, 2H), 2.15-2.04 (m, 1H), 1.99-1.87 (m, 2H), 1.80-1.56 (m, 8H), 1.38-1.29 (m, 8H), 1.23 (s, 3H), 1.09 (s, 3H), 0.99 (d, J=6.7 Hz, 6H); MS (ESI$^+$) m/z 686.6 (M+H)$^+$.

To a solution of thiazole acid 10 (Example 2, 36.6 mg, 0.054 mmol) in DMF (1.0 mL) were added HATU (20.44 mg, 0.054 mmol) and DIEA (0.028 mL, 0.161 mmol). The reaction mixture was stirred at RT for 20 min, and then added to a solution of compound 66 (43 mg, 0.054 mmol) in 0.3 ml of DMF. The resulting mixture was stirred at RT for 1.0 h and purified by preparative HPLC (C18 Phenomenex Luna S5 ODS 21×100 mm reverse phase prep HPLC column eluting with 10-90% aq. CH$_3$CN containing 0.05% TFA over a 12 minute gradient) to give compound (IIIa-2) as a white solid (47 mg, 64%). $^1$H NMR (400 MHz, CD$_3$OD) δ 9.75 (s, 1H), 8.81 (d, J=8.3 Hz, 1H), 8.24 (d, J=7.1 Hz, 1H), 8.14 (s, 1H), 7.98 (d, J=7.7 Hz, 1H), 7.90 (br. s., 1H), 7.50 (d, J=8.4 Hz, 2H), 7.18 (d, J=8.4 Hz, 2H), 6.81 (s, 2H), 5.71 (d, J=11.1 Hz, 1H), 4.69-4.59 (m, 1H), 4.48-4.42 (m, 1H), 4.28-4.16 (m, 1H), 3.91 (d, J=11.1 Hz, 1H), 3.50 (t, J=7.1 Hz, 2H), 3.25-3.07 (m, 5H), 2.91-2.78 (m, 3H), 2.68 (s, 3H), 2.29 (t, J=7.4 Hz, 3H), 2.19 (s, 3H), 2.01-1.86 (m, 7H), 1.81-1.54 (m, 14H), 1.37-1.30 (m, 5H), 1.23 (s, 3H), 1.21 (s, 3H), 1.08-0.88 (m, 20H); MS (ESI$^+$) m/z 1234.8 (M+H)$^+$.

Example 8—Compound (IIIa-4)

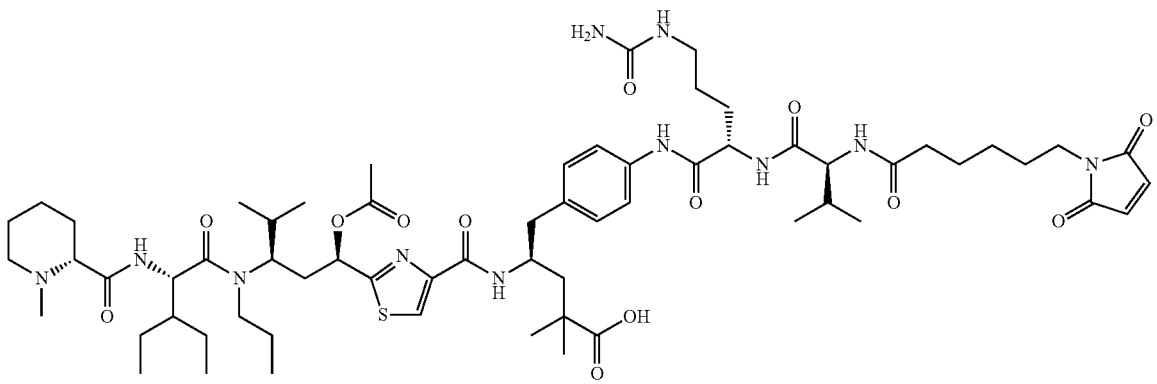

(IIIa-4)

Figure 7A:
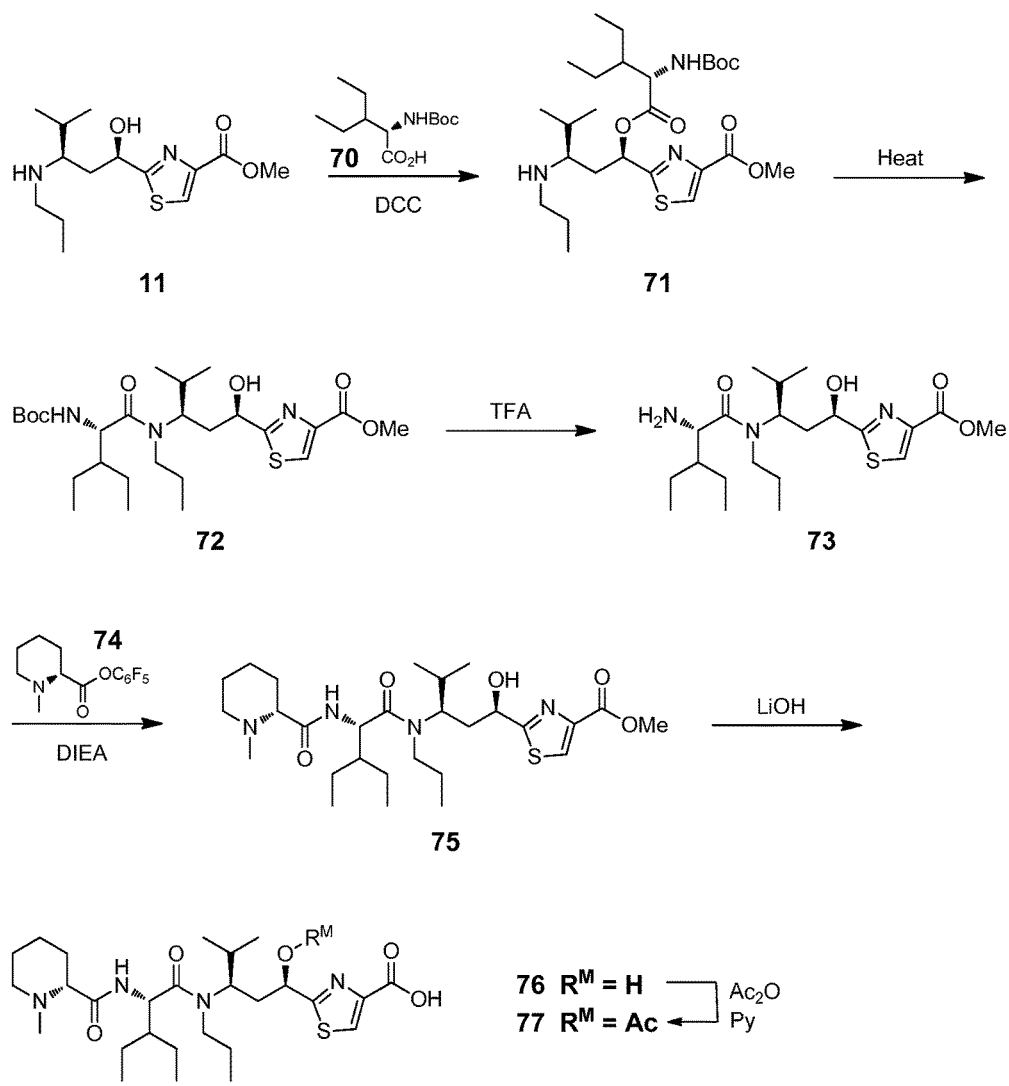
FIGS. 7a and 7b show, in combination, a scheme for the synthesis of analog-linker compound (IIIa-4).
Figure 7B:
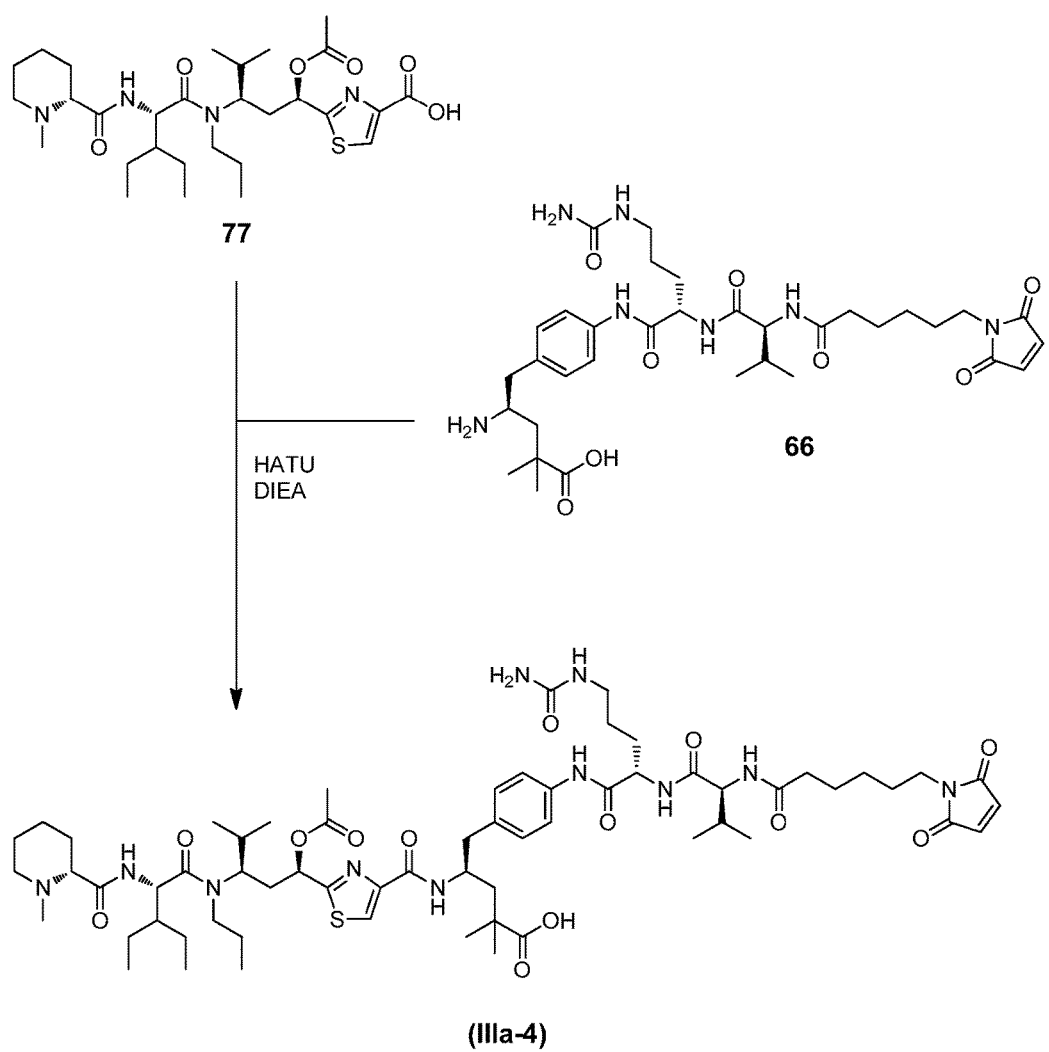

The synthesis of compound (IIIa-4) is described schematically by FIGS. 7a and 7b in combination.

DCC (0.755 g, 3.66 mmol) was added to a mixture of compound 11 (1 g, 3.33 mmol), (S)-2-((tert-butoxycarbonyl)amino)-3-ethylpentanoic acid 70 (0.898 g, 3.66 mmol) and t-butanol hydrate (0.510 g, 3.33 mmol) in DCM (15 mL) at 0° C. The reaction mixture was allowed to warm up to RT and stirred at RT overnight. The solid was filtered off, and the filtrate was concentrated. The crude product was purified by flash chromatography eluting from silica gel with a gradient of 0-10% MeOH in DCM to afford 1.14 g of methyl 2-((6S,9R,11R)-11-isopropyl-2,2-dimethyl-4,7-dioxo-6-(pentan-3-yl)-3,8-dioxa-5,12-diazapentadecan-9-yl)thiazole-4-carboxylate 71 as a colorless oil. MS: (+) m/z 528.3 (M+1).

A solution of compound 71 (0.9 g, 1.705 mmol) in o-xylene (5.1 mL) was heated at 120° C. overnight. The solvent was evaporated off. The crude product was purified by flash chromatography eluting from silica gel with a gradient of 0-100% EtOAc in hexanes to afford 0.44 g of methyl 2-((1R,3R)-3-((S)-2-((tert-butoxycarbonyl)amino)-3-ethyl-N-propylpentanamido)-1-hydroxy-4-methylpentyl)thiazole-4-carboxylate 72 as a light yellow solid. MS: (+) m/z 528.3 (M+1).

TFA (3 mL, 0.834 mmol) was added to a solution of compound 72 (0.44 g, 0.834 mmol) in DCM (6 mL). After the reaction mixture was stirred at RT for 30 min, it was concentrated by removal of solvent, diluted with EtOAC, and washed once with saturated aqueous NaHCO₃. The aqueous solution was back-extracted twice with EtOAc. The combined organic layers were dried, filtered, and concentrated to afford 0.357 g of methyl 2-((1R,3R)-3-((S)-2-amino-3-ethyl-N-propylpentanamido)-1-hydroxy-4-methylpentyl)thiazole-4-carboxylate 73 as a white froth. MS: (+) m/z 428.3 (M+1).

DIEA (0.098 mL, 0.561 mmol) was added to a solution of compound 73 (0.24 g, 0.561 mmol) and (R)-perfluorophenyl 1-methylpiperidine-2-carboxylate 74 (0.868 g, 2.81 mmol) in DMF (3 mL) at RT. The reaction mixture was stirred at RT for 3 h. EtOAc (30 mL) was then added and the organic solution was washed with saturated aqueous NaHCO₃ and brine, dried, filtered and concentrated. The crude product was purified by flash chromatography, eluting from silica gel with a gradient of 0-10% MeOH in DCM to afford 0.178 g of methyl 2-((1R,3R)-3-((S)-3-ethyl-2-((R)-1-methylpiperidine-2-carboxamido)-N-propylpentanamido)-1-hydroxy-4-methylpentyl)thiazole-4-carboxylate 75 as a light yellow oil. MS: (+) m/z 553.3 (M+1).

LiOH (0.031 g, 1.291 mmol) in water (0.5 mL) was added to a solution of compound 75 (0.1784 g, 0.323 mmol) in THF (1 mL) at rt. After the reaction mixture was stirred at RT for 2 h, the solvent was evaporated. The crude product was purified by flash chromatography, eluting from silica gel with a gradient of 0-30% MeOH in DCM to afford 120 mg of 2-((1R,3R)-3-((S)-3-ethyl-2-((R)-1-methylpiperidine-2-carboxamido)-N-propylpentanamido)-1-hydroxy-4-methylpentyl)thiazole-4-carboxylic acid 76 as a white solid. MS: (+) m/z 539.3 (M+1).

A solution of compound 76 (0.121 g, 0.223 mmol) in pyridine (1.8 mL) was cooled in an ice-water bath and acetic anhydride (0.105 mL, 1.114 mmol) was added. The reaction mixture was allowed to warm up to RT and stirred at RT overnight. A 1:1 (v/v) solution of degassed water and THF (8 mL) was added after the reaction mixture was cooled in an ice-water bath. The reaction mixture was then stirred at RT overnight. The solvent was evaporated off. The crude product was purified by flash chromatography eluting from silica gel with a gradient of 0-30% MeOH in DCM to afford 100 mg of 2-((1R,3R)-1-acetoxy-3-((S)-3-ethyl-2-((R)-1-methylpiperidine-2-carboxamido)-N-propylpentanamido)-4-methylpentyl)thiazole-4-carboxylic acid 77 as a white solid. MS: (+) m/z 581.3 (M+1).

DIEA (4.17 µl, 0.024 mmol) was added to a solution of compound 77 (13.89 mg, 0.024 mmol) and HATU (9.09 mg, 0.024 mmol) in DMF (0.5 mL). The pH of the reaction mixture was adjusted to 8-9. After the reaction mixture was stirred at RT for 10 min, compound 66 (16.4 mg, 0.024 mmol) in DMF (1 mL) and DIEA (4.17 µl, 0.024 mmol) were added. The pH of the reaction mixture was adjusted to 8-9. After the reaction mixture was stirred at RT for 20 min, the reaction was quenched by addition of 10 mL 1:1 (v/v) mixture of water containing 0.1% TFA and acetonitrile. The product compound (IIIa-4) was purified by preparative HPLC. MS: (+) m/z 1248.7 (M+1).

Compound (Ia-4) can be prepared from compound (IIIa-4) by removal of the linker, for example by cleavage with cathepsin B.

Example 9—Compound (IIIa-3)

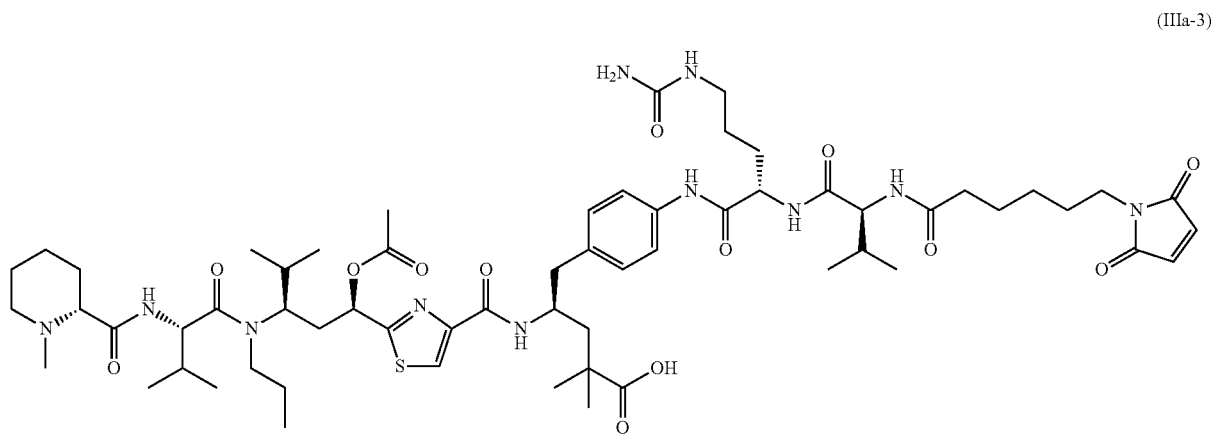 [SMILES: CCCN(C(=O)[C@@H](NC(=O)[C@H]1CCCCN1C)C(C)C)[C@H](C[C@@H](OC(C)=O)c1nc(C(=O)N[C@@H](Cc2ccc(NC(=O)[C@H](CCCNC(N)=O)NC(=O)[C@@H](NC(=O)CCCCCN3C(=O)C=CC3=O)C(C)C)cc2)CC(C)(C)C(=O)O)cs1)C(C)C]

(IIIa-3)

Following the procedures described for Compound IIIa-2, compound 19 (15 mg, 0.022 mmol] was used as a precursor for the synthesis of compound (IIIa-3) (16 mg, 51%): $^1$H NMR (400 MHz, CD$_3$OD) δ 9.73 (s, 1H), 8.21 (d, J=5.9 Hz, 1H), 8.12 (s, 1H), 7.96 (d, J=8.1 Hz, 1H), 7.88 (br. s., 1H), 7.48 (d, J=8.4 Hz, 2H), 7.16 (d, J=8.4 Hz, 2H), 6.79 (s, 2H), 5.76-5.64 (m, 1H), 4.63 (d, J=9.0 Hz, 1H), 4.44 (d, J=5.5 Hz, 2H), 4.18 (t, J=7.7 Hz, 1H), 3.91-3.88 (m, 1H), 3.63-3.58 (m., 2H), 3.51-3.44 (m, 3H), 3.21-3.08 (m, 4H), 2.85-2.76 (m, 3H), 2.67 (s, 3H), 2.34-2.25 (m, 3H), 2.17 (s, 4H), 2.00-1.83 (m, 6H), 1.75 (m, 3H), 1.60 (m, 10H), 1.37-1.25 (m, 4H), 1.22 (s, 3H), 1.20 (s, 3H), 1.09-0.86 (m, 23H); MS (ESI$^+$) m/z 1220.4 (M+H)$^+$.

Example 10—Compound (IIIa-1)

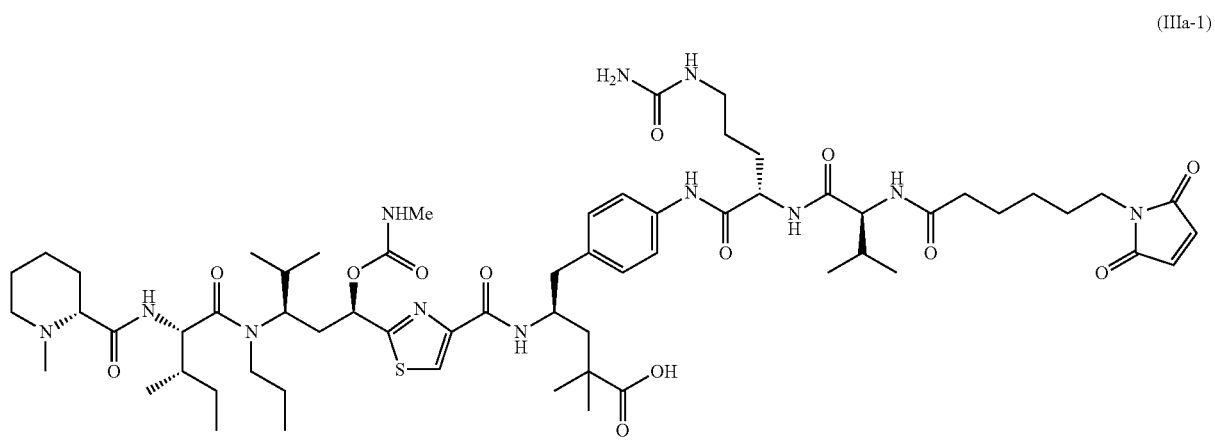 [SMILES: CCCN(C(=O)[C@@H](NC(=O)[C@H]1CCCCN1C)[C@@H](C)CC)[C@H](C[C@@H](OC(=O)NC)c1nc(C(=O)N[C@@H](Cc2ccc(NC(=O)[C@H](CCCNC(N)=O)NC(=O)[C@@H](NC(=O)CCCCCN3C(=O)C=CC3=O)C(C)C)cc2)CC(C)(C)C(=O)O)cs1)C(C)C]

(IIIa-1)

Following the procedures described for compound (IIIa-2), compound 9 (20 mg, 0.034 mmol) was used as a precursor for the synthesis of compound (IIIa-1) (13 mg, 28%): NMR (400 MHz, DMSO-d$_6$) δ 10.85 (s, 1H), 9.73 (s, 1H), 9.21 (d, J=8 Hz, 1H), 8.27 (s, 1H), 8.02 (d, J=8 Hz, 1H), 7.79 (d, J=12 Hz, 1H), 7.66 (br s, 1H), 7.49 (d, J=8 Hz, 2H), 7.41 (d, J=4 Hz, 1H), 7.10 (d, J=8 Hz, 2H), 7.00 (s, 2H), 6.00 (s, 1H), 5.56 (d, J=8 Hz, 1H), 5.42 (s, 1H), 4.51 (t, J=8 Hz, 1H), 4.38-4.21 (m, 2H), 4.19 (t, J=8 Hz, 1H), 3.85-3.79 (m, 1H), 3.08-2.91 (m, 5H), 2.72-2.56 (m, 8H), 2.17-2.08 (m, 5H), 1.98-1.90 (m, 5H), 1.82-1.42 (m, 16H), 1.21-1.17 (m, 3H), 1.08 (d, J=4 Hz, 6H), 0.96-0.75 (m, 21H); MS (ESI$^+$) m/z 1250.1 (M+H)$^+$.

Example 11—Compound (IIIc-1)

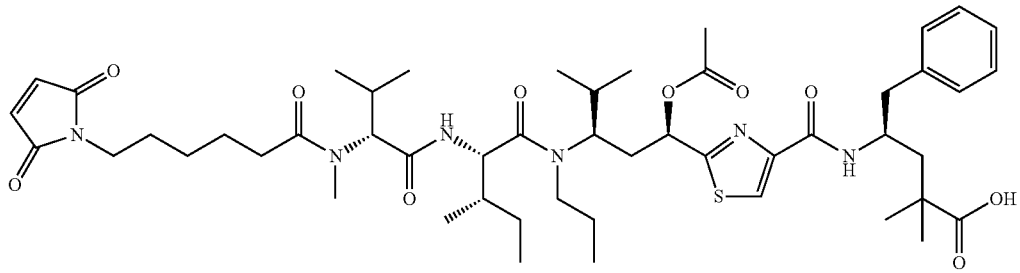

Analog-linker compound (IIIc-1) was prepared from analog (Ic-1) by the HATU-mediated coupling with acid 79:

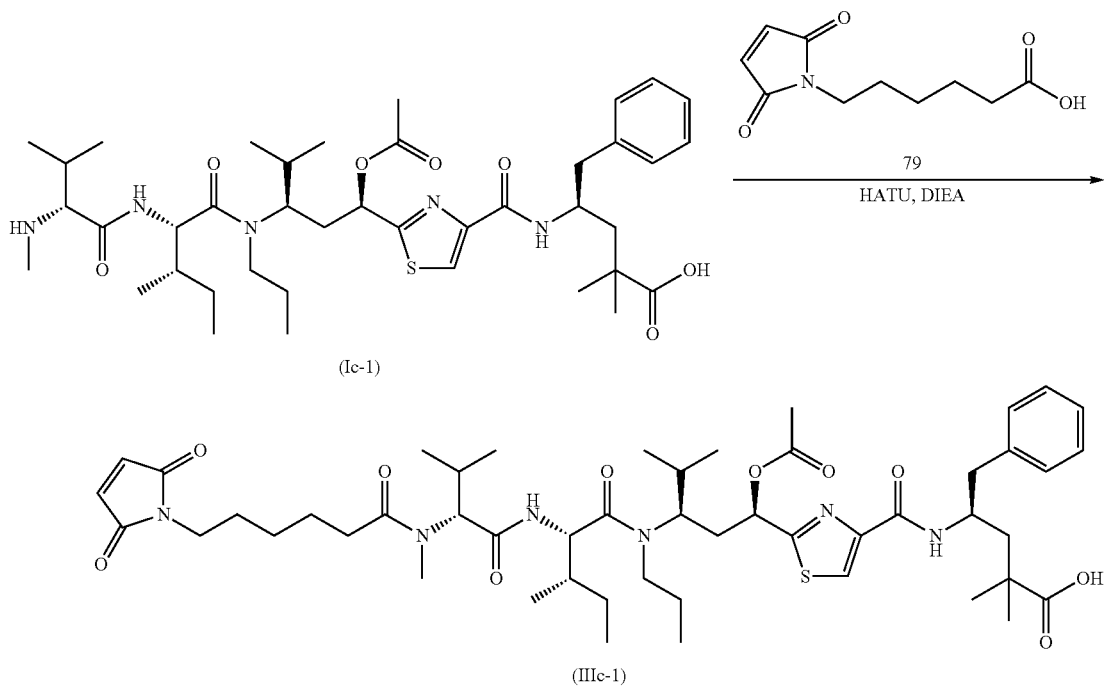

HATU (0.012 g, 0.024 mmol) and 6-(2,5-dioxo-2,5-dihydro-1H-pyrrol-1-yl)hexanoic acid 79 (CAS Reg. No. 55750-53-3, 4.97 mg, 0.024 mmol) were dissolved in DMF (0.5 mL) at RT and the resulting solution then treated with DIEA (0.015 mL, 0.086 mmol). The reaction mixture was stirred at RT for 45 min. A solution of compound (Ic-1), HCl (0.017 g, 0.021 mmol) and DIEA (0.015 mL, 0.086 mmol) was then added and the resulting reaction mixture was stirred at RT for 1 h. The reaction mixture was purified by wet loading on a C-18 reverse phase 50 gram Gold ISCO column, eluting with 40-100% aq $CH_3CN$ with 0.1% TFA over a 12 minute gradient. The appropriate fractions were isolated and freeze dried to afford analog-linker (IIIc-1) (0.008 gm, 38%) as a white solid. $^1$H NMR (400 MHz, acetonitrile-$d_3$) δ 8.02-7.87 (m, 1H), 7.40-7.13 (m, 5H), 6.84-6.61 (m, 2H), 5.77-5.58 (m, 1H), 4.67-4.53 (m, 2H), 4.46-4.28 (m, 2H), 3.51-3.24 (m, 2H), 3.10-2.52 (m, 7H), 2.31-2.08 (m, 9H), 1.92-1.83 (m, 1H), 1.74-1.49 (m, 6H), 1.38-1.25 (m, 2H), 1.21-1.02 (m, 10H), 1.00-0.66 (m, 21H); MS (ESI$^+$) m/z 952.0 (M+H)$^+$.

Example 12—Compound (IIIc-3)

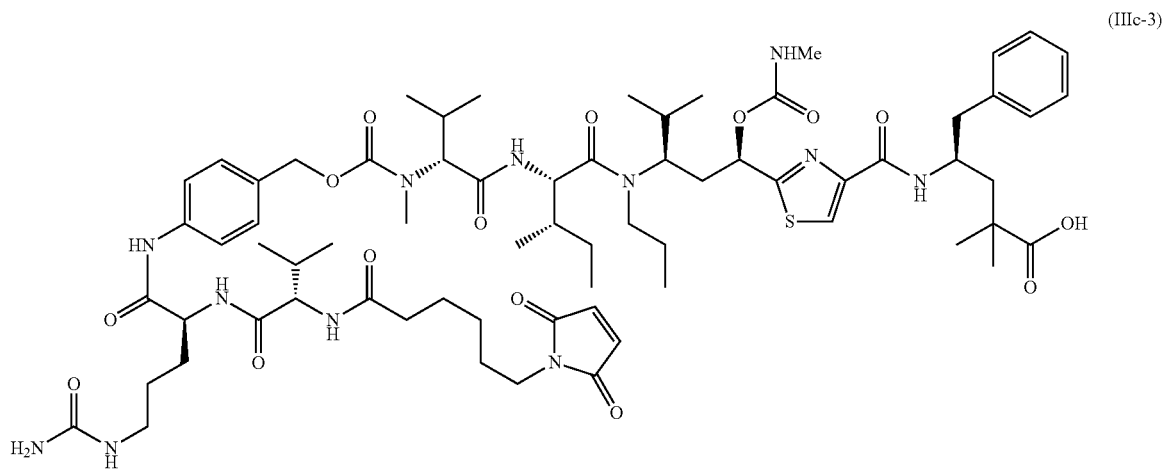 [SMILES: CCCN(C(=O)[C@@H](NC(=O)[C@@H](C(C)C)N(C)C(=O)OCc1ccc(NC(=O)[C@H](CCCNC(N)=O)NC(=O)[C@@H](NC(=O)CCCCCN2C(=O)C=CC2=O)C(C)C)cc1)[C@@H](C)CC)[C@H](C[C@@H](OC(=O)NC)c1nc(C(=O)N[C@@H](Cc2ccccc2)CC(C)(C)C(=O)O)cs1)C(C)C]

Figure 8A:
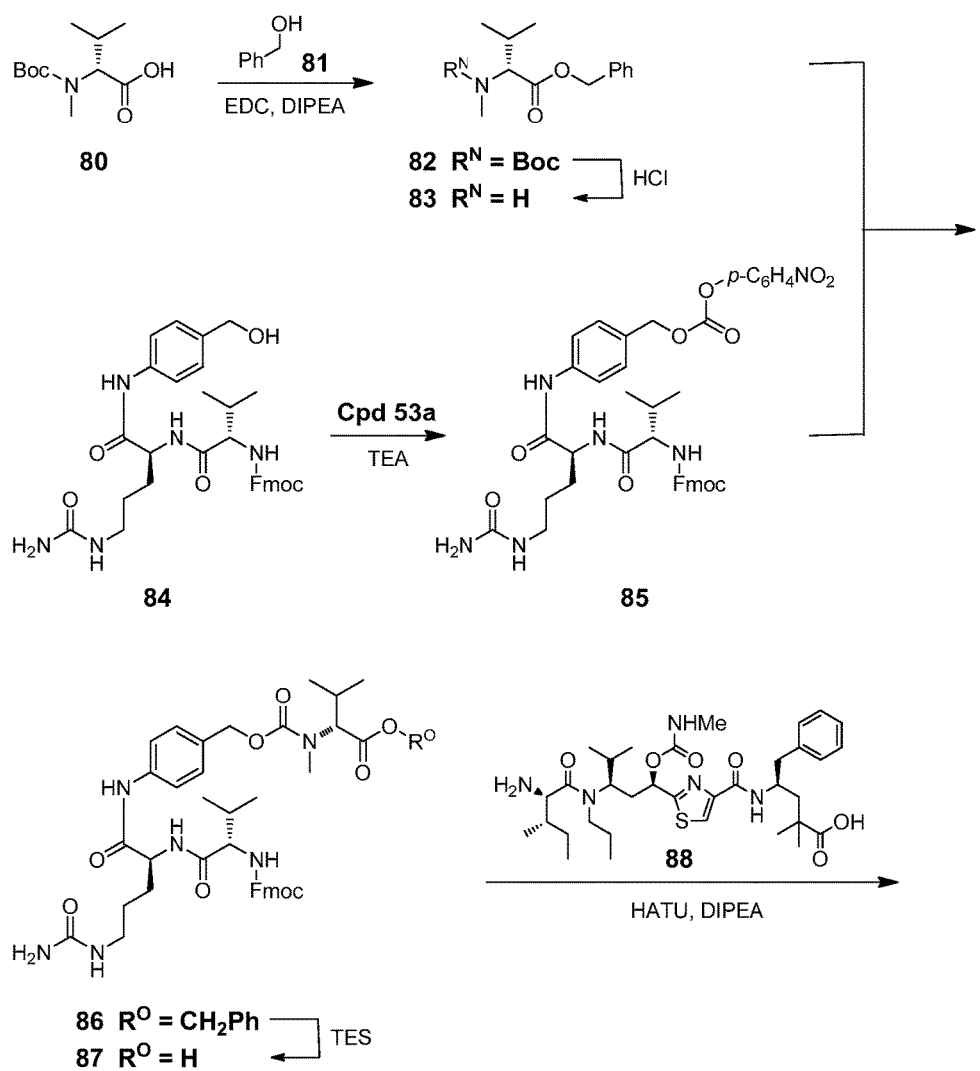
FIGS. 8a and 8b show, in combination, a scheme for the synthesis of analog-linker compound (IIIc-3).
Figure 8B:
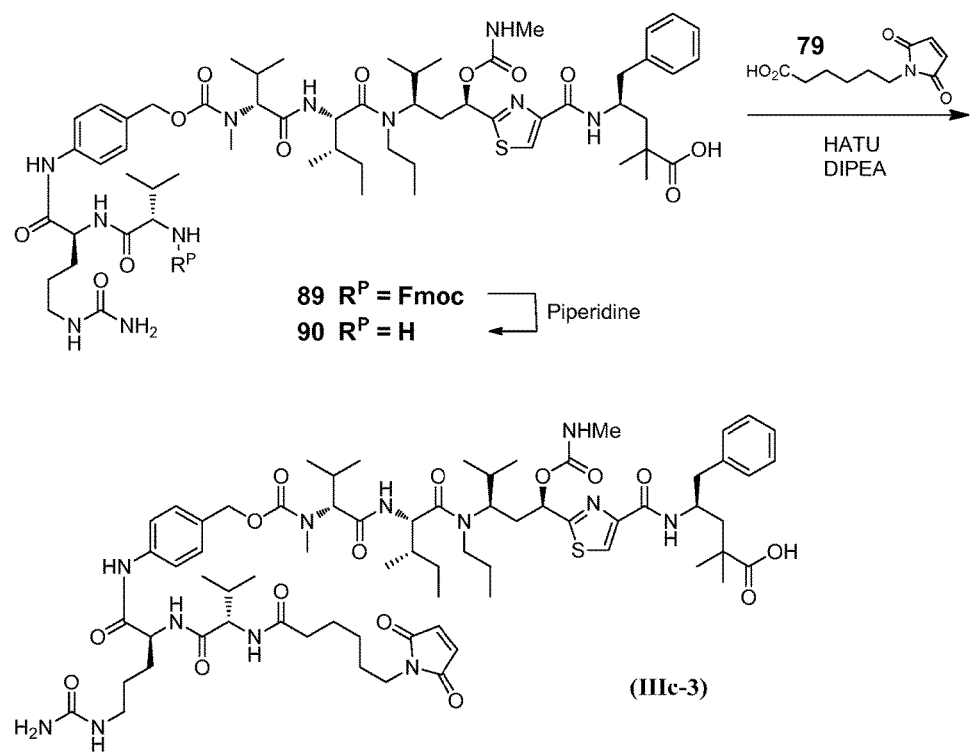

FIGS. 8a and 8b show, in combination, a scheme for making compound (IIIc-2).

(R)-2-((Tert-butoxycarbonyl)(methyl)amino)-3-methylbutanoic acid 80 (1 g, 4.32 mmol), phenylmethanol 81 (0.447 mL, 4.32 mmol), 3H-[1,2,3]triazolo[4,5-b]pyridin-3-ol (0.647 g, 4.76 mmol) and N1-((ethylimino)methylene)-N3,N3-dimethylpropane-1,3-diamine (0.738 g, 4.76 mmol) were dissolved in DMF (3 mL) and the resulting solution was then treated with DIEA (3.01 mL, 17.29 mmol) at RT. The resulting reaction mixture was stirred at RT for 48 h. The crude reaction mixture was wet loaded on to a C-18 reverse phase 50 gm gold ISCO column, eluting 40-100% aq $CH_3CN$ with 0.1% TFA over a 13 min gradient. The appropriate fractions were isolated and quenched with aq. NaCl. The solution was extracted with DCM (3×). The combined organic extracts were dried with anhydrous sodium sulfate, filtered and the filtrate concentrated in vacuo to afford (R)-benzyl 2-((tert-butoxycarbonyl)-(methyl)amino)-3-methylbutanoate 82 (0.63 gm, 45%) as an oil. $^1$H NMR (400 MHz, chloroform-d) δ 7.35 (s, 5H), 5.17 (br. s., 2H), 4.52 (d, J=10.6 Hz, 1H), 4.16 (d, J=10.6 Hz, 1H), 2.92-2.69 (m, 3H), 2.20 (br. s., 1H), 1.45 (d, J=14.3 Hz, 9H), 0.97 (d, J=6.6 Hz, 3H), 0.90 (d, J=6.4 Hz, 3H); MS (ESI$^+$) m/z 322.1 (M+H)$^+$.

Compound 82 (0.63 g, 1.960 mmol) was treated with 4N HCl (4.90 mL, 19.60 mmol) in dioxane (4.9 ml) at RT. The reaction mixture was stirred at RT for 2 h and then concentrated in vacuo. The solid was further dried under high vacuum to afford (R)-benzyl 3-methyl-2-(methylamino)butanoate 83 (0.50 gm, 99%) as solid HCl salt. $^1$H NMR (400 MHz, methanol-d$_4$) δ 7.48-7.27 (m, 5H), 5.44-5.17 (m, 2H), 3.97 (d, J=4.0 Hz, 1H), 2.73 (s, 3H), 2.30 (td, J=7.0, 4.1 Hz, 1H), 1.11-0.81 (m, 6H); MS (ESI$^+$) m/z 222.1 (M+H)$^+$.

(9H-fluoren-9-yl)methyl((S)-1-(((S)-1-((4-(hydroxymethyl)phenyl)amino)-1-oxo-5-ureidopentan-2-yl)amino)-3-methyl-1-oxobutan-2-yl)carbamate 84 (0.5 g, 0.831 mmol) was dissolved in DMF (5 mL) and compound 53a (0.506 g, 1.662 mmol) was added, followed by DIEA (0.23 mL, 1.320 mmol) at RT. The reaction mixture was stirred for 1.5 h at RT. LC/MS showed no starting material was left. The reaction mixture was then treated with 30 mL of $Et_2O$ and stirred at RT for 30 min. The precipitate that formed was filtered and washed with additional $Et_2O$. The solid was dried under high vacuum to afford (9H-fluoren-9-yl)methyl ((S)-3-methyl-1-(((S)-1-((4-(((((4-nitrophenoxy)carbonyl)oxy)methyl)-phenyl)amino)-1-oxo-5-ureidopentan-2-yl)amino)-1-oxobutan-2-yl)carbamate 85 (0.533 gm, 84%) as an off yellow solid. $^1$H NMR (400 MHz, DMSO-d$_6$) δ 10.12 (s, 1H), 8.37-8.22 (m, 2H), 8.12 (d, J=7.5 Hz, 1H), 7.88 (d, J=7.5 Hz, 2H), 7.76-7.50 (m, 5H), 7.44-7.15 (m, 7H), 5.96 (t, J=5.5 Hz, 1H), 5.39 (s, 2H), 5.24 (s, 2H), 4.49-4.39 (m, 1H), 4.34-4.10 (m, 3H), 3.93 (dd, J=8.8, 7.3 Hz, 1H), 3.13-2.82 (m, 2H), 2.05-1.88 (m, 1H), 1.75-1.53 (m, 2H), 1.50-1.28 (m, 2H), 0.87 (dd, J=11.1, 6.7 Hz, 6H); MS (ESI$^+$) m/z 767.3 (M+H)$^+$.

Compound 85 (0.11 g, 0.143 mmol) was dissolved in DMF (1 mL) and the resulting solution was then treated with compound 83 (hydrochloride, 0.11 g, 0.427 mmol), 1H-benzo[d][1,2,3]triazol-1-ol (0.058 g, 0.430 mmol) and then with 2,6-dimethylpyridine (0.117 mL, 1.004 mmol) at RT. The resulting reaction mixture was stirred at RT for 12 h. The crude reaction mixture was wet loaded on to a C-18 reverse phase gold ISCO column eluting 50-100% aq $CH_3CN$ with 0.1% TFA over a 13 minute gradient. The appropriate fractions were isolated and freeze dried to afford (R)-benzyl 2-((((4-((S)-2-((S)-2-((((9H-fluoren-9-yl)methoxy)carbonyl)amino)-3-methylbutanamido)-5-ureidopentanamido)-benzyl)oxy)carbonyl)(methyl)amino)-3-methylbutanoate 86 (0.08 gm, 65%) as a solid. $^1$H NMR (400 MHz, DMSO-d$_6$) δ 8.10 (d, J=7.5 Hz, 1H), 7.88 (d, J=7.5 Hz, 3H), 7.73 (t, J=7.9 Hz, 3H), 7.60-7.51 (m, 3H), 7.43-7.11 (m, 9H), 5.95 (br. s., 1H), 5.39 (br. s., 1H), 5.16-4.86 (m, 4H), 4.50-4.12 (m, 5H), 3.93 (dd, J=8.9, 6.9 Hz, 1H), 3.08-2.88 (m, 2H), 2.84-2.72 (m, 3H), 2.15 (br. s., 1H), 2.05-1.93 (m, 1H), 1.73-1.54 (m, 2H), 1.46-1.24 (m, 2H), 0.98-0.67 (m, 12H); MS (ESI$^+$) m/z 849.6 (M+H)$^+$.

Compound 86 (0.075 g, 0.088 mmol) and 10% Pd/C was treated with MeOH (2 mL). The heterogeneous mixture was then treated with triethylsilane (0.141 mL, 0.883 mmol) at RT. Once the gas evolution ceased (5 min) the reaction was complete. The reaction mixture was filtered through a bed of CELITE™ and the filtrate was concentrated in vacuo. The solid was further dried under high vacuum to afford (R)-2-((((4-((S)-2-((S)-2-((((9H-fluoren-9-yl)methoxy)carbonyl)amino)-3-methylbutanamido)-5-ureidopentanamido)-benzyl)oxy)carbonyl)(methyl)amino)-3-methylbutanoic acid 87 (0.060 gm, 85%) as a solid; MS (ESI$^+$) m/z 759.4 (M+H)$^+$.

Compound 87 (0.06 g, 0.079 mmol) and HATU (0.030 g, 0.079 mmol) were dissolved in 2,6-lutidine (0.037 mL, 0.316 mmol) at RT. The reaction mixture was stirred for 30 min at RT. A solution of acid 88 (0.052 g, 0.079 mmol) and 2,6-lutidine (0.037 mL, 0.316 mmol) in DMF (1 mL) was then added and the resulting reaction mixture was stirred at RT for 1 h. (Compound 88 can be prepared by coupling compounds 35 and 60 and then reducing the azide group with triphenylphosphine.) The crude reaction was wet loaded on to a 50 gm gold C-18 ISCO reverse phase column, eluting 50-100% aq CH$_3$CN with 0.1% TFA over a 12 minute gradient. The appropriate fractions were isolated and freeze dried to afford (S)-4-(2-((5R,8S,11R,13R)-1-(4-((S)-2-((S)-2-((((9H-fluoren-9-yl)methoxy)carbonyl)-amino)-3-methylbutanamido)-5-ureidopentanamido)phenyl)-8-((S)-sec-butyl)-5,11-diisopropyl-4-methyl-3,6,9,15-tetraoxo-10-propyl-2,14-dioxa-4,7,10,16-tetraazaheptadecan-13-yl)thiazole-4-carboxamido)-2,2-dimethyl-5-phenylpentanoic acid 89 (0.038 gm, 34%) as a solid. $^1$H NMR (400 MHz, DMSO-d$_6$) δ 10.09-9.92 (m, 1H), 8.36 (br. s., 1H), 8.08 (br. s., 2H), 7.88 (s, 5H), 7.61-6.96 (m, 10H), 5.96 (d, J=5.7 Hz, 1H), 5.65-5.49 (m, 1H), 5.38 (br. s., 2H), 4.98 (br. s., 2H), 4.59-4.09 (m, 9H), 3.93-3.81 (m, 1H), 3.10-2.94 (m, 2H), 2.87-2.68 (m, 4H), 2.57 (d, J=4.6 Hz, 4H), 2.32 (d, J=1.8 Hz, 3H), 2.16-1.80 (m, 6H), 1.74-1.11 (m, 11H), 1.06-0.95 (m, 5H), 0.92-0.56 (m, 27H); MS (ESI$^+$) m/z 1400.2 (M+H)$^+$.

Compound 89 (0.038 g, 0.027 mmol) was dissolved in DMF (1 mL) with piperidine (0.2 ml, 2.025 mmol). The resulting reaction mixture was stirred at RT for 1 h and purified by wet loading on a C-18 reverse phase ISCO 50 gm gold column, eluting 10-100% aq acetonitrile with 0.1% TFA over a 12 min gradient. The appropriate fractions were isolated and freeze dried to afford (S)-4-(2-((5R,8S,11R,13R)-1-(4-((S)-2-((S)-2-amino-3-methylbutanamido)-5-ureidopentanamido)phenyl)-8-((S)-sec-butyl)-5,11-diisopropyl-4-methyl-3,6,9,15-tetraoxo-10-propyl-2,14-dioxa-4,7,10,16-tetraazaheptadecan-13-yl)thiazole-4-carboxamido)-2,2-dimethyl-5-phenylpentanoic acid 90 (0.027 gm, 76%) as a solid TFA salt. $^1$H NMR (400 MHz, DMSO-d$_6$) δ 8.12-7.97 (m, 1H), 7.58 (d, J=8.4 Hz, 2H), 7.42-7.02 (m, 7H), 6.10-5.94 (m, 1H), 5.59-5.39 (m, 2H), 4.98 (d, J=9.5 Hz, 2H), 4.58-4.11 (m, 6H), 2.99 (br. s., 2H), 2.82-2.71 (m, 5H), 2.66-2.53 (m, 6H), 2.37-2.24 (m, 1H), 2.14-1.90 (m, 3H), 1.75-1.33 (m, 6H), 1.28-0.34 (m, 37H); MS (ESI$^+$) m/z 1178.5 (M+H)$^+$.

Compound 79 (4.71 mg, 0.022 mmol) and HATU (8.47 mg, 0.022 mmol) were dissolved in DMF (0.5 mL). The resulting solution was treated with DIEA (0.013 mL, 0.074 mmol) at rt. The reaction mixture was stirred at RT for 30 minutes. A DMF (0.5 ml) solution of compound 90 TFA salt (0.024 g, 0.019 mmol) and DIEA (0.013 mL, 0.074 mmol) was added and the resulting reaction mixture was then stirred at RT for 1 h. The reaction mixture was purified by wet loading on a C-18 reverse phase 50 gm gold ISCO column, eluting with 30-100% aq CH$_3$CN with 0.1% TFA over a 12 minute gradient. The appropriate fractions were isolated and freeze dried to afford compound (IIIc-3) (0.012 gm, 45%) as a solid. $^1$H NMR (400 MHz, acetonitrile-d$_3$) δ 8.94 (s, 1H), 7.92 (d, J=7.0 Hz, 1H), 7.66 (d, J=7.5 Hz, 2H), 7.44-7.07 (m, 9H), 6.78-6.61 (m, 2H), 5.63 (d, J=11.2 Hz, 1H), 4.96 (br. s., 2H), 4.60 (br. s., 1H), 4.49 (br. s., 1H), 4.38 (br. s., 1H), 4.21-4.01 (m, 3H), 3.55-3.38 (m, 3H), 3.30-3.18 (m, 1H), 3.11-2.95 (m, 3H), 2.92-2.61 (m, 9H), 2.57-2.05 (m, 7H), 1.84-1.39 (m, 12H), 1.34-1.17 (m, 4H), 1.08 (br. s., 3H), 0.98-0.50 (m, 33H); MS (ESI$^+$) m/z 1371.9 (M+H)$^+$.

Example 13—Compound (IIIc-2)

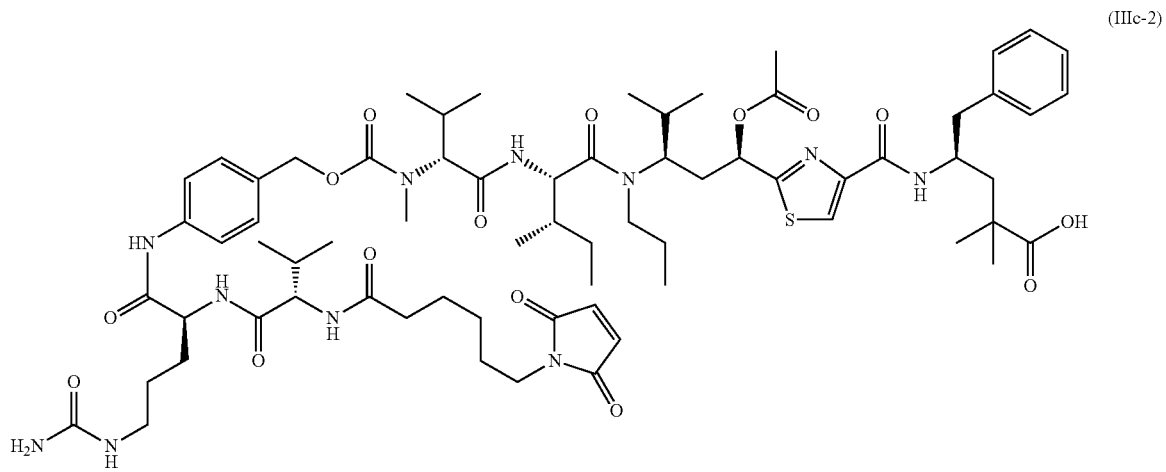 [SMILES: CCCN(C(=O)[C@@H](NC(=O)[C@@H](C(C)C)N(C)C(=O)OCc1ccc(NC(=O)[C@H](CCCNC(N)=O)NC(=O)[C@@H](NC(=O)CCCCCN2C(=O)C=CC2=O)C(C)C)cc1)[C@@H](C)CC)[C@H](C[C@@H](OC(C)=O)c1nc(C(=O)N[C@@H](Cc2ccccc2)CC(C)(C)C(=O)O)cs1)C(C)C]

(IIIc-2)

Analog-linker compound (IIIc-2) was prepared from compound 87 of the previous example and compound 39, generally following the same procedure of the previous example. The analytical properties of compound (IIIc-2) were: $^1$H NMR (400 MHz, acetonitrile-d$_3$) δ 8.93 (br. s., 1H), 8.00-7.88 (m, 1H), 7.76-7.56 (m, 1H), 7.41-7.05 (m, 9H), 6.68 (d, J=7.3 Hz, 2H), 5.76 (d, J=11.2 Hz, 1H), 4.96 (br. s., 2H), 4.61 (br. s., 1H), 4.50 (br. s., 1H), 4.38 (br. s., 1H), 4.20-3.97 (m, 3H), 3.59 (br. s., 1H), 3.43 (t, J=7.0 Hz, 3H), 3.29-3.18 (m, 1H), 3.13-3.03 (m, 1H), 2.96-2.84 (m, 2H), 2.80 (br. s., 4H), 2.54 (br. s., 3H), 2.33-2.17 (m, 2H), 2.10-2.09 (m, 1H), 2.01-1.44 (m, 20H), 1.35-1.01 (m, 10H), 0.98-0.55 (m, 27H); MS (ESI$^+$) m/z 1375.5 (M+H)$^+$.

Example 14—Biologic Activity of Compounds

The cytotoxic activity of compounds of this invention is shown in Table II. The cancer cells lines tested against were: H226 (human lung cancer); N87 (human gastric cancer), OVCAR3 (human ovarian cancer), HCT116 (human colon cancer), HCT116NM46 (HCT116 subline with multi-drug resistance, including to paclitaxel), and ACR (human breast cancer, multi-drug resistant). Table II also includes comparative data against reference compounds (A)-(G) not according to this invention:

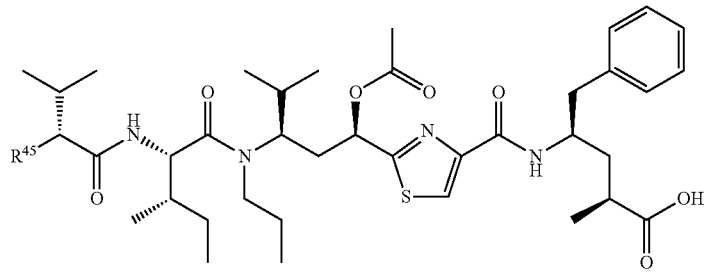

(A) $R^{45}$ = NHMe
(B) $R^{45}$ = $NH_2$

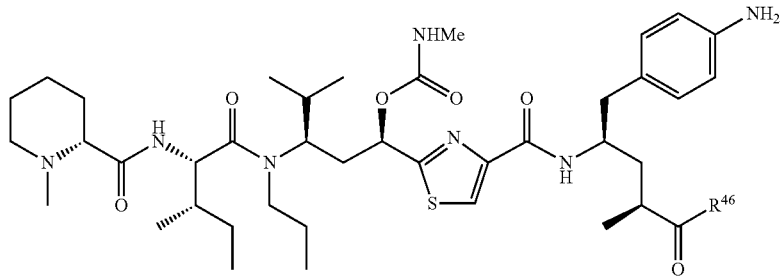

(C) $R^{46}$ = OMe
(D) $R^{46}$ = OH

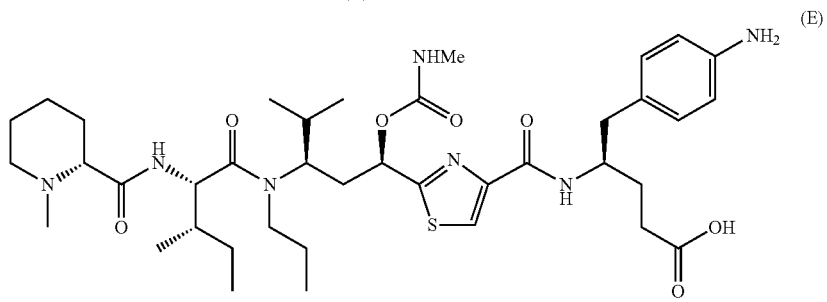

(E)

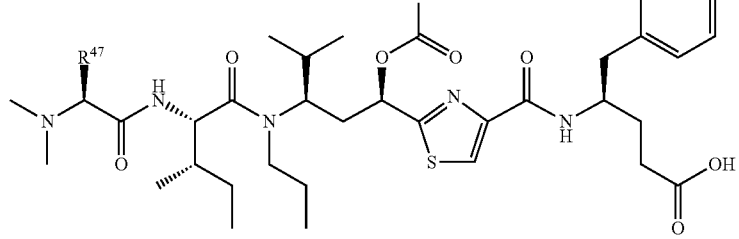

(F) $R^{47}$ = H
(G) $R^{47}$ = $CH(Me)_2$

The ability of test compounds to inhibit cell proliferation was measured by either an ATP luminescence assay or an MTS cell proliferation assay. These two methods yield comparable results. In some instances, both methods were used.

This is a general procedure for an ATP luminescence assay: Cells are seeded at 1×103 cells/well in 96-well plates for 3 h for ATP CellTiterGlo™ assays, respectively. Serial dilutions (1:3) of compounds are added to the wells. Plates are allowed to incubate for 72 h. A CellTiterGlo™ cell viability kit from Promega is used to measure ATP content of cells treated with test compounds following manufacturer's instruction. A decrease in the ATP content is a measure of decrease in cellular viability. The EC50 value—the concentration at which an agent reduces cell viability by 50% of the maximum effect—is determined using PRISM™ software, version 5.0 (GraphPad Software, La Jolla, Calif., USA).

The following is a description of the MTS cell proliferation assay: CellTiter 96 Aqueous Non-Radioactive Cell proliferation Kit from Promega (Madison, Wis.) is used to determine the number of viable cells in cell proliferation assay. Tumor cells are plated at certain seeding densities in sterile 384-well black clear bottom Matrix plates at 40 µL per well and incubated overnight at 37° C. in 5% $CO_2$ before assaying. On the next day, one set of cell plates (T0 plates) is used to determine time zero cell density, and 3-(4,5-dimethylthiazol-2-yl)-5-(3-carboxymethoxyphenyl)-2-(4-sulfophenyl)-2H-tetrazolium is added at 4 µL/well into T0 plates followed by incubation at 37° C. in 5% $CO_2$ for three hours. This tetrazolium reagent is bioreduced by liver cells to form a formazan product which is soluble in aqueous solution. Absorbance at 490 nm is measured on an Envision reader (Perkin Elmer, Boston, Mass.). On the same day, compounds are added into remaining cell plates (T72 plates) and incubated at 37° C. in 5% $CO_2$. After 72 hours, 4 µL MTS reagents are then added into those cell plates. The plates are further incubated at 37° C. in 5% $CO_2$ for three hours and the absorbance values at A490 were measured on an Envision reader.

TABLE II

Activity of Tubulysin Analogs Against Cancer Cell Lines

| Compound | Cancer Cell Line: $EC_{50}$ (nM) | | | | | |
|---|---|---|---|---|---|---|
| | H226 | N87 | OVCAR3 | HCT116 | HCT116/VM46 | ADR |
| (Ia-1) | 0.089 | 0.03 to 0.20 | 0.016 to 0.04 | | | |
| (Ia-2) | 0.33 to 1.1 | 0.65 to 1.0 | 0.07 to 0.1 | 0.58 | 1.22 | 9.5 |
| (Ia-3) | 0.086 | 0.16 | 0.019 | 0.13 | 0.19 | |
| (Ib-1) | 0.63 | 1.7 | 0.07 | | | |
| (Ib-2) | 0.4 | 4.4 | 0.15 | | | |
| (Ic-1) | 0.038 | 0.20 | 0.012 | 0.064 | 0.51 | |
| (Ic-2)) | 0.31 | 0.37 | 0.04 | 0.26 | 7.5 | |
| (A) | 2.4 | 3.2 | 0.46 | | | |
| (B) | 85 | 106 | 57 | 200 | >250 | |
| (C) | 3.3 | | | | | 86 |
| (D) | 11 | 10 | 1.0 | | | 33 |
| (E) | 28 | | | | | 189 |
| (F) | 78 | | | | | |
| (G) | 27 | | | | | 383 |

Example 15—Biological Activity of Conjugates

Analog-linker compounds (IIIa-1)-(IIIa-4) and (IIIc-1)-(IIIc-3) were conjugated to an anti-CD70 human monoclonal antibody and tested for activity against 786-O renal cancer cells, using a $^3$H thymidine assay (Cong et al. 2014). The results are provided in Table III.

TABLE III

Activity of Conjugates against 786-O Renal Cancer Cells

| Conjugate | DAR | $IC_{50}$ (nM) |
|---|---|---|
| (IIIa-1)-CD70 | 2 | 0.34 |
| (IIIa-2)-CD70 | 1.8 | 0.21 |
| (IIIa-3)-CD70 | 3.3 | 0.20 |
| (IIIa-4)-CD70 | 3.1 | 0.23 |
| (IIIc-2)-CD70 | 2.1 | 0.64 |
| (IIIc-3)-CD70 | 2.4 | 1.5 |

Analog-linker compounds (IIIa-1)-(IIIa-4) and (IIIc-1)-(IIIc-3) were conjugated to an anti-mesothelin human monoclonal antibody and tested for activity against N87 gastric cancer cells, using a $^3$H thymidine assay (Cong et al. 2014). The results are provided in Table IV.

TABLE IV

Activity of Conjugates against N87 Gastric Cancer Cells

| Conjugate | DAR | $IC_{50}$ (nM) |
|---|---|---|
| (IIIa-1)-CD70 | 3.5 | 0.14 |
| (IIIa-2)-CD70 | 2.2 | 0.24 |
| (IIIa-3)-CD70 | 2.8 | 0.10 |
| (IIIa-4)-CD70 | 3.1 | 0.25 |
| (IIIc-2)-CD70 | 2.3 | 6 |
| (IIIc-3)-CD70 | 2.4 | 5.7 |

The foregoing detailed description of the invention includes passages that are chiefly or exclusively concerned with particular parts or aspects of the invention. It is to be understood that this is for clarity and convenience, that a particular feature may be relevant in more than just the passage in which it is disclosed, and that the disclosure herein includes all the appropriate combinations of information found in the different passages. Similarly, although the various figures and descriptions herein relate to specific embodiments of the invention, it is to be understood that where a specific feature is disclosed in the context of a particular figure or embodiment, such feature can also be used, to the extent appropriate, in the context of another figure or embodiment, in combination with another feature, or in the invention in general.

Further, while the present invention has been particularly described in terms of certain preferred embodiments, the invention is not limited to such preferred embodiments. Rather, the scope of the invention is defined by the appended claims.

REFERENCES

Full citations for the references cited in abbreviated fashion by first author (or inventor) and date earlier in this specification are provided below. Each of these references is incorporated herein by reference for all purposes. The citation of a reference hereinbelow or elsewhere in this specification is not an admission that such reference is material prior art.

Abe et al., WO 97/21712 (1997).
Boyd et al., US 2008/0279868 A1 (2008).
Boyd et al., U.S. Pat. No. 7,691,962 B2 (2010).
Balasubramanian et al., *Bioorg. Med. Chem. Lett.* 2008, 18, 2996.
Balasubramanian et al., *J. Med. Chem.* 2009, 52 (2), 238.
Chai et al., *Chem. & Biol.* 2010, 17(3), 296.
Chai et al., US 2011/0245295 A1 (2011).
Cheng et al., U.S. Pat. No. 8,394,922 B2 (2013).
Coccia et al., US 2010/0150950 (2010).
Cong et al., US 2014/0227295 A1 (2014).
Davis et al., US 2008/0176958 A1 (2008).
Domling, DE 10 2004 030 227 A1 (2006).
Domling et al., US 2005/0239713 A1 (2005) [2005a].
Domling et al., US 2005/0249740 A1 (2005) [2005b].
Domling et al., *Mol. Diversity* 2005, 9, 141 [2005c].
Domling et al., *Ang. Chem. Int. Ed.* 2006, 45, 7235.
Ellman et al., U.S. Pat. No. 8,476,451 B2 (2013).
Hamel et al., *Curr. Med. Chem.—Anti-Cancer Agents* 2002, 2, 19.
Hoefle et al., DE 100 08 089 A1 (2001).

Hoefle et al., *Pure Appl. Chem.* 2003, 75 (2-3), 167.
Hoefle et al., US 2006/0128754 A1 (2006) [2006a].
Hoefle et al., US 2006/0217360 A1 (2006) [2006b].
Jackson et al., US 2013/0224228 A1 (2013).
Kaur et al., *Biochem. J.* 2006, 396, 235.
Khalil et al., *Chem Bio Chem* 2006, 7, 678.
Leamon et al., *Cancer Res.* 2008, 68 (23), 9839.
Leamon et al., US 2010/0323973 A1 (2010).
Leamon et al., US 2013/0116915 A1 (2013).
Leung et al., US 2002/0169125 A1 (2002).
Low et al., US 2010/0324008 A1 (2010).
Lundquist et al., *Org. Lett.* 2001, 3, 781.
Mammen et al., US 2013/0323271 A1 (2013).
Miao et al., WO 2013/173393 A1 (2013).
Neri et al., *Chem Med Chem* 2006, 1, 175.
Pando et al., *J. Am. Chem. Soc.*, 2011, 133, 7692.
Patterson et al., *Chem. Eur. J.* 2007, 13, 9534.
Patterson et al., *J. Org. Chem.* 2008, 73, 4362.
Peltier et al., *J. Am. Chem. Soc.* 2006, 128, 16018.
Raghavan et al., *J. Med. Chem.* 2008, 51, 1530.
Reddy et al., *Mol. Pharmaceutics* 2009, 6 (5), 1518.
Reichenbach et al. WO 98/13375 A1 (1998).
Richter, US 2012/0129779 A1 (2012) [2012a]
Richter, US 2012/0252738 A1 (2012) [2012b].
Richter, US 2012/0252739 A1 (2012) [2012c].
Sani et al., *Angew. Chem. Int. Ed.* 2007, 46, 3526.
Sasse et al., *J. Antibiotics* 2000, 53 (9), 879.
Sasse et al., *Nature Chem. Biol.* 2007, 3 (2), 87.
Schluep et al., *Clin. Cancer Res.* 2009, 15 (1), 181.
Schrama et al., *Nature Rev. Drug Disc.* 2006, 5, 147.
Shankar et al., *SYNLETT* 2009, 8, 1341-1345.
Shankar et al., *Org. Biomol. Chem.*, 2013, 11(14), 2273.
Shibue et al., *Tetrahedron Lett.* 2009, 50, 3845.
Shibue et al., *Chemistry Eur. J.*, 2010, 16(38), 11678.
Shibue et al., *Bioorg. Med. Chem.*, 2011, 21, 431.
Sreejith et al., *SYNLETT* 2011, No. 12, 1673.
Steinmetz et al., *Angew. Chem. Int. Ed.* 2004, 43, 4888.
Terrett et al., U.S. Pat. No. 8,268,970 B2 (2012).
Terrette et al., US 2010/0209432 A1 (2010).
Ullrich et al., *Angew. Chemie Int. Ed.* 2009, 48, 4422.
Vlahov et al., *Bioorg. Med. Chem. Lett.* 2008, 18 (16), 4558 [2008a].
Vlahov et al., US 2008/0248052 A1 (2008) [2008b].
Vlahov et al., US 2010/0240701 A1 (2010) [2010a].
Vlahov et al., US 2010/0048490 A1 (2010) [2010b].
Vlahov et al., *Bioorg. Med. Chem. Lett.* 2011, 21, 6778.
Vlahov et al., US 2014/0107316 A1 (2014) [2014a].
Vlahov et al., WO 2014/078484 A1 (2014) [2014b].
Wang et al., *Chem. Biol. Drug. Des.* 2007, 70, 75.
Wessjohann et al., US 2013/0217638 A1 (2013).
Wipf et al., *Org. Lett.* 2004, 6 (22), 4057.
Wipf et al., *Org. Lett.* 2007, 9 (8), 1605.
Wipf et al., US 2010/0047841 A1 (2010).
Zanda et al., U.S. Pat. No. 8,580,820 B2 (2013).
Zhao et al., WO 2014/009774 A1 (2014) [2014a].
Zhao et al., WO 2014/080251 A1 (2014) [2014b].

What is claimed is:
1. A tubulysin analog having a structure represented by formula (I)

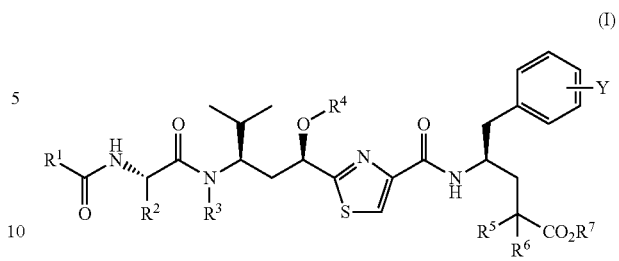

wherein
$R^1$ is

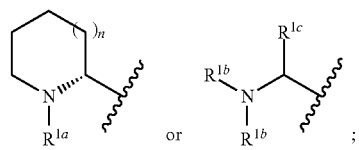

wherein
$R^{1a}$ is H, $C_1$-$C_5$ alkyl, $C_2$-$C_5$ alkenyl, $C_2$-$C_5$ alkynyl, $CO(C_1$-$C_5$ alkyl), $CO(C_2$-$C_5$ alkenyl), or $CO(C_2$-$C_5$ alkynyl);

each $R^{1b}$ is independently H or $C_{1-3}$ alkyl;

$R^{1c}$ is H, Me, or $CH(Me)_2$; and n is 0, 1, or 2;

$R^2$ is H, unsubstituted or substituted $C_1$-$C_{10}$ alkyl, unsubstituted or substituted $C_2$-$C_{10}$ alkenyl, unsubstituted or substituted $C_2$-$C_{10}$ alkynyl, unsubstituted or substituted aryl, unsubstituted or substituted heteroaryl, unsubstituted or substituted $(CH_2)_{1-2}O(C_1$-$C_{10}$ alkyl), unsubstituted or substituted $(CH_2)_{1-2}O(C_2$-$C_{10}$ alkenyl), unsubstituted or substituted $(CH_2)_{1-2}O(C_2$-$C_{10}$ alkynyl), $(CH_2)_{1-2}OC(=O)(C_1$-$C_{10}$ alkyl), unsubstituted or substituted $(CH_2)_{1-2}OC(=O)(C_2$-$C_{10}$ alkenyl), unsubstituted or substituted $(CH_2)_{1-2}OC(=O)(C_2$-$C_{10}$ alkynyl), unsubstituted or substituted $C(=O)(C_1$-$C_{10}$ alkyl), unsubstituted or substituted $C(=O)(C_2$-$C_{10}$ alkenyl), unsubstituted or substituted $C(=O)(C_2$-$C_{10}$ alkynyl), unsubstituted or substituted cycloaliphatic, unsubstituted or substituted heterocycloaliphatic, unsubstituted or substituted arylalkyl, or unsubstituted or substituted alkylaryl;

$R^3$ is H, unsubstituted or substituted $C_1$-$C_{10}$ alkyl, unsubstituted or substituted $C_2$-$C_{10}$ alkenyl, unsubstituted or substituted $C_2$-$C_{10}$ alkynyl, unsubstituted or substituted aryl, unsubstituted or substituted heteroaryl, unsubstituted or substituted $(CH_2)_{1-2}O(C_1$-$C_{10}$ alkyl), unsubstituted or substituted $(CH_2)_{1-2}O(C_2$-$C_{10}$ alkenyl), unsubstituted or substituted $(CH_2)_{1-2}O(C_2$-$C_{10}$ alkynyl), $(CH_2)_{1-2}OC(=O)(C_1$-$C_{10}$ alkyl), unsubstituted or substituted $(CH_2)_{1-2}OC(=O)(C_2$-$C_{10}$ alkenyl), unsubstituted or substituted $(CH_2)_{1-2}OC(=O)(C_2$-$C_{10}$ alkynyl), unsubstituted or substituted $C(=O)(C_1$-$C_{10}$ alkyl), unsubstituted or substituted $C(=O)(C_2$-$C_{10}$ alkenyl), unsubstituted or substituted $C(=O)(C_2$-$C_{10}$ alkynyl), unsubstituted or substituted cycloaliphatic, unsubstituted or substituted heterocycloaliphatic, unsubstituted or substituted arylalkyl, unsubstituted or substituted alkylaryl, or

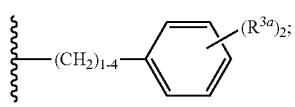

wherein each $R^{3a}$ is independently H, NH$_2$, NHMe, C$_1$, F, Me, Et, or CN;

$R^4$ is

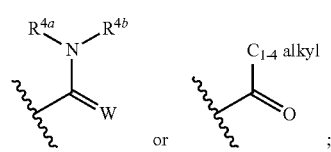

wherein $R^{4a}$ and $R^{4b}$ are independently H, C$_1$-C$_5$ alkyl, CH$_2$(C$_5$-C$_6$ cycloalkyl), CH$_2$C$_6$H$_5$, C$_6$H$_5$, or CH$_2$CH$_2$OH; and W is O or S;

$R^5$ and $R^6$ are each Me or combine with the carbon to which they are bonded to form a cyclopropyl ring;

$R^7$ is H or C$_1$-C$_3$ alkyl; and

Y is H, OH, C$_1$, F, CN, Me, Et, NO$_2$, or NH$_2$;

or a pharmaceutically acceptable salt thereof.

2. A tubulysin analog according to claim 1, having a structure represented by formula (Ia):

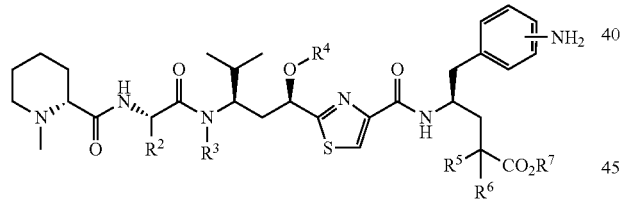

wherein $R^2$ is Me, Et, CH$_2$CH$_2$CH$_3$, CH(Me)$_2$, CH(Et)$_2$, or

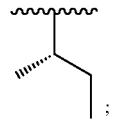

;

$R^3$ is H, C$_1$-C$_5$ alkyl, C$_1$-C$_5$ alkenyl, C$_1$-C$_5$ alkynyl, CH$_2$OC(=O)C$_1$-C$_5$ alkyl, CH$_2$OC(=O)C$_1$-C$_5$ alkenyl, or CH$_2$OC(=O)C$_1$-C$_5$ alkynyl; and $R^4$, $R^5$, $R^6$ and $R^7$ are as defined in claim 1.

3. A tubulysin analog according to claim 1, having a structure represented by formula (Ia')

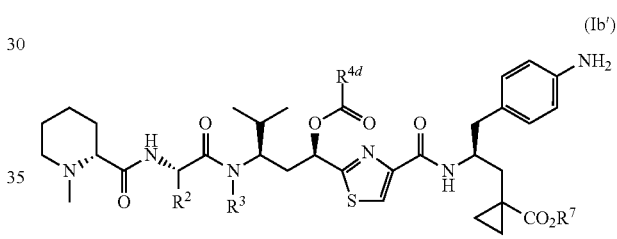

wherein $R^2$ is CH(Me)$_2$, CH(Et)$_2$, or

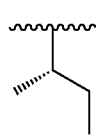

;

$R^3$ is C$_{1-5}$ alkyl;

$R^{4d}$ is Me or NHMe; and $R^7$ is H, Me, or Et.

4. A tubulysin analog according to claim 1, having a structure represented by formula (Ib')

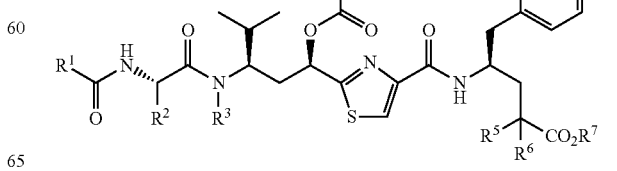

wherein $R^2$ is CH(Me)$_2$, CH(Et)$_2$, or

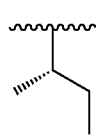

;

$R^3$ is C$_{1-5}$ alkyl;

$R^{4d}$ is Me or NHMe; and $R^7$ is H, Me, or Et.

5. A tubulysin analog according to claim 1, having a structure represented by formula (Ic)

(Ic)

wherein
R¹ is

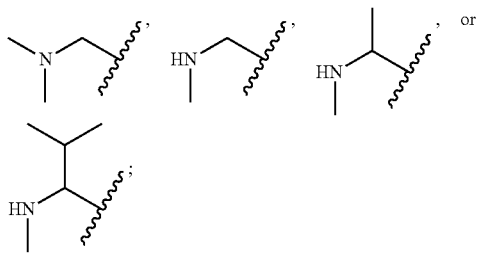

R² is CH(Me)₂, CH(Et)₂, or

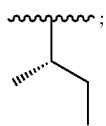;

R³ is $C_{1-5}$ alkyl;
$R^{4d}$ is Me or NHMe;
$R^5$ and $R^6$ are each Me or combine with the carbon to which they are bonded to form a cyclopropyl ring; and
$R^7$ is H, Me, or Et.

6. A tubulysin analog according to claim 5, wherein $R^5$ and $R^6$ are each Me.

7. A compound according to claim 1, having a structure represented by the formula

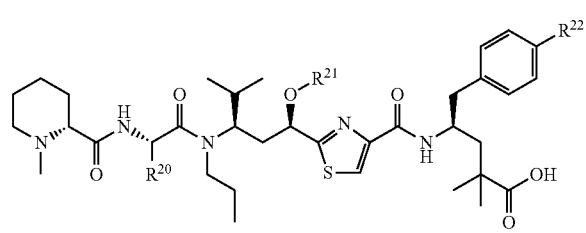

wherein $R^{20}$, $R^{21}$, and $R^{22}$ are as set for the below:

| Compound | $R^{20}$ | $R^{21}$ | $R^{22}$ |
| --- | --- | --- | --- |
| (Ia-1) | | | NH₂ |
| (Ia-2) | | NHMe | NH₂ |
| (Ia-3) | | | NH₂ |
| (Ia-4) | | | NH₂ |
| (Ia-5) | | | NO₂ |
| (Ia-6) | | NHMe | NO₂ |
| (Ia-7) | | | NO₂. |

8. A compound according to claim 1, having a structure represented by the formula

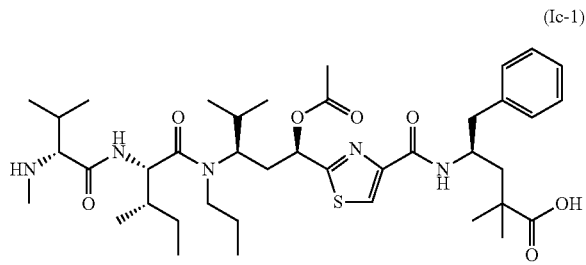

wherein $R^{23}$ and $R^{24}$ are as set forth below:

| Compound | $R^{23}$ | $R^{24}$ |
| --- | --- | --- |
| (Ib-1) | NH₂ | H |
| (Ib-2) | NH₂ | Me |
| (Ib-3) | NO₂ | H |
| (Ib-4) | NO₂ | Me. |

9. A compound according to claim 8, wherein $R^{23}$ in NH₂ and $R^{24}$ is H.

10. A compound according to claim 1, having a structure represented by formula (Ic-1) or (Ic-2):

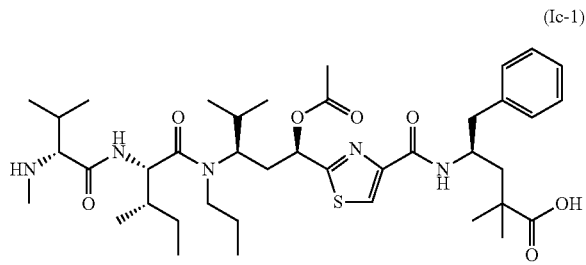

(Ic-1)

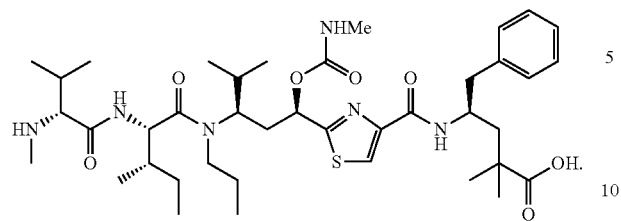
(Ic-2)
* * * * *